(12) United States Patent
Nanthakumar et al.

(10) Patent No.: US 7,159,740 B2
(45) Date of Patent: Jan. 9, 2007

(54) METHOD AND APPARATUS FOR PARALLEL DISPENSING OF DEFINED VOLUMES OF SOLID PARTICLES

(75) Inventors: Elizabeth Nanthakumar, Carlsbad, CA (US); Josef Backes, Pruem (DE); Siegfried Unger, Pruem (DE)

(73) Assignee: Sequenom, Inc., San Diego, CA (US)

( * ) Notice: Subject to any disclaimer, the term of this patent is extended or adjusted under 35 U.S.C. 154(b) by 533 days.

(21) Appl. No.: 10/281,428

(22) Filed: Oct. 25, 2002

(65) Prior Publication Data

US 2003/0124735 A1    Jul. 3, 2003

Related U.S. Application Data

(60) Provisional application No. 60/348,745, filed on Oct. 26, 2001, provisional application No. 60/348,107, filed on Oct. 26, 2001.

(51) Int. Cl.
*B65H 5/00* (2006.01)
*B65H 3/08* (2006.01)
*G05B 21/00* (2006.01)
*G01N 1/10* (2006.01)
*B01L 3/02* (2006.01)

(52) U.S. Cl. ............... 221/224; 208/211; 208/221; 208/224; 208/252; 700/266; 436/180; 422/100; 422/921; 73/864; 73/863.32; 73/864.16

(58) Field of Classification Search ............... 422/100, 422/919, 921–923; 73/863.32, 864, 864.01, 73/864.13, 864.16; 221/208, 211, 224, 252; 222/216; 436/180; 700/266
See application file for complete search history.

(56) References Cited

U.S. PATENT DOCUMENTS 4,101,284 A * 7/1978 Difiglio et al. ............. 422/100
4,285,907 A * 8/1981 Hugemann et al. ......... 422/100
4,554,839 A * 11/1985 Hewett et al. ........... 73/864.16
4,865,986 A    9/1989 Coy et al. .................... 435/290
4,967,604 A * 11/1990 Arpagaus et al. ........ 73/864.13

(Continued)

FOREIGN PATENT DOCUMENTS

EP    0689610    1/1996

(Continued)

OTHER PUBLICATIONS

Chi et al., "Development of validationof a liquid chromatography-mass spectrometric method for the determination of DPC 423, an antithrombotic agent, in rat and dog plasma", *J Chromatogr B Analyt Technol Biomed Life Sci.*, 783(1):163-172 (2003).

(Continued)

*Primary Examiner*—Brian R. Gordon
(74) *Attorney, Agent, or Firm*—Stephen C. Beuerle; Procopio Cory Hargreaves & Savitch LLP

(57) ABSTRACT

A sample preparation system provides an automated process that dispenses appropriate amounts of solid material into wells of a microtiter plate for mixing into a suspension. The system utilizes an array of hollow tubes that are lowered into a particle reservoir such that particle material is forced up into the tubes. During loading, solid plungers in the tubes are positioned a known distance from the open end of the tubes. When the particle material is to be dispensed, the plungers are lowered to push the particle material out of the tubes and into receiving wells of the microtiter plate. The plunger stroke and internal diameter of the tubes defines the dispensed volume of particle material.

47 Claims, 44 Drawing Sheets

U.S. PATENT DOCUMENTS

| | | | | |
|---|---|---|---|---|
| 5,038,852 | A | 8/1991 | Johnson et al. | 165/12 |
| 5,104,621 | A | 4/1992 | Pfost et al. | 422/67 |
| 5,187,084 | A | 2/1993 | Hallsby | 435/91 |
| 5,435,378 | A | 7/1995 | Heine et al. | 165/64 |
| 5,547,835 | A | 8/1996 | Koster | 435/6 |
| 5,601,141 | A | 2/1997 | Gordon et al. | 165/263 |
| 5,605,798 | A | 2/1997 | Koster | 435/6 |
| 5,616,301 | A | 4/1997 | Moser et al. | 422/104 |
| 5,622,824 | A | 4/1997 | Koster | 435/6 |
| 5,691,141 | A | 11/1997 | Koster | 435/6 |
| 5,696,330 | A * | 12/1997 | Heinonen | 73/864.13 |
| 5,722,470 | A * | 3/1998 | Kedar et al. | 141/100 |
| 5,777,324 | A | 7/1998 | Hillenkamp | 250/288 |
| 5,798,035 | A | 8/1998 | Kirk et al. | 205/335 |
| 5,851,765 | A | 12/1998 | Koster | 435/6 |
| 5,865,224 | A | 2/1999 | Ally et al. | 141/130 |
| 5,872,003 | A | 2/1999 | Koster | 435/283.1 |
| 5,885,430 | A | 3/1999 | Kernan et al. | 204/453 |
| 5,900,481 | A | 5/1999 | Lough et al. | 536/55.3 |
| 5,928,906 | A | 7/1999 | Koster et al. | 435/91.2 |
| 5,935,859 | A * | 8/1999 | Elliott et al. | 436/54 |
| 6,022,688 | A | 2/2000 | Jurinke et al. | 435/6 |
| 6,024,925 | A | 2/2000 | Little et al. | 422/100 |
| 6,043,031 | A | 3/2000 | Koster et al. | 435/6 |
| 6,047,854 | A * | 4/2000 | Demers et al. | 221/129 |
| 6,074,609 | A * | 6/2000 | Gavin et al. | 422/99 |
| 6,074,823 | A | 6/2000 | Koster | 435/6 |
| 6,111,251 | A | 8/2000 | Hillenkamp | 250/288 |
| 6,132,582 | A | 10/2000 | King et al. | 204/604 |
| 6,133,436 | A | 10/2000 | Koster et al. | 536/24.3 |
| 6,140,053 | A | 10/2000 | Koster | 435/6 |
| 6,146,854 | A | 11/2000 | Koster et al. | 435/91.1 |
| 6,187,270 | B1 * | 2/2001 | Schmitt et al. | 422/101 |
| 6,194,144 | B1 | 2/2001 | Koster | 435/6 |
| 6,197,498 | B1 | 3/2001 | Koster | 435/5 |
| 6,207,370 | B1 | 3/2001 | Little et al. | 435/6 |
| 6,221,601 | B1 | 4/2001 | Koster et al. | 435/6 |
| 6,221,605 | B1 | 4/2001 | Koster | 435/6 |
| 6,225,061 | B1 | 5/2001 | Becker et al. | 435/6 |
| 6,225,450 | B1 | 5/2001 | Koster | 536/22.1 |
| 6,235,478 | B1 | 5/2001 | Koster | 435/6 |
| 6,238,871 | B1 | 5/2001 | Koster | 435/6 |
| 6,255,116 | B1 * | 7/2001 | Leber et al. | 436/54 |
| 6,258,324 | B1 | 7/2001 | Yiu | 422/100 |
| 6,258,538 | B1 | 7/2001 | Koster et al. | 435/6 |
| 6,268,131 | B1 | 7/2001 | Kang et al. | 435/6 |
| 6,268,144 | B1 | 7/2001 | Koster | 435/6 |
| 6,277,573 | B1 | 8/2001 | Koster | 435/6 |
| 6,300,076 | B1 | 10/2001 | Koster | 435/6 |
| 6,303,309 | B1 | 10/2001 | Jurinke et al. | 435/6 |
| 6,322,970 | B1 | 11/2001 | Little et al. | 435/6 |
| 6,324,925 | B1 * | 12/2001 | Suovaniemi et al. | 73/864.14 |
| 6,368,562 | B1 | 4/2002 | Yao | 422/100 |
| 6,374,683 | B1 * | 4/2002 | Hunicke-Smith et al. | 73/864.17 |
| 6,387,628 | B1 | 5/2002 | Little et al. | 435/6 |
| 6,399,024 | B1 | 6/2002 | Bevirt et al. | 422/100 |
| 6,416,718 | B1 | 7/2002 | Maiefski et al. | 422/103 |
| 6,423,966 | B1 | 7/2002 | Hillenkamp et al. | 250/288 |
| 6,428,955 | B1 | 8/2002 | Koster et al. | 435/6 |
| 6,432,365 | B1 | 8/2002 | Levin et al. | 422/100 |
| 6,432,719 | B1 * | 8/2002 | Vann et al. | 436/180 |
| 6,436,635 | B1 | 8/2002 | Fu et al. | 435/6 |
| 6,451,260 | B1 | 9/2002 | Dusterhoft et al. | 422/68.1 |
| 6,455,325 | B1 * | 9/2002 | Tajima | 436/526 |
| 6,468,748 | B1 | 10/2002 | Monforte et al. | 435/6 |
| 6,471,917 | B1 * | 10/2002 | Velkovska et al. | 422/100 |
| 6,485,692 | B1 | 11/2002 | Freitag et al. | 422/130 |
| 6,485,913 | B1 | 11/2002 | Becker et al. | 435/6 |
| 6,499,364 | B1 * | 12/2002 | Suovaniemi | 73/864.15 |
| 6,500,621 | B1 | 12/2002 | Koster | 435/6 |
| 6,509,193 | B1 | 1/2003 | Tajima | 436/49 |
| 6,517,779 | B1 | 2/2003 | Luttermann et al. | 422/100 |
| 6,550,349 | B1 * | 4/2003 | Godin | 73/864.13 |
| 6,558,902 | B1 | 5/2003 | Hillenkamp | 435/6 |
| 6,566,055 | B1 | 5/2003 | Monforte et al. | 435/6 |
| 6,569,385 | B1 | 5/2003 | Little et al. | 422/100 |
| 6,715,369 | B1 * | 4/2004 | Baba et al. | 73/864.16 |
| 6,887,431 | B1 * | 5/2005 | Vann et al. | 422/100 |
| 2001/0008615 | A1 * | 7/2001 | Little et al. | 422/102 |
| 2001/0020588 | A1 * | 9/2001 | Adourian et al. | 204/451 |
| 2002/0005478 | A1 * | 1/2002 | Hillenkamp et al. | 250/288 |
| 2002/0009394 | A1 * | 1/2002 | Koster et al. | 422/65 |
| 2002/0012902 | A1 * | 1/2002 | Fuchs et al. | 435/4 |
| 2002/0015666 | A1 * | 2/2002 | Vann et al. | 422/100 |
| 2002/0040130 | A1 * | 4/2002 | Braun | 536/23.1 |
| 2002/0042046 | A1 * | 4/2002 | Kim et al. | 435/5 |
| 2002/0042112 | A1 * | 4/2002 | Koster et al. | 435/174 |
| 2002/0104389 | A1 * | 8/2002 | Hovey et al. | 73/864.17 |
| 2002/0109085 | A1 * | 8/2002 | Hillenkamp et al. | 250/288 |
| 2002/0137046 | A1 * | 9/2002 | Koster | 435/6 |
| 2002/0142483 | A1 * | 10/2002 | Yao et al. | 436/180 |
| 2002/0150903 | A1 * | 10/2002 | Koster | 435/6 |
| 2002/0176803 | A1 * | 11/2002 | Hamel et al. | 422/100 |
| 2002/0187488 | A1 * | 12/2002 | Lin et al. | 435/6 |
| 2003/0003465 | A1 * | 1/2003 | Little et al. | 422/100 |
| 2003/0021734 | A1 * | 1/2003 | Vann et al. | 422/100 |
| 2003/0026732 | A1 * | 2/2003 | Gordon et al. | 422/63 |
| 2003/0036057 | A1 * | 2/2003 | Braun et al. | 435/6 |
| 2003/0111494 | A1 * | 6/2003 | Lin et al. | 222/505 |
| 2003/0166299 | A1 * | 9/2003 | Velkovska et al. | 436/180 |
| 2004/0047765 | A1 * | 3/2004 | Gordon et al. | 422/63 |
| 2004/0126895 | A1 * | 7/2004 | Overbeck et al. | 436/180 |

FOREIGN PATENT DOCUMENTS

| | | |
|---|---|---|
| EP | 0815261 | 1/1998 |
| EP | 0868740 | 10/1998 |
| EP | 0901531 | 3/1999 |
| EP | 0914471 | 5/1999 |
| EP | 0937097 | 8/1999 |
| EP | 1164203 | 12/2001 |
| EP | 1262564 | 12/2002 |
| WO | WO96/29431 | 9/1996 |
| WO | WO9737041 | 10/1997 |
| WO | WO9742348 | 11/1997 |
| WO | WO9743617 | 11/1997 |
| WO | WO9812734 | 3/1998 |
| WO | WO9820019 | 5/1998 |
| WO | WO9820020 | 5/1998 |
| WO | WO9820166 | 5/1998 |
| WO | WO9912040 | 3/1999 |
| WO | 9931278 | 6/1999 |
| WO | 9957318 | 11/1999 |
| WO | WO0056446 | 9/2000 |
| WO | WO0060361 | 10/2000 |
| WO | WO0127857 | 4/2001 |
| WO | WO0162966 | 8/2001 |
| WO | WO0204489 | 1/2002 |
| WO | WO0225567 | 3/2002 |
| WO | WO02055199 | 7/2002 |
| WO | WO02059345 | 8/2002 |
| WO | WO02072604 | 9/2002 |
| WO | WO02086794 | 10/2002 |

OTHER PUBLICATIONS

Deng et al., "High-speed gradient parallel liquid chromatography/ tandem mass spectrometry with fully automated sample preparation for bioanalysis: 30 seconds per sample plasma", *Rapid Commun Mass Spectrom.*, 16(11):1116-1123 (2002).

Deng et al., "Multiple-sprayer tandem mass spectrometry with parallel separation for high-throughput quantitation in biological fluids", *Rapid Commun Mass Spectrum.*, 15(17):1634-1640 (2001).

Donovan et al., "Human and mouse dopamine transporter genes: conservation of 5'-flanking sequence elements and gene structures", *Brain Res Mol Brain Res.*, 30(2):327-335 (1995).

Hsueh et al., "QTL influencing blood presure maps to the region of PPH1 on chromosome 2q31-34 in Old Order Amish", *Circulation*, 101(24):2810-2816 (2000).

Lee et al., "Geneome scan for human obesity and linkage to markers in 20q13", *Am J Hum Genet*, 64(1):196-209 (1999).

Reed et al., "A genome-wide scan suggests a locus on chromosome 1q21-q23 contributes to normal variation in plasma cholesterol concentration", *J Mol Med*, 79(5-6):262-269 (2001).

Reed et al., "Localization of a gene for bitter-taste perception to human chromosome 5p15", *Am J Hum Genet.*, 64(5):1478-1480 (1999).

Shockcor et al., "Application of directly coupled LC-NMR-MS to the structural elucidation of metabolites of the HIV-1 reverse-transcritase inhibitor BW935U83", *J Chromatogr B Biomed Sci Appl.*, 748(1):269-279 (2000).

Shockcor et al., "Combined HPLC, NMR spectroscopy, and ion-trap mass spectrometry with application to the detection and characterizationof xenobiotic and endogenous metabolites in human urine", *Anal Chem.*, 68(24):4431-4435 (1996).

Wu et al., "High-speed liquid chromatography/tandem mass spectrometry using a monolithic column for high-throughput bioanalysis", *Rapid Commun Mass Spectrom*, 15(13):1113-1119 (2001).

Wu et al., "Direct plasma sample injection in multiple-component LC-MS-MS assays for high-throughput pharmacokinetic screening", *Anal Chem.*, 72(1):61-67 (2000).

Zheng et al., "The investigation and the use of high flow column-switching LC/MS/MS as high-thoughput approach for direct plasma sample analysis of single and multiple components in pharmacokinetic studies", 27(6):967-982 (2002).

Zheng et al., "Comparison of SPE and fast LC to eliminate mass spectrometric matrix effects from microsomal incubation products", 28(2):279-285 (2002).

* cited by examiner

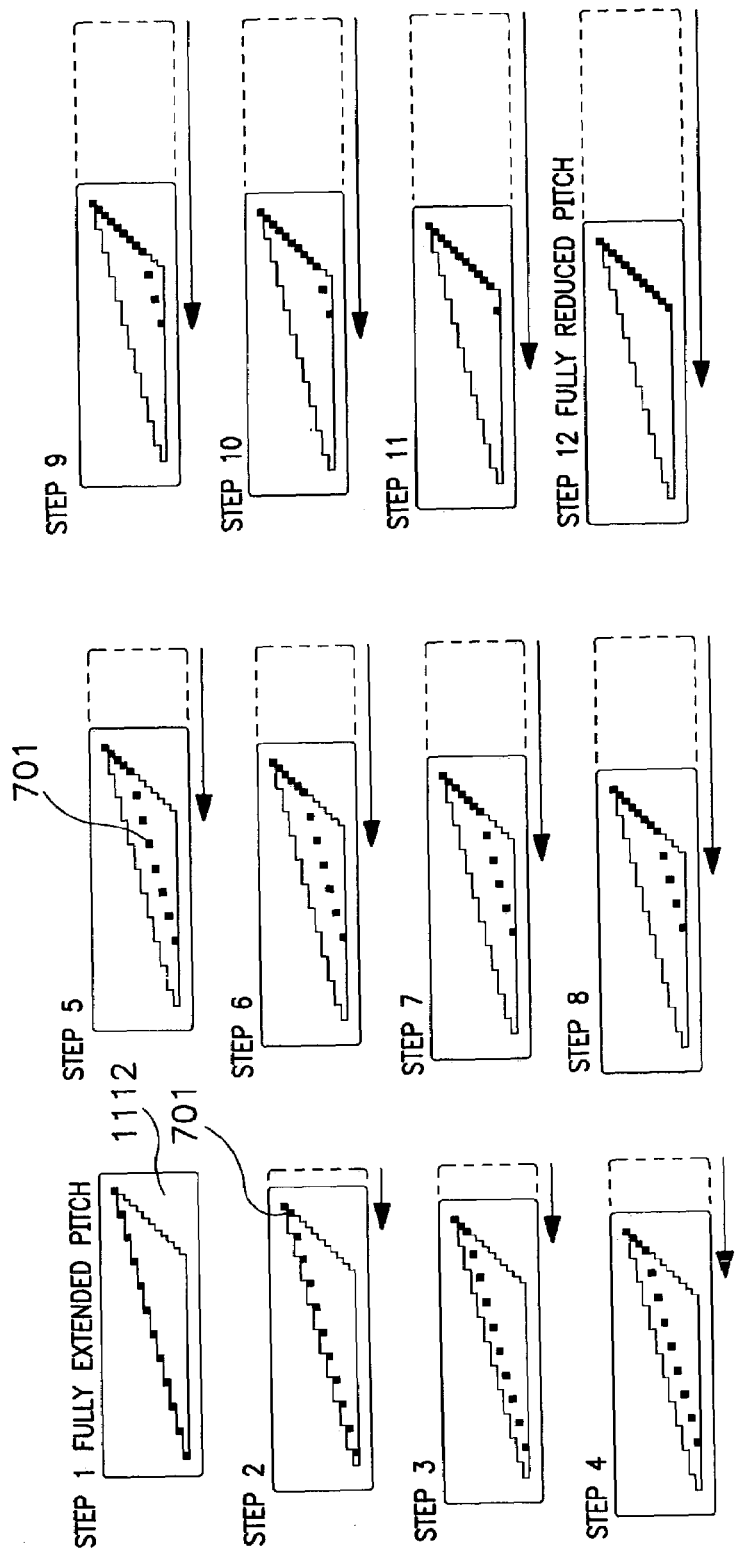

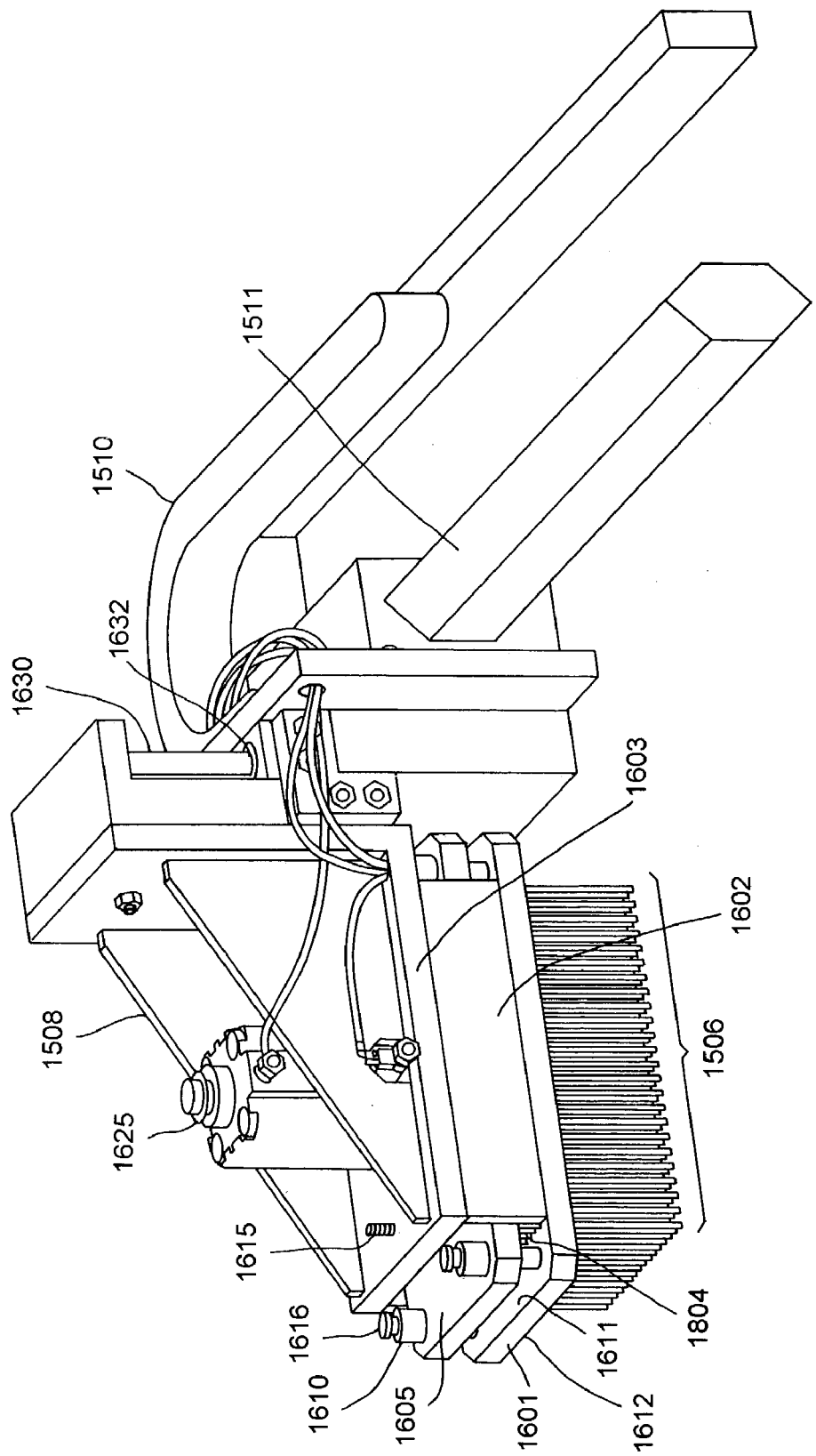

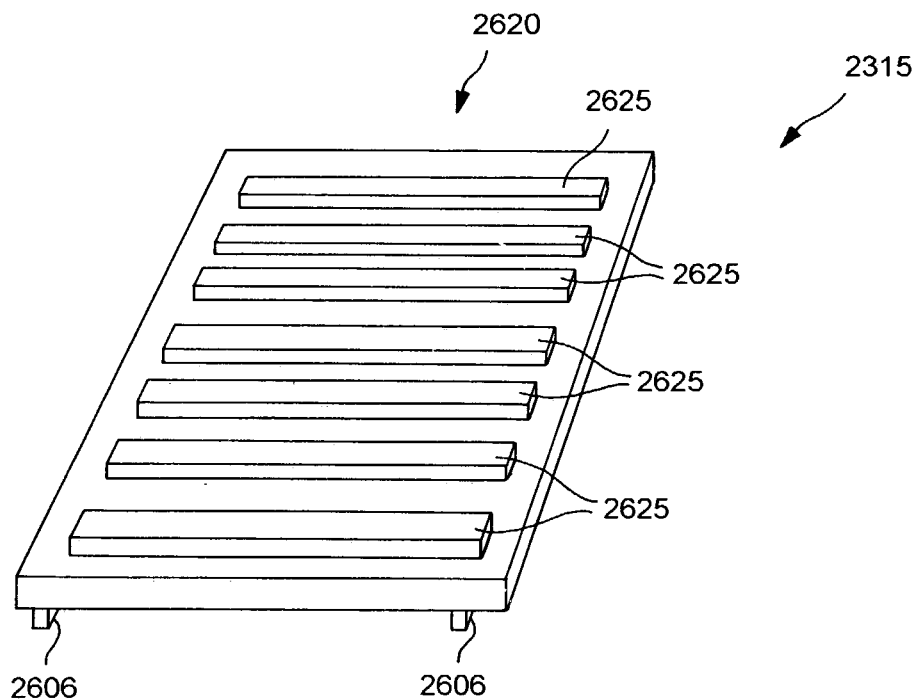
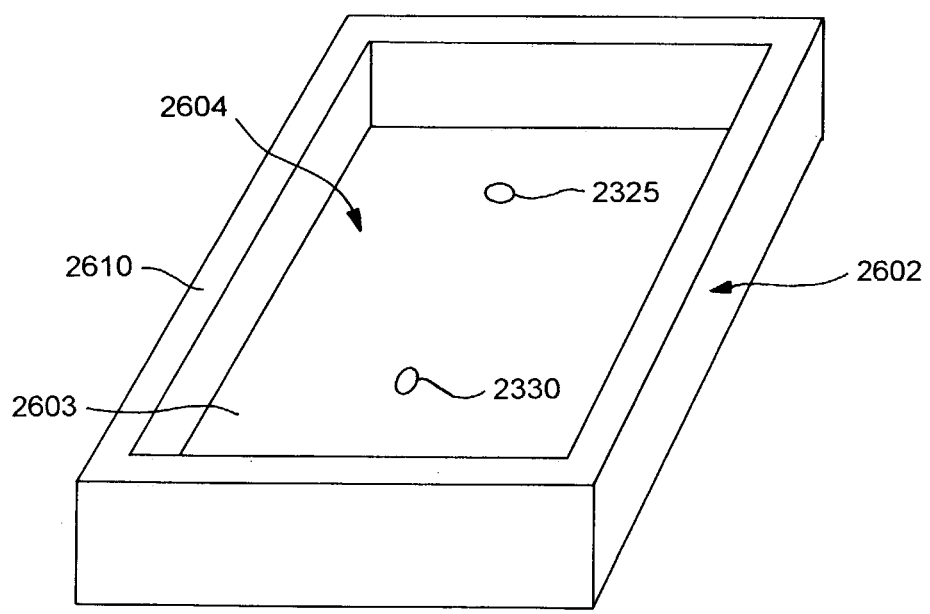
FIG. 27

METHOD AND APPARATUS FOR PARALLEL DISPENSING OF DEFINED VOLUMES OF SOLID PARTICLES

REFERENCE TO PRIORITY DOCUMENTS

This claims priority from U.S. Provisional Application Ser. No. 60/348,745, filed Oct. 26, 2001, and U.S. Provisional Application Ser. No. 60/348,107, also filed Oct. 26, 2001. Both of those applications are incorporated herein by reference in their entirety.

BACKGROUND OF THE INVENTION

1. Field of the Invention

The invention relates to process line systems and, more particularly, to the transfer of materials onto sample plates for laboratory analysis.

2. Description of the Related Art

Processing of biological materials often involves the automated transfer of sample materials onto reaction points for testing and analysis. Automated processing reduces the amount of time necessary to process large numbers of samples. For example, genetic sequencing efforts, such as the Human Genome project, involve processing of large numbers of samples, and have produced vast amounts of information for basic genetic research that have lead to advancements in health care and drug research. With these advances, scientists can move from basic genomic discoveries to associating specific phenotypes and diseases, and thereby better identify targets for drug development. Genetic sequencing involves tests of samples deposited on microarrays, in conjunction with, for example, mass spectrometry testing.

Microarrays have been used to execute tests on large batches of genetic samples to generate phenotype associations and improve interpretation of the large data sets that result from such tests. A typical microarray comprises a substrate on which a large number of reactive points are located. Testing systems typically use a one-inch square array, which is often referred to as a chip. Earlier chips have ninety-six reactive points that receive samples for testing, arranged in a grid of eight points by twelve points. More recently, chips have been produced with four times that capacity, having a 16×24 grid of 384 reactive target locations on the chip substrate. The high capacity microarrays permit the screening of large numbers of samples and can reduce reagent costs because each target location is smaller and therefore requires less reagent to be deposited for testing.

Samples are usually prepared in a sample material plate, such as a multiple-well tray called a microtiter plate (MTP). A variety of liquid reagent materials are combined in the wells and are subjected to various heating and mixing cycles. The sample preparation typically begins with empty MTPs being delivered to a processing station. The various reagents and biological materials are then added. Some of the sample processing may involve heating, cooling, and mixing of the ingredients and biological materials while in the wells of the MTP. Many high-throughput systems involve computer controlled robotic arms that pick up the MTPs, rotate, and place each MTP at the next processing station. In this way, each MTP is moved along in the sample preparation process. Some stations may take more time to complete than others, thereby creating a bottleneck that hinders increased throughput.

Typically, completed MTPs reach a processing station where the biological samples are delivered to the chip target locations, using pins that are dipped into the sample material, which loads the tip of the pin. The loaded pin is then touched to a target area on the substrate, so that the sample liquid is transferred to the target by contact deposition. Pin tools can be problematic for high throughput systems because the pins themselves may have to be changed if different sample volumes are desired, or if the nature of the liquid sample is changed.

High-throughput testing systems typically use an array of pin tools to transfer the samples onto the chip target locations. A grid of pin tools is mounted on a dispensing head, which is lowered over a multiple-well microtiter plate (MTP) at a loading station so all of the pin tools in the array are simultaneously dipped into a respective well and, when the dispensing head is withdrawn, all the pin tools are loaded with biological samples, or reagents. Thus, with one downward cycle, all the pin tools are loaded with a sample material. The dispensing head is then withdrawn from the MTP, and then lowered over a sample chip. The sample material is then transferred to the target locations on the chip by contact deposition, which is also referred to as printing.

It should be apparent that, with ninety-six (or even 384) target locations in a one-inch square area, alignment of the dispensing head with the chip is very important to the accurate delivery of samples to the target locations. Increases in the throughput of biological samples in an efficient manner requires increasing the number of pins, thereby reducing the number of load-and-print cycles, and also requires very quick alignment of the dispensing head over the chip, and also requires rapid movement from the MTP loading station to the chip.

The dispensing head with an array of pins (i.e., a block of pins) is usually aligned to a predetermined position relative to the location at which the chips will be delivered for printing. The alignment process is typically a manual process that is performed at the beginning of a processing run, such as at the beginning of a work day. Because the block is in a fixed position relative to the dispensing head, the alignment of the head to the chips should ensure that all of the pins are aligned to the target locations on a chip. Each time the processing is halted, however, a manual alignment must be performed again to ensure proper alignment and accurate placement of the pins over the chips.

A processing run may involve thousands of load-and-print dispensing head cycles. It may be necessary to halt a processing run, such as when it becomes desirable to change or replace pins or the pin block during a processing run, or when the run must be halted for a mechanical failure or to check alignment. This causes a disruption in operation because, to ensure accurate transfer, another manual alignment must be performed before proceeding with the processing run.

The alignment process after a change in pins or a changed pin block may be especially important because the new pins may be offset from the previously installed pins, relative to the dispensing head. Thus, if no check of alignment with the new pins is performed, the pin tips may make contact with the chip at different locations from before, even though the alignment of the dispensing head to the chip has not changed, or even if the dispensing head alignment has been checked and confirmed. The samples will not be accurately transferred to the target locations on the chip. Thus, changing pins or pin blocks results in not only a delay because of the alignment process, but also results in a more complicated alignment process, further slowing down the system throughput. Although current systems are capable of processing tens of thousands of samples in a day, even higher throughput systems are desired. It should be apparent that current alignment techniques cannot easily support the demands of high-throughput systems.

The wells on a MTP often contain sample materials that are themselves the result of several operations, usually involving the mixing of solutions and other processing in each of the wells, to prepare the sample materials. Therefore, the wells must have minimum dimensions to physically permit the sample preparation operations to occur. For a 384-well MTP, the wells are typically spaced apart at approximately 4.5 mm between well centers. In contrast, the target locations on a chip are typically arranged at the minimal spacing distance that can avoid sample contamination on the chip, typically at approximately 1.125 mm between target location centers, although other spacings may be used. Thus, the 384 wells on a MTP must be spaced farther apart than the 384 wells on a chip.

In a typical system, the pins of the dispensing head are arranged in the same spacing as the wells of the MTP, to permit insertion into the MTP wells and loading of the pin tips. It should be apparent that not all of the target locations on a chip can receive their samples at the same time, given the differential spacing of the pins. Therefore, systems stagger the delivery of sample material with repeated cycles of loading and printing with the pins in a dispensing head.

For example, in the spacing described above, the target locations are at a spacing that is one-fourth the spacing of the pins in a block. Therefore, for a chip having 384 target locations, a dispensing head having a 24-pin array of pins in a block must be loaded and printed through sixteen cycles of the dispensing head. It would also be necessary to perform a wash and rinse cycle of the pin block, to prevent contamination, between each loading and printing. It often can require upwards of twelve minutes to complete the loading and printing for a 384-target chip. Even a lower capacity 96-target chip would require four dispensing head cycles, which would require several minutes to complete.

Therefore, to print on all the target locations with a conventional 24-pin block, the dispensing head must load the pin block and print onto a first set of twenty-four target locations such that every fourth target location along one dimension on the chip is printed (e.g., first, fifth, ninth, and thirteenth column locations). Along the other dimension, the rows, six target locations will be printed, comprising first row, seventh, thirteenth, and so forth. The pin block must then be washed, rinsed, and loaded for the next printing cycle, during which the 24-pin block is positioned over a second group of target locations, offset or staggered from the first group, so that the second group may comprise target locations at the second, sixth, tenth, and fourteenth columns, as well as corresponding row locations.

After the second group is printed, another wash, rinse, and load cycle is repeated and then the third dispensing head cycle prints the third, seventh, eleventh, and fifteenth column of target locations, and then the fourth cycle prints the target locations for the fourth, eighth, twelfth, and sixteenth columns. In this example, the next dispensing head cycle would print in columns 17, 21, 25, and 29, followed by columns 18, 22, 26, 30, and so forth, repeating the dispensing head cycles until all wells of the 384-well chip are printed. It should be apparent that the current staggered printing operation can be a bottleneck to increasing the throughput of sample handling systems.

As noted above, samples are usually prepared in multiple-well trays called microtiter plates (MTPs). A variety of reagent materials are combined in the wells and are subjected to various heating and mixing cycles. The sample preparation typically beings with empty MTPs being delivered to a processing station. The various reagents and biological materials are then added. Some of the sample processing may involve heating, cooling, and mixing of the ingredients and biological materials while in the wells of an MTP. Many high-throughput systems involve computer controlled robotic arms that pick up the MTPs, rotate, and place each MTP at the next processing station. In this way, each MTP is moved along in the sample preparation process. Some stations may take more time to complete than others, thereby creating a bottleneck that hinders increased throughput.

Some of the reagent material may comprise a suspension of liquid and particles mixed together. It is important for the suspensions to have good mixing of liquid and particles, or solid matter, to ensure proper reactions in the MTP wells. This requirement can make working with suspension for MTP wells difficult to work with, because it may be difficult to keep the suspension adequately mixed and agitated without damaging the particles from excessive mixing and agitation. That is, suspension mixtures can be very unstable and it can be difficult to maintain them in a sufficiently suspended state.

An alternative to using a suspension mixture is to keep the particles separate from the liquid until the suspension mixture is needed. When it is necessary to mix the particles (which are typically in the form of a powder), the particles are deposited into wells of a dry particle tray, where each particle well has a predetermined volume according to the laboratory process being performed. Any excess particle material that is mounded over the top of any particle well is scraped off the top surface of the tray and into a particle reservoir. The particle tray is then quickly inverted over the microtiter plate so that the contents of each particle well fall into a corresponding well of the microtiter plate. The particle tray can be tamped with a solid object to dislodge any remaining portions of particle matter, ensuring that the proper volume of particle matter is delivered, and then the liquid and particle contents in each MTP well can be mixed to form the required suspension.

Maintaining ingredients in powder form can be advantageous, because the solid particles have greater stability and shelf life than a corresponding suspension would have, and keeping the materials in the solid state avoids the problem of keeping the suspension agitated, but the particle mixing operation described can be an excessively manual process. There is a continuing need for high-throughput biological processing systems. Such systems are becoming increasingly automated, with processing for tens of thousands of samples each working day. The manual processing associated with keeping solid particle material out of suspension until needed becomes a bottleneck to increased throughput. It should be apparent that there is a need for improved techniques for providing the suspension in MTP wells at the required time during processing of sample materials, to provide greater stability of material, reduce concerns regarding handling of suspension, and improve compatibility with increased automation systems.

Another stumbling block to increasing throughput is the requirement for some systems to perform temperature bath, referred to as thermal cycling. In a typical thermal cycling operation, an MTP plate is placed on top of a metal plate that conforms to the underside of the MTP. The temperature of the metal plate is controlled through cooling and heating cycles, as desired, thereby affecting the contents of the MTP wells. For high-throughput systems, it is important to ensure greater heat transfer rates for faster sample processing. It is also important to achieve greater uniformity of temperature cycling to ensure highly reproducible biological reactions giving clinically validated results.

Thus, there is a need for improved techniques for alignment of pins to target locations, for printing between MTP wells of one spacing to target locations at a different spacing that support higher throughput rates, for particle dispensing, and for thermal cycling operations to support increased throughput rates. The present invention fulfills this need.

SUMMARY

A sample preparation system constructed in accordance with the invention provides an automated process that dispenses appropriate amounts of solid material into wells of a microtiter plate for mixing into a suspension. The system utilizes an array of hollow tubes that are lowered into a particle reservoir such that particle material is forced up into the tubes. During loading, solid plungers in the tubes are positioned a known distance from the open end of the tubes. When the particle material is to be dispensed, the plungers are lowered to push the particle material out of the tubes and into receiving wells of the microtiter plate. The plunger stroke and internal diameter of the tubes defines the dispensed volume of particle material. This ensures that predefined volumes of particle material are accurately delivered to each well. Particle material can be kept in a solid form until needed in suspension, thereby increasing stability and shelf life. The operation can be performed by an automated process under computer control. This supports highly automated, high-throughput systems for processing biological samples.

In one particularly innovative aspect, the invention is directed toward a solid reagent dispensing station. The station includes an array of hollow tubes, and each of the tubes has a plunger slideably inserted therein. The array is connected to a transport mechanism, which includes a guide rail. The array is coupled to the guide rail, which can be configured to transport the array along a Y axis. The station also includes a reservoir containing a bed of solid reagent particles. The reservoir is sized to receive the array of hollow tubes. A conveyor for transporting MTPs through the station can also be included.

The transport mechanism transports the array from a point of origin, along a Y axis, to a point of destination just over the reservoir. There, the array can be lowered along a Z axis into the reservoir, causing particles of solid reagent to be forced into the hollow tubes. The array is then raised and transported by the transport mechanism along the Y axis back to its point of origin. The point of origin can be above the conveyor, which can be carrying an MTP. At this point, the plungers in the hollow tubes can be forced or pushed downward causing the particles of solid reagent in the hollow tubes to be pushed out into the wells of the MTP.

In another particularly innovative aspect the invention is directed to an apparatus for dispensing particle material into wells of an MTP. The apparatus includes a first plate having a top surface and a bottom surface and an array of holes bored through the plate leading from the top surface to the bottom surface. An array of hollow tubes is coupled to the bottom surface of the plate and aligned with the array of bored holes. The apparatus includes a second plate with a top surface and a bottom surface. The second plate rests on springs, which in turn rest on the top surface of the first plate. An array of plungers protrudes from the bottom surface of the second plate. The first and second plates are aligned so that the array of plungers are aligned with the array of bored holes. The plungers are inserted into the holes and extend into the hollow tubes. The hollow tubes can be of equal lengths or different lengths, and the plungers can also be of equal lengths or different lengths. The top surface of the first plate and the bottom surface of the second plate are separated from each other by the springs. One or more stop posts, preferably four, are used to connect and align the first and second plates to one another.

BRIEF DESCRIPTION OF THE DRAWINGS

FIG. 16 is a sequence of schematic representations showing the pin block of FIG. 11 as it is changed from the fully extended pitch to the fully reduced pitch.

FIG. 18A is a perspective view of the resin dispensing assembly of the resin dispensing module of FIG. 17A.

FIG. 27 shows a perspective view of an exploded flow cell assembly of a microtiter plate assembly.

DETAILED DESCRIPTION

Unless defined otherwise, all technical and scientific terms used herein have the same meaning as is commonly understood by one of skill in the art to which this invention belongs. All patents, patent applications, published applications and publications, Genbank sequences, Websites, and other published material referred to throughout the entire disclosure herein are, unless noted otherwise, incorporated by reference in their entirety.

Figure 1:
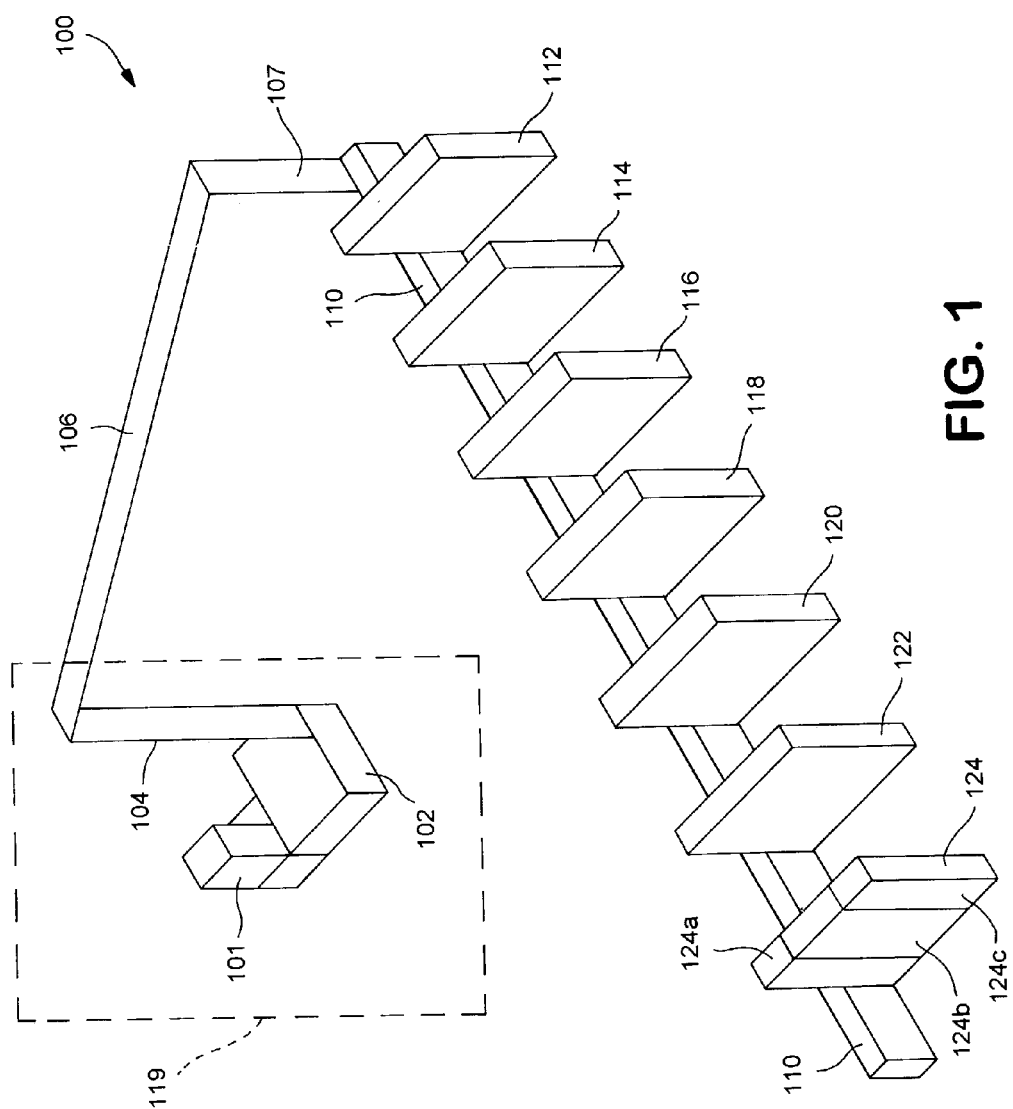
FIG. 1 shows a process line system constructed in accordance with the present invention.

FIG. 1 shows a computer controlled process line 100 that is constructed in accordance with the present invention. The line is sometimes referred to as an Automated Processing System 100, and is controlled by a computer system 101 that keeps track of microtiter plates (MTPs) as they move along the process line. The computer system 101 also controls processing of the MTPs as the MTPs move through various process line modules and work stations. The computer system 101 can be used to specify particular modules that the MTPs will be directed to as the process line 100 transports the MTPs. The process line 100 includes a plurality of modules or workstations 112, 114, 116, 118, 120, 122, and 124 that are connected by a conveyor line 110. As described below, the conveyor line 110 can be used to transport an MTP to all or some of the modules, where various procedures or processes can be performed on biological samples of the MTP.

A module or station whose processing follows that of a prior process will be referred to as being "downstream" of the prior process. As will be described further below, the control system of the process line permits a modular configuration that enables extension of the process line by inserting new modules before, after, or in between any of the modules described herein, and also enables extension of the process line by adding more stations at any one of the modules, so that a module that performs a specified processing task may have a greater or lesser number of stations that perform that same task, changing in number as the processing needs require. Thus, it should be appreciated that the process line 100 shown in FIG. 1 is merely exemplary with respect to the quantity of modules, and that the process line 100 could include additional modules or less modules. Furthermore, the process line 100 can include modules where processes other than those described herein can be performed.

In the exemplary embodiment shown in FIG. 1, the modules of the process line 100 include an introduction module 102, where an MTP can be loaded onto the process line. The introduction module 102 can be used to perform various set-up procedures on the MTP in order to prepare the MTP for processing in the other modules. The introduction module 102, as well as other exemplary modules of the process line 100, are described in more detail below. The introduction module 102 is connected to a lift 104 that can upwardly transport the MTP to a bridge 106 that leads to the remainder of the process line 100. The bridge connects to a second lift 107 that downwardly transports the MTP to the conveyor line 110, which can transport the MTP to the other modules of the process line 100. The conveyor line 110, bridge 106, and lifts 104, 107 include a transport mechanism, such as a conveyor belt, that can support an MTP and move the MTP to each of the modules of the process line 100.

The lift 104 and bridge 106 permit independent movement of personnel around the MTP introduction module 102 and the processing stations that are downstream of the bridge 106. This permits different personnel to access the first station 102 as compared with the rest of the process line 100. In addition, the bridge 106 spatially separates the introduction module 102 from the remainder of the process line 100, permitting the use of different materials and maintenance for the two different sections of the process line. Thus, the module 102 can be environmentally isolated from the rest of the process line 100, as described in more detail below, in order to overcome any potential risk of sample cross-contamination.

The processing line can move MTPs along the modules so that MTP processing is not entirely sequential or simply batch processing. That is, MTPs are received at the first module 102 for processing and are then moved from module to module, but an MTP can be moved from one module to the next as soon as the MTP has completed its processing, so that an MTP does not necessarily move from one module to the next in the exact same sequence that the MTPs were received at the introductory module 102. Thus, modules that take a greater amount of time to process a single MTP may be provided with multiple work stations, such that multiple MTPs may be processed at that module. It should be understood that any one of the modules 112, 114, 116, 118, 120, 122, 124 may include multiple work stations. That is, each module performs a specified operation or task associated with biological or chemical processing of sample materials, and each module may include one or more work stations, each of which performs the operations or tasks associated with the module. An MTP can bypass a module completely if no processing at that module is needed for that MTP. This increases throughput and increases the efficiency of the process line 100.

Figure 2:
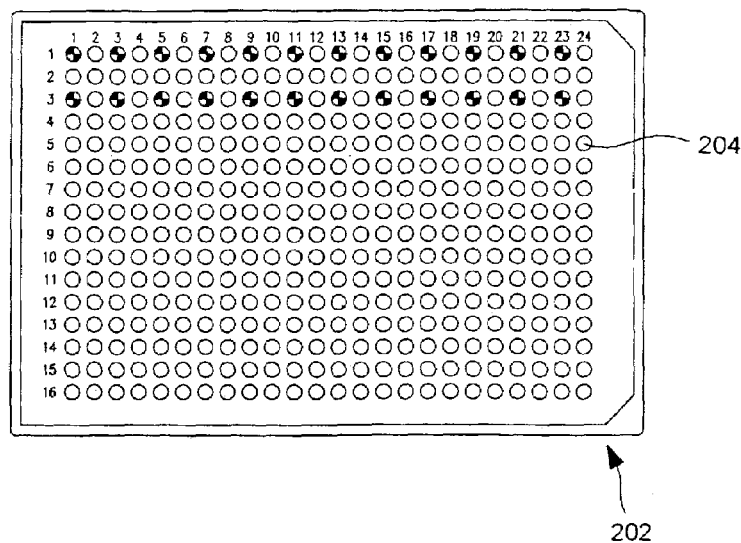
FIG. 2 is a top view of a microtiter plate that is moved along the process line system illustrated in FIG. 1.

FIG. 2 shows a top, plan view of a microtiter plate 202 such as can be processed by the process line. FIG. 2 shows the MTP 202 as a high capacity plate that contains three hundred eighty-four wells 204, arranged in a grid of sixteen wells by twenty-four wells. Those skilled in the art will understand that MTPs with other capacities are also available, such as the commonly used ninety-six well MTP, which has wells arranged in eight rows of twelve wells each.

Process Overview

The process line 100 comprises a fully integrated continuous biological processing operation that utilizes combinations of microtiter plates and microtiter plate-sized chip holders to process and transport biological samples and materials. The process line 100 utilizes a thermal-cycling device and procedure, described below, which reduce processing time over conventional thermal cyclers. The process line also utilizes a nanoliter dispensing device having a dispensing system that can be used with microtiter plates and chips of different sizes. In addition, the process line uses a resin dispensing device and method that permits the addition of dry particulates to an MTP in a rapid manner. The aforementioned devices are described below in more detail.

As discussed above, biological reactions are conducted in plastic microtiter plates (MTP). The standard commercially available MTPs have are of 96-well or 384-well configuration, while it is anticipated that future versions will be of 1536-well configuration. The process line 100 is configured to accept MTPs of any format. For example, the process line 100 can process MTPs that conform to the Mass EXTEND (hME™) protocol, which has been developed by Sequenom, Inc. of San Diego, Calif. Such MTPs are referred to herein as EXTEND Cocktail plates. A microtiter plate is set-up at the beginning of the process line by a robotic arm and microfluidic dispensing equipment, which are located at the module 102.

An MTP, such as an MTP containing DNA samples, is set up at the introduction module 102 and is used to amplify specific target regions of genomic or plasmid DNA contained in the wells of the MTP. The same MTP can be used for all subsequent reactions in the process line 100. At a final module of the process line 100, the products of these reactions are transferred to one or more microarray chips suitable for conducting mass spectroscopic analysis. The MTPs are initially prepared by depositing combinations of DNA samples, region-specific amplification oligonucleotides, and appropriate amplification enzymes and buffers into wells of the MTPs. The MTPs are preferably identified with a magnetic or optical bar code symbol, sealed and passed into an amplification module of the process line, where a process such as PCR is performed. The introduction module 102 can also be used to prepare "EXTEND Cocktail" plates, which contain all appropriate reagents, nucleotide triphosphates, enzymes and oligonucleotides necessary to conduct the prescribed genotyping analysis.

The computer system 101 includes tracking software that can be used to define and keep track of the nature of all MTPs introduced into the introduction module 102. The tracking software can also be used to specify the process line modules that the MTPs must be transferred to and how the contents of the MTPs will be subsequently used or processed. The bar code of each plate is tracked throughout the progress of the plate through the process line.

A process line operator can operate the computer 101 that controls operation of the process line 100. The computer 101 can receive from the operator operating parameters, commands, and other input that will determine the processing of MTPs contained in the process line. In general, preparing the line 100 for operation involves some preliminary analysis to obtain the optimal operating configuration. The following is an overview of the information and data flow used in controlling operation through the computer 101.

An operator begins by entering experimental design parameters through a software interface program executing in the computer 101. In one embodiment, the software interface comprises a Laboratory Information Management System (LIMS) which is a software interface program manufactured by Sequenom, Inc. of San Diego, Calif., to determine the assays that will go on which sample plates. The software can keep track of the contents of MTPs using bar codes that are associated with each MTP. The operator can initially coordinate the bar code of an MTP to the contents and processes of the MTP using the computer 101. For example, barcodes of plates, primers, reagents, hotel plate/reagent holder locations, and module stops, can be read into the software during set-up, such as using a conventional bar code reader that is coupled to the computer system 101. The software can also obtain data from the modules of the process line 100 as the MTPs are transported through the process line. The software is configured to create a daily task list for the operator.

The software creates a work list file for the set-up platform 102. The work list can contain, for example MTP set-up information, such as data regarding the barcode for an MTP and information regarding the modules that the MTP will visit while on the conveyor line 110. The computer system accepts user inputs that define which modules a particular MTP will be transported to on the process line 100, as well as which modules will be bypassed. Based on the user inputs, the computer system adjusts the movement of the MTP along the process line so that the MTP is transported to only those modules that are to handle the biological sample contained in the MTP, and so that the MTP bypasses any module that should not handle the biological sample.

The Process Line

The process line 100 is configured to conduct a plurality of biological reactions. In one embodiment, the process line 100 conducts over 100,000 individual biological reactions per day and is readily scaleable to 1,000,000 reactions per day. In another embodiment, the process line 100 conducts over 200,000 individual biological reactions per day. Thus, when used in conjunction with MTPs having a 384-well configuration, the process line 100 can process up to 520 MTPs per day where there are 200,000 individual biological reactions per day and up to 140 MTPs per day where there are 200,000 individual biological reactions per day. The configuration is sometimes described herein in the context of implementing analysis of Single Nucleotide Polymorphisms (SNPs) using the homogeneous Mass EXTEND(hME™) protocol, which has been developed by Sequenom, Inc. of San Diego, Calif. Other configurations using the same unit operations but in different combinations are possible and these will enable other nucleic acid based analyses.

Figure 3:
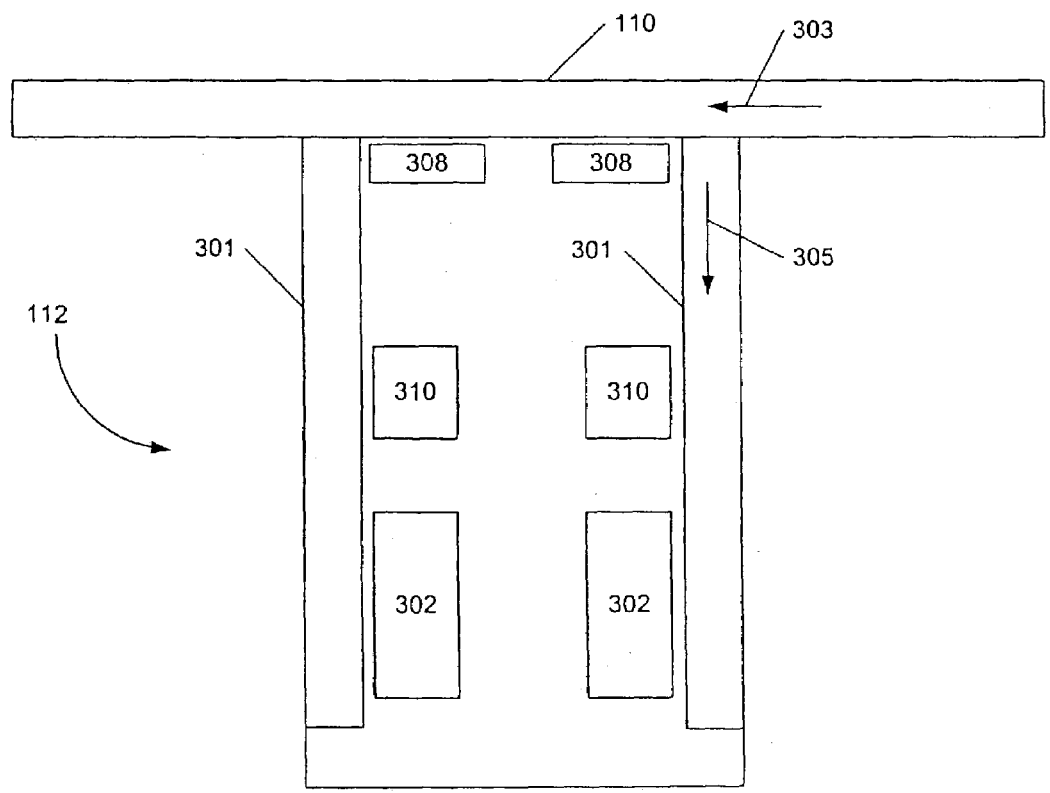
FIG. 3 shows a schematic top view of an exemplary module of the FIG. 1 process line system.

As mentioned, the process line 100 includes a plurality of modules where one or more processes can be performed on an MTP that has been loaded onto the process line 100. An exemplary module 112 is now described with reference to FIG. 3, which shows a schematic top view of the generic module 112. The module 112 includes one or more module conveyor lines 301, which are situated transverse to the main conveyor line 110. Each module conveyor line 301 accepts an MTP from the main conveyor line 110 and transports the MTP to one or more workstations 302 that are situated along the module conveyor line 301. For example, the MTP can be transported along the main conveyor line 110 in a direction represented by the arrow labeled 303. The MTP can then be moved to the module conveyor line 301 at the location where the main conveyor line 110 meets the module conveyor line 301. The module conveyor line 301 can transport the MTP to a workstation 302 along a direction represented by the arrow 305. As described below, the workstation 302 can comprise a device that performs an automated process on the MTP or on the samples that are contained in the wells of the MTP. FIG. 3 shows a single workstation 302 situated along each module conveyor line 301, although it should be appreciated that the module 112 can include any number of workstations 302.

Thus, as mentioned above, it should be understood that any one of the modules 112, 114, 116, 118, 120,122, 124 may include multiple work stations. That is, each module performs a specified operation or task associated with biological or chemical processing of sample materials, and each module may include one or more stations, each of which performs the operations or tasks associated with the module. For example, as shown in FIG. 1, the last module 124 includes stations designated as 124a, 124b, 124c to indicate, for example, that multiple water addition, resin mixing, and chip printing stations are provided.

As mentioned, the MTPs are fitted with one or more barcodes that can be utilized to identify the MTP, such as to identify the contents of the MTP or the procedures to be performed on the MTP. The barcodes can also be used to sort data that is associated with each MTP. Thus, the module 112 can have a conventional barcode reader 308 that is located at the entrance to each module, as schematically shown in FIG. 3. In addition, each module can include a weight measuring device, such as a balance 310, that can be used to measure the weight of each MTP that enters the module. The balance 310 can be used to measure the weight of the MTP before and after processes have been performed on the MTPs in order to identify a difference in weight of the MTP. A difference in weight could indicate, for example, whether excessive evaporation has occurred during thermal processes or whether required reagents have not been added to the MTP. The weight measurement at a particular module can also be used as a reference for future measurements and calculations.

Exemplary Modules

An overview of several exemplary modules that can be used in the process line 100 is now provided. As shown in FIG. 1, the introduction module 102 is situated at the beginning of the process line 100. The introduction module 102 is used to initially insert an MTP onto the process line 100. In this regard, the process line 100 can include a transport, such as a conveyor belt or a track, that runs the length of the process line, such as along the length of the lift 104, bridge 106, lift 107, and conveyor line 110. The MTP is placed on the conveyor at the introduction module 102. The introduction module 102 can include a device that seals the wells of the MTP, such as by using an aluminum film. Once the MTP has been placed on the conveyor belt, an operator can use a user interface on the computer system 101 to notify the process line 100 that the MTP is ready for processing.

The introduction module 102 can be used to prepare and distribute materials to the MTP. For example, the sample material can be a cocktail that has been or will be subject to a reaction process, such as the Polymerase Chain Reaction (PCR) or to some other reaction process, such as the "MassEXTEND" reaction process, which is a DNA Polymerase extension reaction where the oligonucleotide primer is extended through the diagnostic region of interest by several bases. A particular MTP can be selected for use with the introduction module 102.

With reference to FIG. 1, the lift 104 transports the MTP from the module 102 in an upward direction to the bridge 106. The bridge then transports the MTP to the second lift 107, which then lowers the MTP to the conveyor line 110. In one embodiment, the introduction module 102 is contained within a clean room 119 (represented by a dashed box in FIG. 1) that separates the introduction module 102 from the rest of the process line 100. The clean room 119 can be sealed, for example, with an airlock to prevent contamination from entering the clean room 119.

After the lift 104, bridge 106, and lift 107 have transported the MTP from the introduction module 102, the conveyor line 110 receives the MTP from the lift 107. The conveyor line 110 then successively transports the MTP to one or more of the modules along the process line 100. In an exemplary embodiment, the modules are arranged in the order described herein, although it should be understood that modules may be added and deleted while still permitting efficient operation under control of the computer system 101.

The module 112 is not used for any particular processes in the described embodiment. Rather, module 112 serves as a "virtual" module in that the module can be used for future expansion. This illustrates the advantageous modularity of the process line 100, in that modules can be added, deleted, left empty, expanded or reduced, without affecting the operation of other modules in the line.

Module 114 follows module 112 along the process line 110. Module 114 comprises an amplification module that includes a thermal cycling work station that can be used to thermal cycle the contents of the MTP, such as pursuant to a PCR process. The module 114 (or any of the other modules) can receive multiple MTPs so that the thermal cycle process can be performed in parallel in order to increase input. The module 114 can include a device comprised of a centrifuge for spinning the MTPs before and after the thermal cycling to ensure all solutions in the MTPs are concentrated at the bottom of each well and so are suitable for fluidic handling. As mentioned, the MTPs can be weighed prior and subsequent to thermal cycling to ensure that no evaporation or leakage has occurred. If a difference in weight of more than a certain threshold weight is detected, the progress of that specific plate can be diverted to the end of the process line 100 and the user or tracking software notified.

With reference again to FIG. 1, the next module in the process line is the module 116, where a reagent, such as Shrimp Alkaline Phosphatase (SAP), is dispensed into the wells of the MTP. Prior to dispensing the reagent, a workstation of the module 116 unseals the aluminum seal from the MTP to expose the wells of the MTP. The reagent is then added to all reaction wells in all plates, such as to destroy any unreacted nucleotide triphosphates in the wells. SAP is a common reagent that can be dispensed using an array of solenoid valves linked to a common reservoir of reagent which is temperature controlled for maximum shelf-life.

With reference to FIG. 1, the next module in the process line 100 is the module 118, which is an incubation module. At the module 118, the MTP is subjected to an incubation process, such as for SAP incubation, if SAP was added at the previous module 116. The incubation module 118 includes one or more workstations that facilitate the incubation process, such as a thermal cycling unit for SAP incubation and subsequent heat inactivation. The module 118 can also include a centrifuge for spinning the MTP after thermal incubation of the MTP. The module 118 can also include a workstation that applies a seal to the MTP, such as a polypropylene seal, that covers the wells of the MTP.

The next module is the module 120, which is the module where an "EXTEND" cocktail is added to the MTP, if required. The module 120 includes a workstation comprised of a peeling unit, which removes the polypropylene seal from the MTP. The module 120 can also include a workstation comprised of a cooler that cools the MTP. In certain embodiments, the module 120 also includes a workstation comprised of a second peeling unit for removal of the aluminum seal, if present, from the MTP. The module 120 can also include additional workstations, such as a syringe array (such as a 384-syringe array) for rapid parallel transfer of "EXTEND" cocktail from an "EXTEND" plate to a PCR reaction plate. The module 120 can also include a buffer position indicator for active "EXTEND" plate if used for multiple PCR plates and a wash station for washing the MTP. A waste container can also be provided at the module 120.

The next module is the module 122, which is a module where an "EXTEND" reaction is performed, as well as resin dispensing is performed. An exemplary resin dispenser device is described in more detail below. As in some of the previous modules, the module 122 can include workstations comprised of a centrifuge, a seal applicator for sealing the MTP, a thermal cycler for conducting an EXTEND reaction, and a peeling unit to remove polypropylene seal from the MTP after the EXTEND reaction.

With reference still to FIG. 1, the next module is the module 124, where water addition, resin mixing, and chip printing is performed. The module 124 can include a workstation comprised of a water dispenser that can be used to dispense water to the MTP. In one embodiment, a 16-fold solenoid valve manifold is fed from temperature-controlled reservoirs to dispense water. The module 124 also includes a workstation comprised of a centrifuge for spinning plates after water addition and prior to nanoliter transfer of samples from the MTP to a chip. An in-line resin mixing station can also be deployed at the module 124, as well as a device that dispenses samples from the MTP to a chip.

The computer system 101 controls the flow of plates from the conveyor line 110 into the module 124 to one of the work stations 124a, 124b, 124c and then back out to the conveyor line 110 again. The transfer of the plate from the conveyor line 110 to the module 124 can be accomplished using a suitable transfer mechanism, such as a transverse conveyor belt that is oriented transverse to the direction of the conveyor line 110. When the plates encounter the transverse conveyor belt, the plates are directed toward the module where appropriate. Similar control abilities are implemented by the computer system for each of the other modules of the line 100.

Pin Alignment

As noted above, a sample delivery system constructed in accordance with the invention aligns a pin array dispensing head to target locations of a substrate, such as a chip, and automatically determines any offset in pin alignment relative to the dispensing head for successive blocks of pins. As used herein, "substrate" refers to an insoluble support that can provide a surface on which or over which a reaction may be conducted and/or a reaction product can be retained. Support can be fabricated from virtually any insoluble or solid material. For example, silica gel, glass (e.g. controlled-pore glass (CPG)), nylon, Wang resin, Merrifield resin, Sephadex, Sepharose, cellulose, a metal surface (e.g. steel, gold, silver, aluminum, silicon and copper), a plastic material (e.g., polyethylene, polypropylene, polyamide, polyester, polyvinylidenedifluoride (PVDF)). Exemplary substrates include, but are not limited to flat supports such as glass fiber filters, glass surfaces, metal surfaces (steel, gold, silver, aluminum, copper and silicon), and plastic materials. The solid support is in any desired form, including, but not limited to: a plate, membrane, wafer, a wafer with pits and other geometries and forms known to those of skill in the art. Preferred support are flat surfaces designed to receive or link samples at discrete loci. Most preferred as flat surfaces with hydrophobic regions surrounding hydrophilic loci for receiving, containing or binding a sample.

Figure 4:
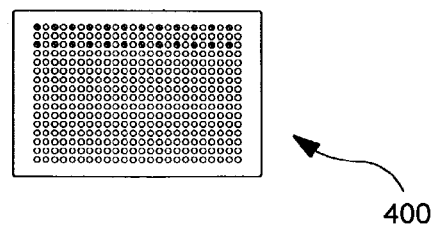
FIG. 4 is a detail top view of a chip, comprising a substrate with reaction target deposits that will receive sample material from the microtiter plate illustrated in FIG. 2.
Figure 5:
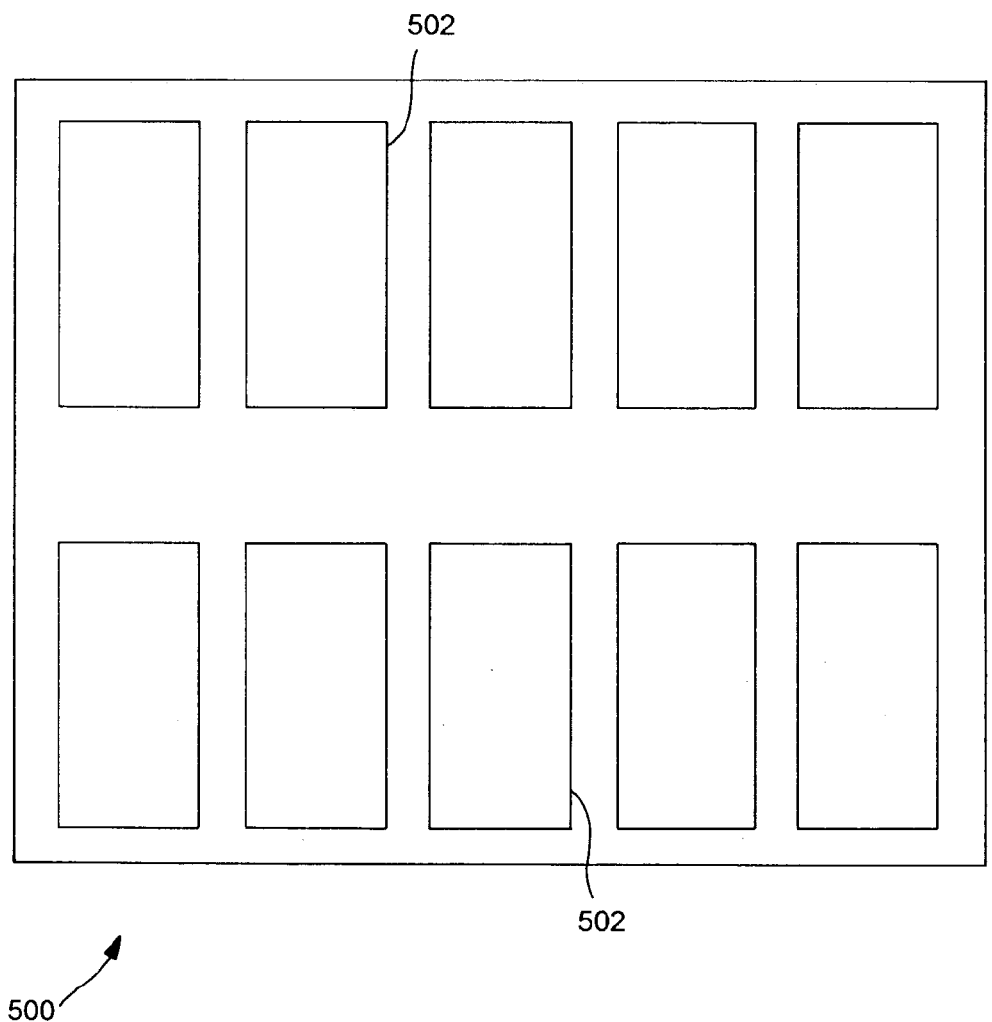
FIG. 5 is a top view of a multiple-chip holder, containing ten chips of the type illustrated in FIG. 4.

FIG. 4 shows an exemplary substrate comprising a chip 400 having an array of target locations onto which sample materials will be deposited during a printing process that takes place in the last module 124. The chip illustrated in FIG. 4 includes three hundred eighty-four target locations, arranged into a 16×24 grid. For easier and more efficient handling, a group of chips can be collected together and placed on a carrier tray. FIG. 5 shows a carrier tray 500 that may accommodate up to ten chips. The carrier tray 500 includes a plurality of recessed chip holders 502 that can each receive a chip 400. The chip holders 502 are arranged into two rows, with five chip holders per row.

Figure 6:
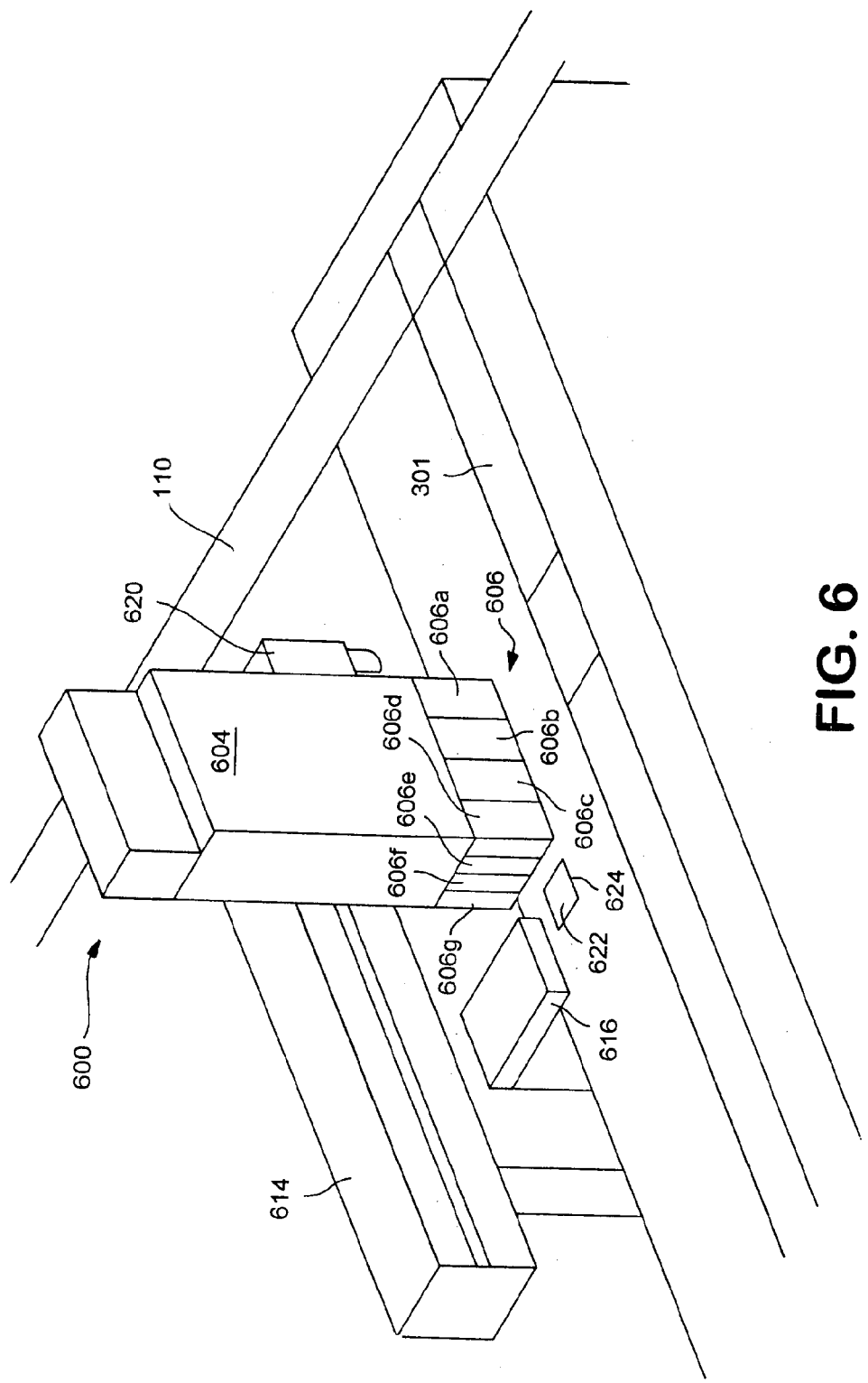
FIG. 6 is a perspective view of a treatment station of the FIG. 1 process line at which sample transfer from microtiter plates to chips takes place.

FIG. 6 shows a perspective view of the module 124 of the process line 100. As was discussed above, chip printing is performed at the module 124. Thus, the module 124 includes at least one work station comprised of a delivery system or chip printing station 600. The chip printing station 600 includes a movable dispensing head 604 that includes at least one pin array 606. Each pin array includes a plurality of dispensing pins that can be dipped into the wells of an MTP so that the pins can aspirate material from the wells. The pins of the pin array can then be used to print the material onto a chip. In this regard, the chip printing station 600 also includes a loading station 616 where chips can presented for loading of materials by the dispensing head 604.

The dispensing head illustrated in FIG. 6 includes sixteen arrays or blocks of pins, of which only the outermost 606a, 606b, 606c, 606d, 606e, 606f, 606g are visible in FIG. 6 (a reference to "606" without a letter suffix will be understood to be a reference to the collection of all sixteen pin blocks generally, rather than to a particular pin block). In one embodiment, each array contains a block of twenty-four pins (in a 4×6 array), for a total of 384 pins in the dispensing head 604. It should be appreciated, however, that the quantity and spatial arrangement of the pins can vary. Each pin array 606 can be removed from the dispensing head and replaced by a replacement array 606.

All of the sixteen pin arrays in the dispensing head 604 can be dipped into the MTP wells (such as a 384-well MTP) for aspirating sample material in the wells. The sample-loaded pins can dispense the sample material onto the chip one pin array at a time with the determined pitch in the MTP-to-chip reformatting process described below. In addition, less than all of the sixteen pin arrays 606 can be dipped into less than all of the wells of the MTP for aspirating sample material from the wells. The pin arrays can then dispense sample material onto the chip one pin array at a time with the determined pitch or shift distance in the MTP-to-chip dispensing and reformatting process. The aspiration of the remaining MTP wells can then be performed in order to complete the dispensing and reformatting process from the entire MTP wells onto the chip. The one-step sample material aspiration with multiple pin arrays, coupled with individual pin array printing onto the chip, can eliminate the time-consuming steps for pin array washing, cleansing, and drying. Thus, the throughput of the process is maximized as a result.

Figure 7:
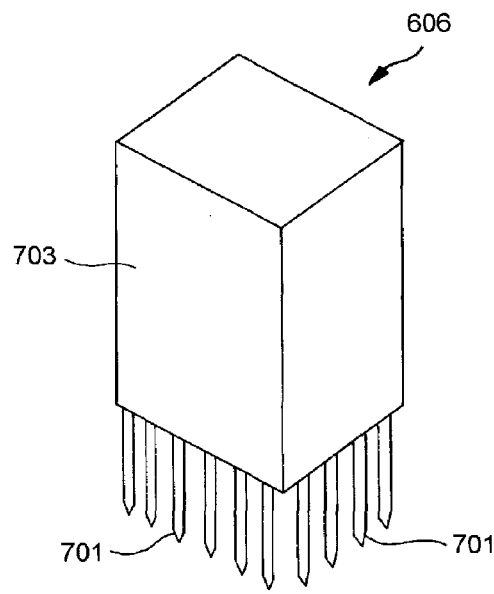
FIG. 7 is a perspective view of a pin array of the treatment station shown in FIG. 6.

FIG. 7 shows a perspective view of a single pin array 606. The pin array 606 of FIG. 7 includes a plurality of dispensing pins 701, wherein each pin is configured to dispense a material in a well known manner. The pins 701 are mounted in a pin block 703. As mentioned, the dispensing pins are arranged in a rectangular array. In one embodiment, the array includes four rows of pins, with each row containing six pins. The pins 701 are positioned so that each pin can be aligned with a corresponding target location on a chip that is positioned below the pin array.

With reference again to FIG. 6, the chip printing station 600 is positioned adjacent a module conveyor line 301 for the module 124. The module conveyor line 301 is used to transport MTPs from the main conveyor line 110 to the chip printing station 600. MTPs proceed along the main conveyor line 110 and, when appropriate, are directed into the chip printing station 600 by the computer system 101. The direction of the MTPs into the chip printing station may be accomplished, for example, by utilizing the bar code of the MTP. The bar code can contain information that directs the computer system 101 to forward a particular MTP to the chip printing station 600, such as when the MTP reaches the module 124 as the MTP moves along the conveyor line 110. It should be understood that only one chip printing station is illustrated in FIG. 6 for simplicity of presentation, and that the station illustrated in FIG. 6 can include multiple stations.

With reference still to FIG. 6, the dispensing head 604 is mounted to a transport mechanism 614, such a track, that moves the dispensing head in a direction parallel to the module conveyor line 301 and also perpendicular to the module conveyor line 301. Thus, the transport mechanism 614 can be used to properly align the pins of the dispensing head 604 to the target locations of a chip onto which material will be printed. As described previously, alignment between the pins of the dispensing head 604 and the target locations of the chips is important for achieving accurate and valid testing results. In accordance with the invention, proper alignment is achieved with a two-camera vision system that can identify and compensate for any misalignment between the dispensing head and the chip, and between the pins and the dispensing head. The system is thereby unaffected by the misalignment that might otherwise occur, even after the dispensing head has been aligned to a chip.

The vision alignment technique of the process line 100 involves a chip alignment camera comprising a downward-looking camera 620 mounted to the side of the dispensing head 604 so that the downward-looking camera 620 is located in a fixed position relative to the dispensing head 604, as shown in FIG. 6. The camera 620 is oriented so the camera 620 can look down onto the top surface of a chip that is positioned below the camera 620. Thus, the target locations of the chip will be in the camera field of view. The vision alignment technique also involves a pin alignment camera comprising an upward-looking camera 622 that is mounted below the module conveyor line 301. The upward-looking camera 622 is positioned so that it has a field of view that includes the pins of the dispensing head 604. The downward-looking camera 620 ensures that, when the dispensing head is moved to a chip printing position, it is properly positioned above a chip for the pins with which it is initially loaded and calibrated. As is conventional, a calibration sequence is performed to ensure proper registration of the pins to the target locations at an initial process run. Thus, once the pin arrays 606 are mounted to the dispensing head, there should be no concern of misalignment between the pins and chip target locations. In a conventional system, any change in pins presents an opportunity for pin-dispensing head misalignment to occur.

The present invention solves the problem of pin-dispensing head misalignment by using the second camera 622 to check for any change in location of the pins relative to the dispensing head 604 whenever the pins are changed, such as when a pin array 606 is replaced. The second camera 622 looks up at the dispensing head 604 through a glass reference plate 624 that is located in the field of view of the second camera 622. The pins of the dispensing head 604 are visible through a pin alignment reticle on the glass reference plate 624 and in the field of view of the camera 622. The position of a new block of pins on the dispensing head 604 can be compared to the position of a prior block of pins, known to be calibrated to delivery at the chip target locations, by noting any change in pin position relative to the reticle, which is fixed relative to the camera 622 and pins.

Figure 8:
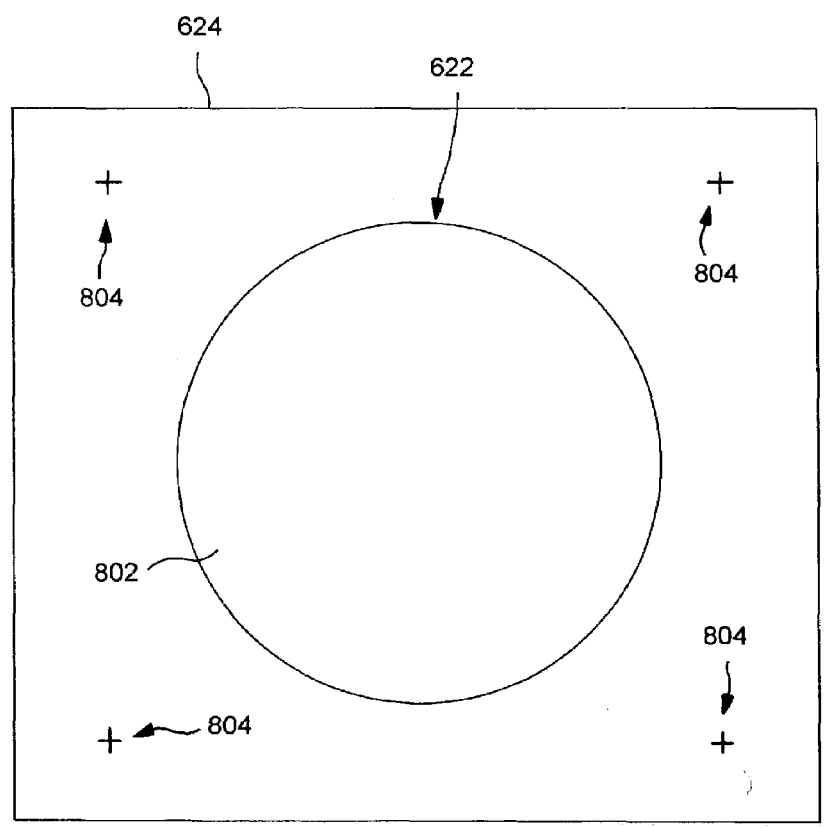
FIG. 8 is a view looking down through the reference plate illustrated in FIG. 6, showing the lens of the upward-looking camera.

FIG. 8 shows a view down through the glass reference plate 624 illustrated in FIG. 6, looking down at the upward-looking camera lens 802 of the camera 622. In FIG. 8, the pin alignment reticle comprises a series of "+" index marks 804, wherein one index mark is placed in each corner of the glass reference plate 624. Those skilled in the art will recognize that many different index marks may be used as a reticle for pin alignment. All that is needed is to create a background pattern against which the computer system may make a comparison of relative pin position.

Figure 9A:
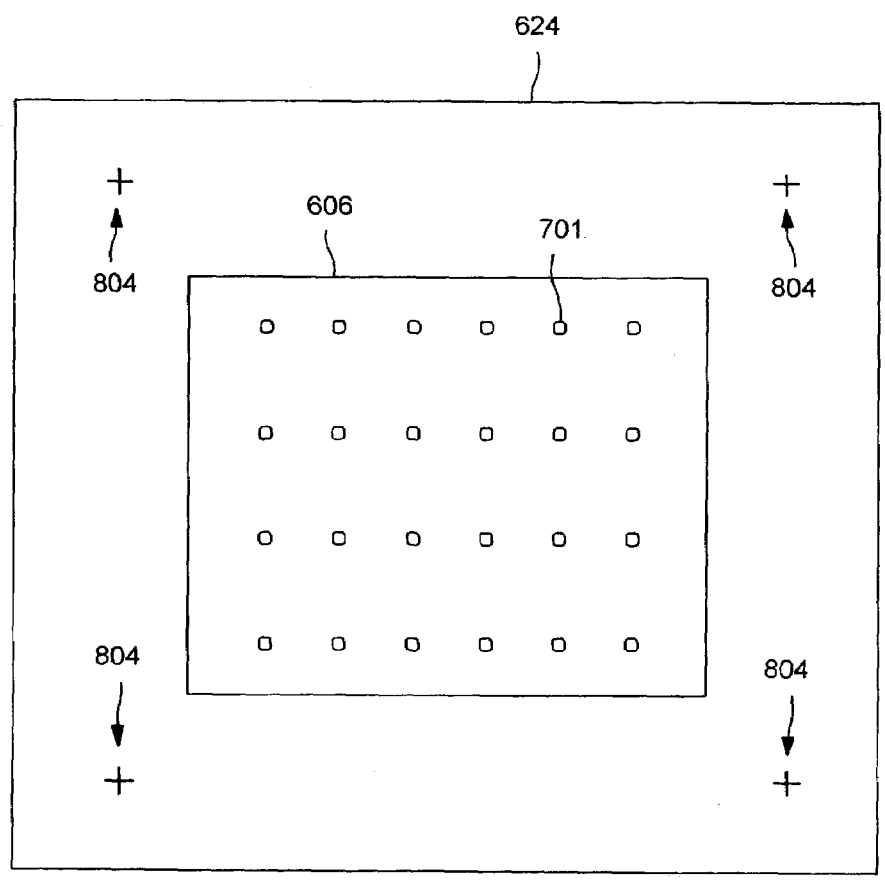
FIG. 9A is a view looking up through the reference plate and observing the underside of the dispensing head illustrated in FIG. 6.

FIG. 9A shows a view from the perspective of the upward-looking camera 622, looking up through the reference plate 624 such that the reticle index marks "+" 804 are visible. The camera 622 also has a view of the underside of a pin array 606 (the bottom tips of the pins 701 in the pin array are represented as rectangles in FIG. 9A). When an array of pins is replaced by a new pin array, the position of the replaced pin tips relative to the index marks 704 may be different from the position of the previous array of pin tips relative to the index marks. The computer system 101 can detect such a difference in position by comparing a digital image of the original pin configuration with a digital image of the replacement pin array, as seen through the reference plate 624.

The computer system 101, when it detects a change in position between a replaced array of pins and a new array of pins, may provide a signal to the operator and may halt operation of the chip printing station 600, waiting for instruction or operator action. Alternatively, the computer system 101 can automatically identify and compensate for the direction and magnitude of misalignment, through the aforementioned digital image comparison technique. For example, the computer system 101 can send instructions to the transport mechanism 614 to cause the transport mechanism 614 to move the dispensing head 604 in order to compensate for the misalignment.

Figure 9B:
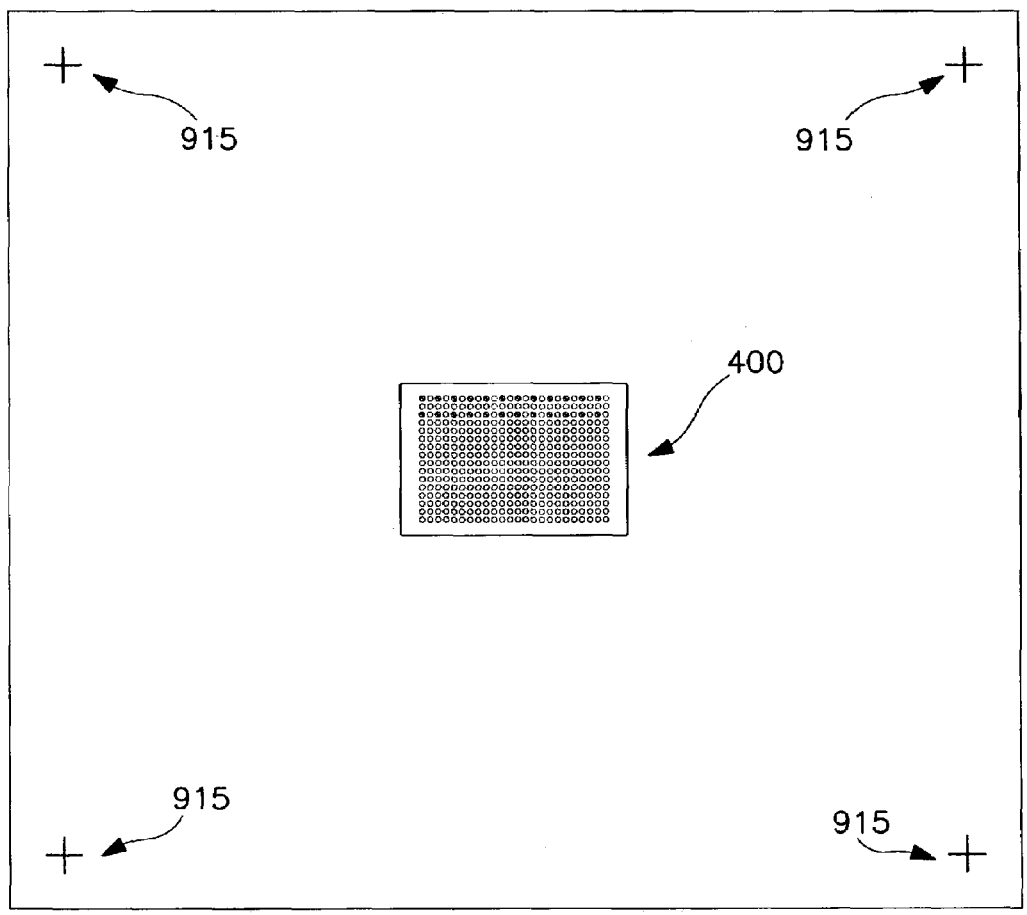
FIG. 9B is a view from the perspective of the downward-looking camera illustrated in FIG. 6, looking down at a chip that is positioned below the camera and the dispensing head.

FIG. 9B shows a view from the perspective of the downward-looking camera 620, looking down at a chip 400 that is positioned below the camera and the dispensing head 604. The field of view of the downward camera includes chip alignment reticles 915 that are fixedly positioned in the field of view of the downward-looking camera 620. The reticles 915 can be used to relatively locate index marks on the chip 400. Because the reticles 915 are fixedly located in the camera 620 field of view and the camera 620 is fixedly located relative to the dispensing head 604, the relative location between the chip index marks and the reticles 915 is an indication of the relative location between the chip 400 and the dispensing head.

Figure 10:
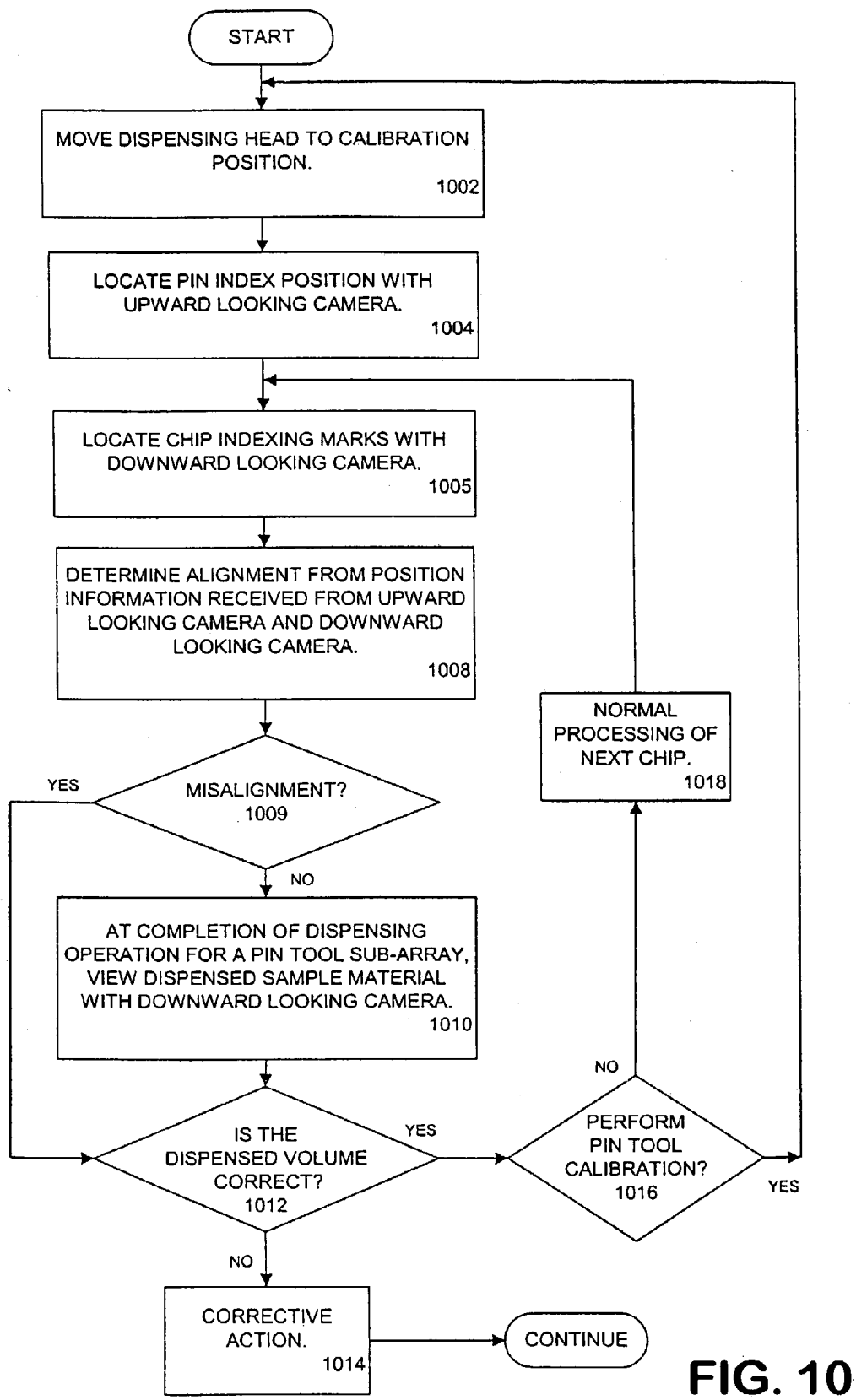
FIG. 10 is a flow diagram that shows the alignment process for the system illustrated in FIG. 1.

The flow diagram of FIG. 10 illustrates the operation sequence of the process line 100 in accordance with the two-camera alignment checking. In the first processing operation, represented by the flow diagram box numbered 1002, the dispensing head 604 is moved to a calibration position. The exact location of this calibration position will depend on the particular installation of machinery at the chip printing station 600, but will generally involve moving the dispensing head to a known location above a particular chip of a chip tray that is located at the loading station 616. Those skilled in the art will understand how to determine a suitable calibration position and procedure for the system.

In the next operation, at block 1004 of FIG. 10, the dispensing head 604 is moved so the upward-looking camera 624 can view the pins and can locate a pin index position. This may comprise, as illustrated in FIG. 9, moving the dispensing head 604 so the pin arrays 606 provide a camera image in which the positions of the pin tips relative to the pin reticle in the camera field of view are substantially constant. Those skilled in the art will understand commonly used digital image processing techniques that can be used to make comparison between the digital images of the pin configurations, and will understand how to identify misalignment.

At block 1005, the downward-looking camera 622 is used to locate indexing marks on a chip. The indexing marks may comprise any indicia that appear in the camera field of view that may be useful in proper positioning (calibration) of the camera relative to the target locations. The index marks, for example, can comprise the target locations themselves. In one embodiment, the calibration image does not involve index marks that fill the camera field of view, but involves an edge of a chip. This provides a digital image that is more easily compared for relative change from prior images, to more readily show subtle changes in relative position.

At block 1008, the alignment of the pin arrays to the dispensing head 604 and of the dispensing head 604 to the chips is determined from the upward and downward-looking cameras, respectively. The upward looking camera view is usually needed only when the pins or pin arrays are changed. It should not be necessary to perform the upward looking pin calibration process during processing if there is no change in pins or in the pin blocks, as it would be unlikely that the position of the pins relative to the dispensing head has changed. Preferably, the downward-looking calibration will be utilized with every positioning of the dispensing head 604 over a chip for printing. If any camera view indicates a misalignment, an affirmative outcome at the decision block 1009, the computer system 101 will take corrective action. A misalignment can be between the dispensing head and the chip or between the pins of the dispensing head and the dispensing head. A misalignment between the dispensing head and the chip is present where the relative locations between the chip index marks and the chip alignment reticle have changed between a current image and a previous image. A misalignment between the pins and the dispensing head is present where the relative locations between the pins and the pin alignment reticle have changed between a current image and a previous image.

The corrective action, indicated at block 1014, may comprise halting operation of the process line, providing a message to the operator, or automatically providing adjustment to operation, such as by adjusting the position of the pins or the dispensing head. For example, if the image from the downward-looking camera 620 indicates that the dispensing head is misaligned with respect to the original calibration position, then the dispensing head can be moved to re-align the dispensing head. If the image from the upward looking camera 622 indicates that any of the pins are misaligned relative to the index marks 804, then the misaligned pins can be repositioned on the dispensing head. In any event, the corrective action to be taken will depend on the needs of the particular process line installation. If no corrective action is needed, then the system continues processing and prints sample material to a chip.

The downward camera 620 may be optionally used to check the volume of sample material being deposited on the target locations. To accomplish this checking, after a chip has been printed, the dispensing head 604 is moved to the downward-looking calibration position after a chip has been printed, as indicated at block 1010 (which results from a negative outcome at block 1009). At the decision box numbered 1012, the computer system determines if the size of the sample spot on the chip falls within a tolerance range for correct volumes of sample. If the size of the spot indicates an incorrect volume, then at block 1014 the system takes corrective action.

The corrective action may comprise halting operation of the process line, or it may involve sending a message, or otherwise flagging the affected chip(s) for later disposal. In one embodiment, the computer system 101 automatically checks the volume of dispensed material on the chip, determines if an adjustment to delivered volume should be made, and automatically makes the adjustment.

If the dispensed volume is within tolerance, an affirmative outcome at block 1012, then a calibration is performed at regular intervals of printing cycles, to ensure greater accuracy and operation within limits. The system checks (at block 1016) to determine if a pin calibration should be performed. Block 1016 indicates that the system computer knows the interval at which calibration should be performed, and in one embodiment the system will query or prompt the system operator, or will automatically proceed with calibration at the proper time. Calibration is performed by returning to block 1002. If a calibration check of the pin relative to the dispensing head is not called for, a negative outcome at block 1016, then processing proceeds with normal processing of the next chip at the station, indicated at block 1018, whereupon the dispensing head calibration to the next chip is performed at block 1006 and the other operations repeat.

It should be noted that other configurations of vision assisted alignment may be implemented without departing from the teachings of the present invention. For example, a single viewing camera may be utilized, in conjunction with mirror reflection, to perform the alignment operations described above. The FIG. 6 configuration, for example, may be modified so that the reference plate 622 is replaced with a mirror, such that the only the downward-looking camera 620 is needed. When the upward view is required, observing the underside of the pin array, the downward-looking camera will be positioned over the mirror reference plate 622 to make an observation about the pin alignment. The reticle marks of the reference plate will be printed on the top surface of the mirror, so proper alignment checking may be performed. This configuration eliminates the need for two camera viewing systems.

Pin Array Reformatting

As noted above, a sample process line 100 constructed in accordance with the present invention reformats a pin array of a dispensing head to ensure that the spacing of the pin array at printing is reduced from the pitch at sample loading, preferably a multiple of the spacing of the target locations of a chip, in at least one dimension (reformatting in multiple dimensions may also be performed). In the system 100 illustrated in FIG. 1, the spacing of the pins at sample loading time is an integral multiple of the wells. For example, at sample loading time, the MTP wells have a spacing of one well every 4.5 mm, while the pin array block has a spacing of one pin every 9.0 mm. This initial spacing provides quick and efficient loading of the pins in the wells. In accordance with the invention, the spacing of the pin array within a block is then reduced at printing time to more nearly match the spacing of the chip target locations along two rows at a time. This reformatting of the pin array reduces the number of staggered printing actuations needed for the dispensing head. Thus, a greater number of pins may be arranged in a pin block, because the reduction in pin array pitch at printing permits more pins per actuation to be printed to target locations. For example, with pair-wise reformatting of all the rows of the pin array, the number of pins in a block can be four times greater, and the number of staggered dispensing actuations can be reduced by one-fourth.

Figure 11:
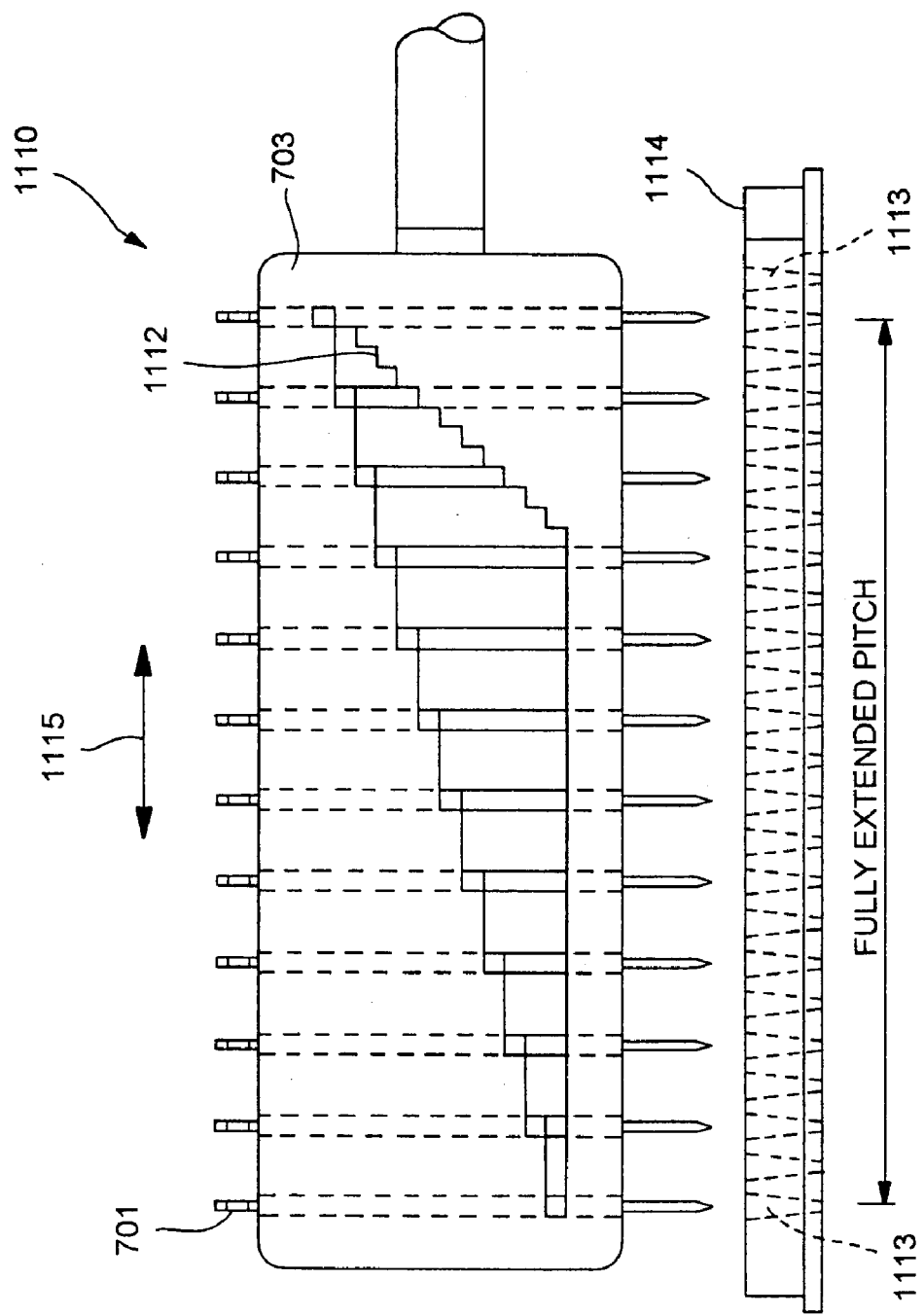
FIG. 11 is a side view of a pin block illustrated in FIG. 5, showing the pins at fully extended pitch.
Figure 12:
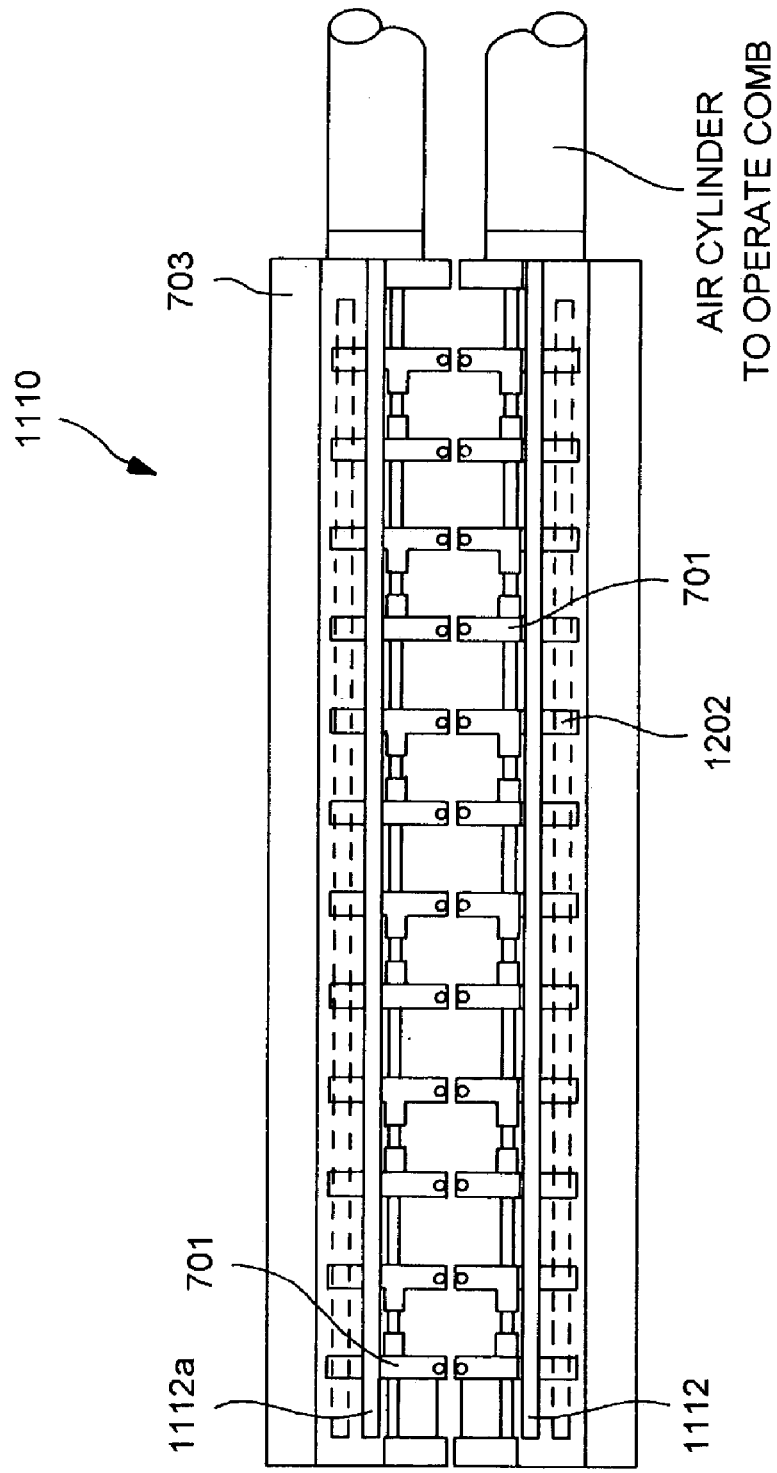
FIG. 12 is a top view of the pin configuration illustrated in FIG. 11.

FIG. 11 is a side view of a pin array 1110 having at least one row of pins 701 that are movably positioned. For comparison purposes, FIG. 11 also shows a side view of an MTP 1112 below the pin array 110. The MTP 1112 includes a plurality of wells 1113. FIG. 12 shows a top view of the pin array 1110, showing two rows of pins 701. The pin block 703 includes a pitch changing comb 1112 that can engage protrusions 1202 (shown in FIG. 12) on each of the pins 701. As described below, the pitch changing comb 1112 can be moved laterally (as exhibited by the directional arrow 1115 in FIG. 11) to reformat the pitch of the pins 701. Thus, the pins 701 can be moved between a fully extended pitch (wherein the pin pitch is largest, as shown in FIGS. 11, 12) and a fully-reduced pitch (wherein the pin pitch is smallest, as shown in FIGS. 13, 14).

In one embodiment, the pitch of the MTP wells is one well every 4.5 mm, while the pitch of the pin array is one pin tip every 9.0 mm. Thus, as shown in FIG. 11, at the fully extended pitch, there is a pin 701 aligned with every other well 1113 of the MTP 1114.

Figure 13:
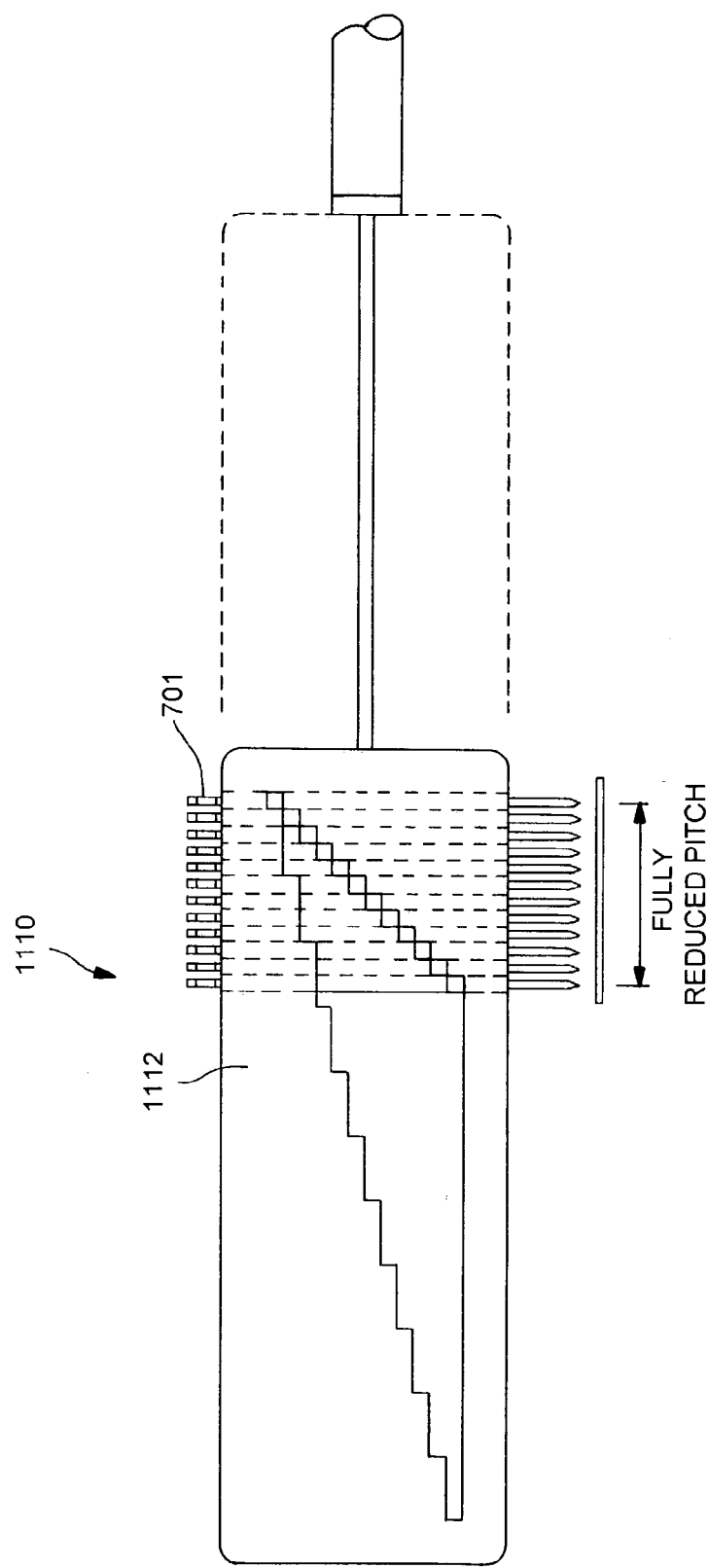
FIG. 13 is a side view of the pin block illustrated in FIG. 11, showing the pins at their fully reduced pitch.
Figure 14:
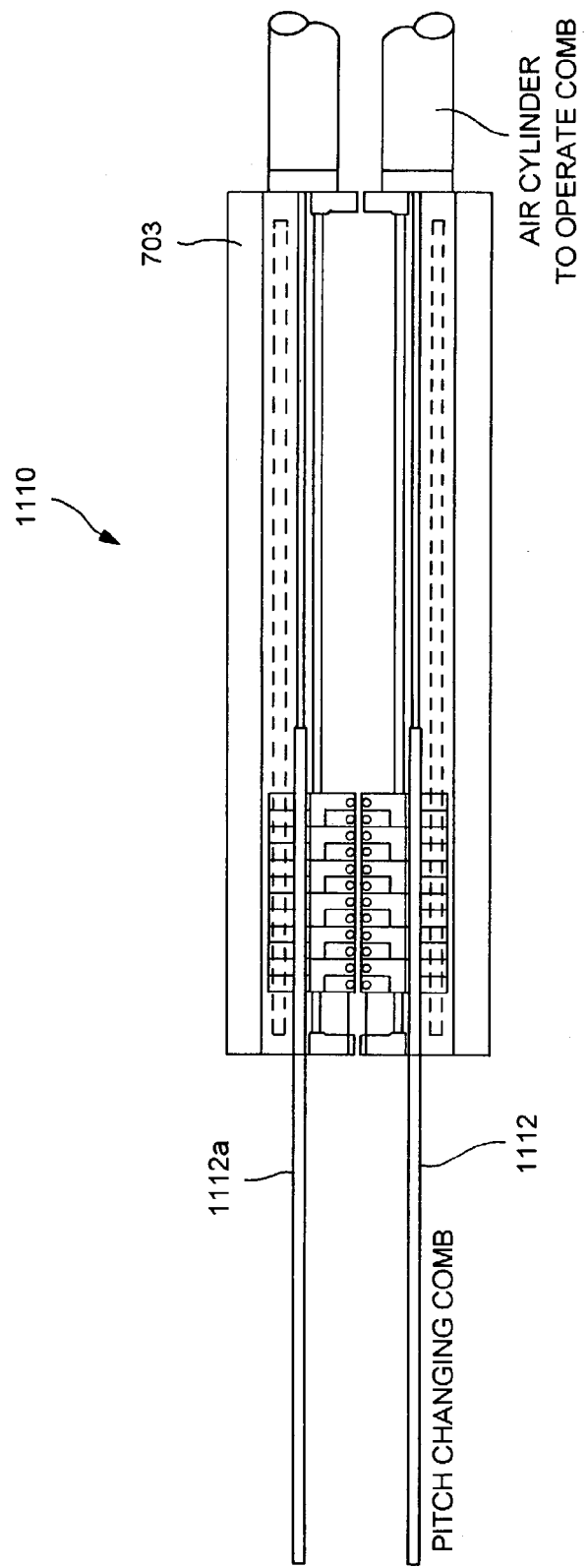
FIG. 14 is a top view of the pin configuration illustrated in FIG. 11.

FIG. 13 is a side view of the pin array 1110 at the fully reduced pitch, from the same perspective as FIG. 11, while FIG. 14 is a top view of the pin array 1110 at the fully reduced pitch, from the same perspective as FIG. 12. In one embodiment, the pitch of the pin array 1110 in FIG. 13 and FIG. 14 is one pin tip every 2.25 mm, which is a reduced pitch from the fully extended configuration and is more nearly the same pitch as the target locations on a chip. This permits the dispensing head 604 to be constructed with four times the number of pins as before, because the reformatting permits more pins to be engaged in printing at the same time. Reformatting from a pitch of 9.0 mm to 2.25 mm (compare FIG. 11 and FIG. 12 with FIG. 13 and FIG. 14) permits the same dispensing head blocks to be used with 384-well chips and also with 96-well chips (a 96-well chip has target locations at a spacing of 2.25 mm, a 384-well chip has a target location spacing of 1.125 mm). Thus, with reformatting from 9.0 mm to 2.25 mm, the number of staggered printing operations that are needed to print at the target locations is reduced by one-fourth.

Figure 15:
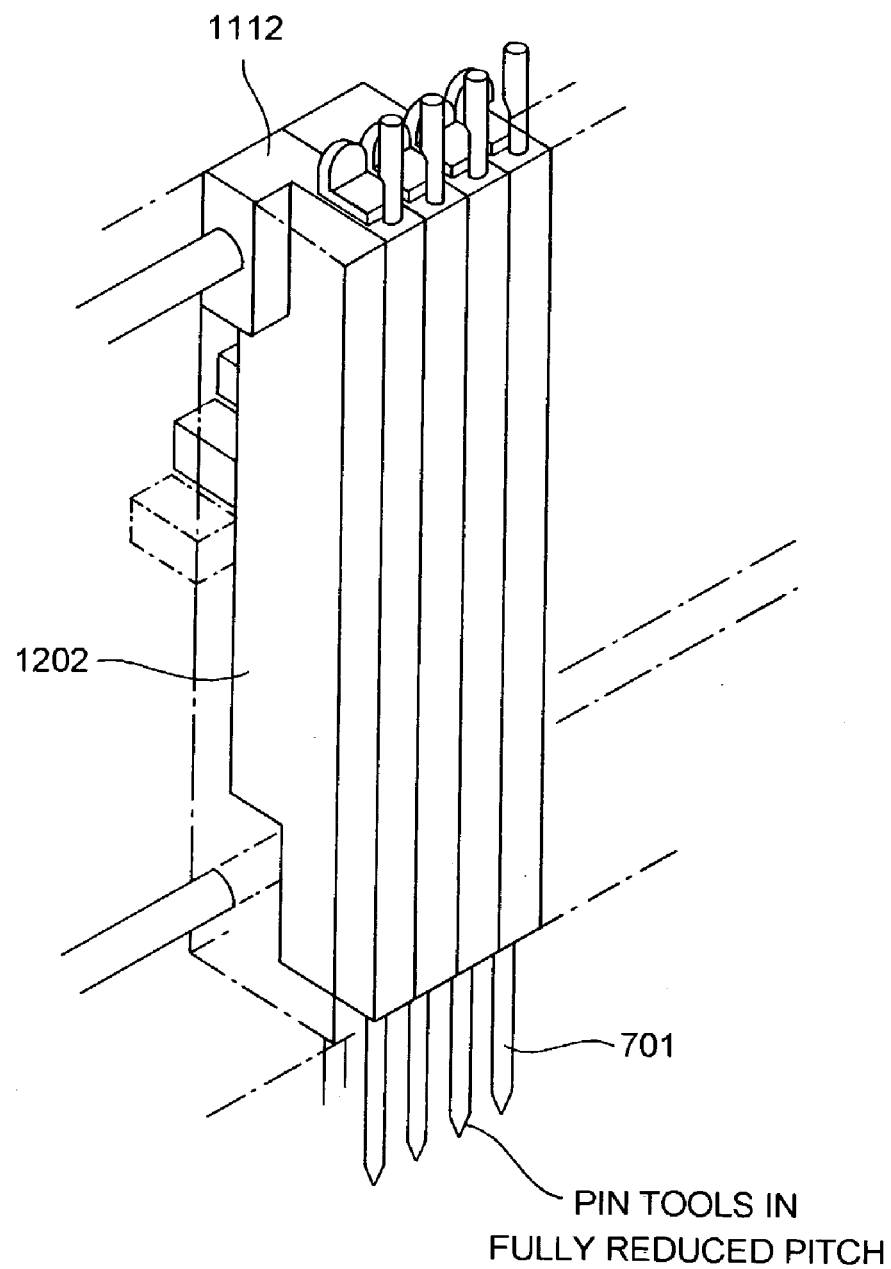
FIG. 15 is a perspective view of a portion of the pins illustrated in FIG. 12.

As mentioned, each of the vertically oriented pins 701 has a protrusion 1202 that engages a pitch changing comb 1112 that is moved laterally when the reformatting is desired. FIG. 15 shows a group of four pins 701, with the protrusion 1202 of the end pin visible, as is a portion of the pitch changing comb 1112. Each row of pins whose pitch is to be changed has a corresponding pitch changing comb 1112. Thus, in FIG. 11, the side view shows a comb 1112 for the first row, and that comb is 1112 also visible in the top view of FIG. 12. The second comb, referred to as pitch changing comb 1112*a*, for the second row is also visible in FIG. 12. These same combs are visible in the corresponding reduced pitch drawings of FIGS. 13 and 14.

FIG. 16 shows the sequence of reformatting as the pitch changing comb 1112 is moved from the fully extended pitch to the fully reduced pitch. As the comb 1112 moves laterally, it engages each additional pin 701 in the row, engaging a new pin as the comb moves along from right to left in the drawing. In FIG. 16, each instance of engaging a new pin 701 is indicated as a step of the reformatting operation, which emphasizes the stepped appearance of the engaging surface of the comb 1112. In the first step, Step 1, the comb 1112 is shaded to highlight its position for easier understanding of the operation. At each illustrated step of FIG. 16, a pin protrusion is indicated as a solid black square, again to highlight its position for easier understanding.

Thus, at Step 1, the top most pin protrusion is already engaged with the highest step of the comb 1112. At Step 2, the comb 1112 has moved toward the left and the next highest step of the comb 1112 has engaged the next highest protrusion, which is located on the next pin. The first pin remains engaged with the comb 1112, and is moved along by the comb 1112 so that its spacing from the second pin is now reduced. Both the first pin and the second pin are moved together toward the third pin and the spacing from the third pin to the second pin and first pin is reduced. In the third step, the comb 1112 has engaged the third pin. Now these three pins are moved along, and the process continues until all twelve pins in the pin block are moved. At the last step (step 12), all twelve pins have been moved and have a new uniform pitch that is one-quarter of its prior pitch, being more nearly the same pitch as the target locations on the chip.

It should be appreciated that the pitch of the pins in each pin block 606 can be reformatted independently of every other pin block on the dispensing head. For example, the pins of pin block 606a can be set to a first pitch and the pins of pin block 606b can be set to a different pitch than the pins of block 606a. Thus, the pitch of each pin block 606 can be formatted independently of the other pin blocks, or all of the pin blocks 606 can be formatted as a common group. The pin block 606a can be set to a first pitch suitable for aspirating from an MTP, and then set to a second pitch suitable for dispensing to the target locations on a chip, while the pin block 606b (or any other pin block) can be set to a different pitch during this process. This enables a higher throughput of MTP processing than if the pin blocks all had to be set to a common pitch.

It should be appreciated that the pitch of the pin array may be reduced to be more nearly equal to the pitch of the target locations on the chip, the limitation being the diameter of the pins themselves. That is, the pins of the preferred embodiment have a diameter (including any spring actuation or support structures) that precludes a spacing that is identical to that of the target locations. Those skilled in the art, however, will understand that the technique described herein may be used to reformat the pins to a pitch that is the same as the target locations.

Resin Particle Dispensing

Figure 17A:
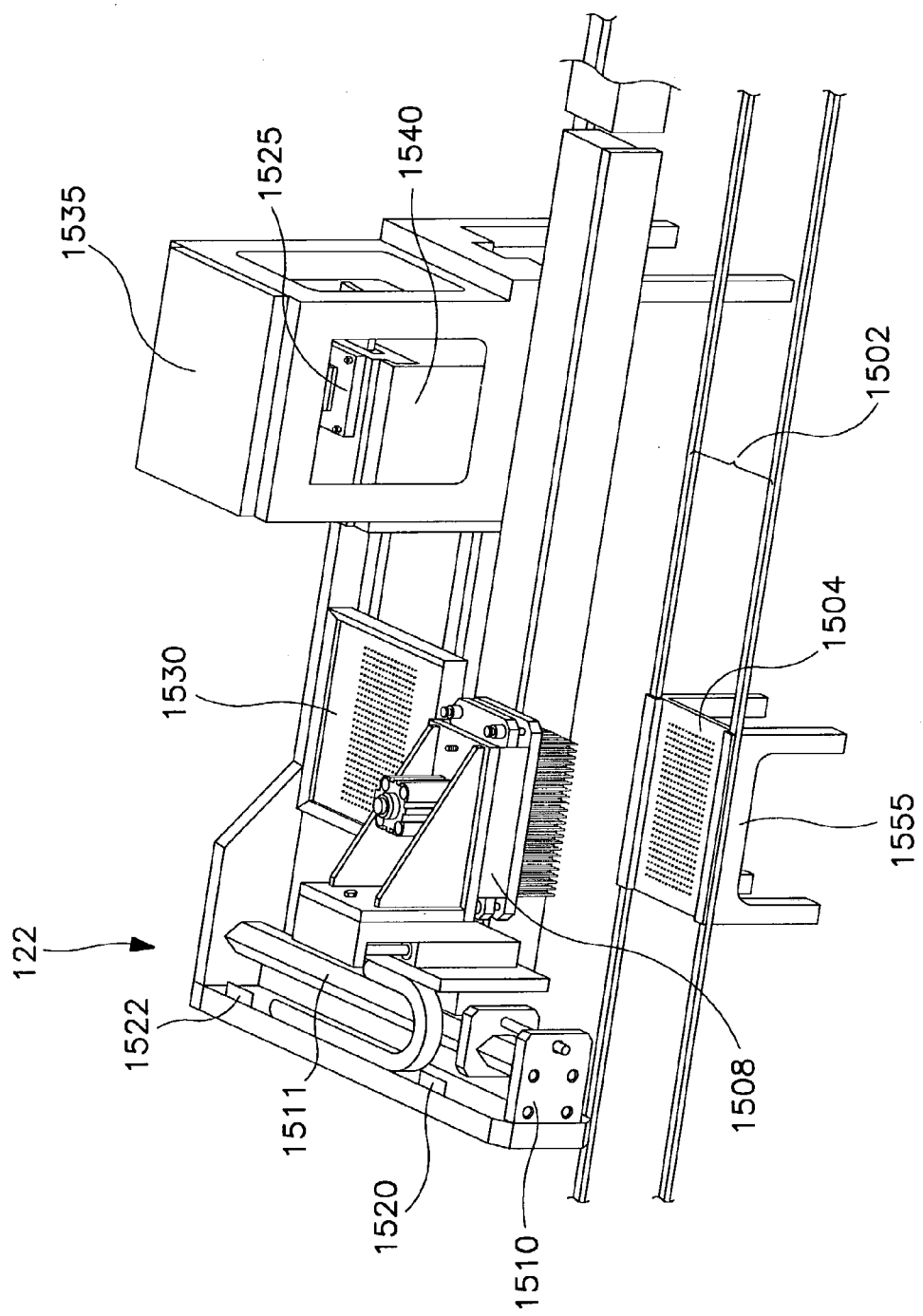
FIG. 17A is a perspective view of a resin dispensing module of the FIG. 1 processing line showing the dispensing operation and the compactor.

FIG. 17A is a perspective view of the resin dispensing module 122 (FIG. 1) of the processing line. Microtiter plates proceed along the main conveyor line 110 and, when appropriate, are directed onto the conveyor 1502 of the resin dispensing module 122 by the computing system 101. It should be understood that only one resin dispensing station is illustrated in FIG. 17A for simplicity of presentation, and that the resin dispensing module 122 illustrated in FIG. 1 includes multiple stations, each of which performs the resin dispensing task.

The resin dispensing module 122 includes a conveyor 1502, which directs the MTPs 1504 to the module 122. It also includes a resin dispensing assembly 1508, which is made up of a number of hollow tubes 1802 (shown in more detail in FIGS. 20A–C). The hollow tubes 1802 can be molded, welded, mechanically attached (such as by individually threading them), or otherwise attached to an array plate 1601, as shown in more detail in FIGS. 18A and 18B. The resin dispensing assembly 1508 is mounted on a transport mechanism 1510. The transport mechanism 1510 includes a guide rail 1511 along which the dispensing assembly 1508 slides. The guide rail 1511 includes sensors 1520 and 1522 at its proximal and distal ends respectively, and these sensors are used to detect the position of the dispensing assembly 1508. The dispensing assembly 1508 can be moved, for example, pneumatically or hydraulically along the guide rail 1511. The module 122 also includes a resin reservoir assembly 1535 and a skimming plate 1530, each of which will be discussed in more detail below.

FIG. 17A shows an MTP 1504 that has been directed from the main conveyor line 110 onto the resin dispensing line 1502. In FIG. 17A, the hollow tube array 1506 has been loaded with resin particles and is positioned over the MTP 1504, ready to dispense resin particles from each of the hollow tubes 1802 into the wells of the MTP 1504. The hollow tubes 1802 of the array 1506 are suspended from the dispensing assembly 1508 that is mounted to the transport mechanism 1510 that moves the dispensing assembly in a direction perpendicular to the module line 1502 along a Y axis. Positioned underneath the MTP 1504 is a lifting platform 1555, which aligns the MTP 1504 with the array 1506, and lifts the MTP 1504 slightly toward the array 1506.

The dispensing assembly 1508 starts from a point of origin just above the conveyor 1502 and the lifting platform 1555, at the proximal end of the guide rail 1511. A sensor 1520 (see FIG. 17C) attached to the guide rail 1511 is used to detect the position of the dispensing assembly 1508. From that point of origin, the dispensing assembly 1508 is moved distally along the guide rail 1511 (along the Y axis), until it stops at the distal end of the guide rail 1511, where a sensor 1522 (see FIG. 17C) is stationed to detect the arrival of the dispensing assembly 1508. Looking now at FIG. 17C for a view of the module 122 from the rear, the dispensing assembly 1508 stops above a skimming plate 1530. FIG. 17D is a side section view of the resin dispensing module described above.

The skimming plate 1530 can be made of any durable and stiff material, and in one embodiment is made of machined aluminum with a stainless steel perimeter. The skimming plate 1530 has holes through which the hollow tubes of the array 1506 slide. The skimming plate 1530 can have at least as many holes as there are hollow tubes on the array 1506, but not fewer. In one embodiment, the array 1506 has 384 hollow tubes, and the skimming plate 1530 has 384 holes. In another embodiment, the array 1506 has 96 hollow tubes, and the skimming plate has 96 holes. In yet another embodiment, the array 1506 has 1,536 hollow tubes and the skimming plate has 1,536 holes in it. The holes of the skimming plate 1530 are aligned with the hollow tubes of the array 1506 so that all of the hollow tubes will slide simultaneously through each of their corresponding holes when the dispensing assembly 1508 is positioned over the skimming plate 1530.

Either before, during, or after the dispensing assembly 1508 is positioned over the skimming plate 1530, the resin reservoir 1540 is deployed. The resin reservoir assembly 1535 deploys the resin reservoir 1540, which can be pneumatically or hydraulically guided along the X axis toward the skimming plate 1530. It comes to a stop just under the skimming plate 1530.

Once the resin reservoir 1540 is in position underneath the skimming plate 1530, and the array 1506 is in position over the skimming plate 1530, the array 1506 is pneumatically or hydraulically lowered along the Z axis. Vertical displacement shafts 1630 on the dispensing assembly 1508 slide vertically into vertical displacement bores 1632, thus allowing the array 1506 to drop vertically. This allows the hollow tubes 1802 to slide through the holes of the skimming plate 1530, and into the resin reservoir 1540, filling the distal ends of the tubes 1802 with resin. The force of lowering the array 1506 into the reservoir 1540 pushes resin particles up into each of the hollow tubes 1802. The friction between particles after they have been pushed into the tubes 1802 holds the particles within the tubes as the array 1506 is moved out of the resin reservoir 1540. The resin particles also become frictionally engaged with the inner surfaces of the hollow tubes 1802 (as shown in more detail in FIG. 20C).

The array 1506 is then pneumatically or hydraulically raised along the Z axis, and the hollow tubes 1802 are withdrawn from the resin reservoir 1540 and are raised through the holes of the skimming plate 1530. The diameter of each of the holes in the skimming plate 1530 is just slightly larger than the diameter of each of the hollow tubes 1802, such that when the hollow tubes 1802 are withdrawn through the holes of the skimming plate 1530, the outside surfaces of the hollow tubes 1802 are skimmed clean by the skimming plate 1530. This ensures that unwanted amounts of resin do not cling to the outside surface of the hollow tubes and become inadvertently dispensed into an MTP 1504.

In an alternative embodiment, the array 1506 can remain static while the resin reservoir 1540 is raised to meet the array 1506. The reservoir can engage the skimming plate 1530 and raise it toward the array 1506, resulting in the hollow tubes 1802 being threaded through the holes in the skimming plate 1530. Once the hollow tubes are filled with resin, the reservoir 1540 can be lowered along with the skimming plate.

Once the array 1506 is completely withdrawn vertically, the dispensing assembly 1508 is pneumatically or hydraulically guided along the Y axis back to its point of origin. Either before, during, or after the dispensing assembly 1508 arrives at its point of origin, an MTP 1504 will be guided along the conveyor 1502 and will come to a rest above the lifting platform 1555 and just underneath the array 1506.

The lifting platform 1555 is stationed at a predetermined position beneath the point of origin of the dispensing assembly 1508. When the MTP 1504 slides over the lifting platform 1555, the lifting platform is raised upward and catches the MTP 1504. The lifting platform can have raised edges that fit snugly around the MTP 1504, thus aligning the MTP 1504 with the array 1506, which is above it. Alternatively, the lifting platform 1555 can have other means of aligning the MTP 1504 with the array 1506. For example, the lifting platform 1555 can have magnets on its upper surface with corresponding metal points on the bottom surface of the MTP 1504, or the metal points and magnets can be reversed so that the magnets are on the MTP 1504, while the metal points are on the lifting platform 1555. In another embodiment, the upper surface of the lifting platform 1555 can have one or more holes, bores, cavities, grooves, or slots into which corresponding protuberances on the bottom surface of the MTP 1504 fit, or vice versa.

The MTP 1504 can have a number of wells equal to the number of hollow tubes 1802. The wells of the MTP 1504 and the hollow tubes 1802 in the array 1506 will be aligned, and the array will be pneumatically or hydraulically lowered along the Z axis toward the MTP 1504. The array 1506 will then come to a rest and plungers 1804 within each of the hollow tubes 1802 will be lowered, causing the resin to be pushed out of the hollow tubes and into the wells of the MTP 1504.

Figure 19A:
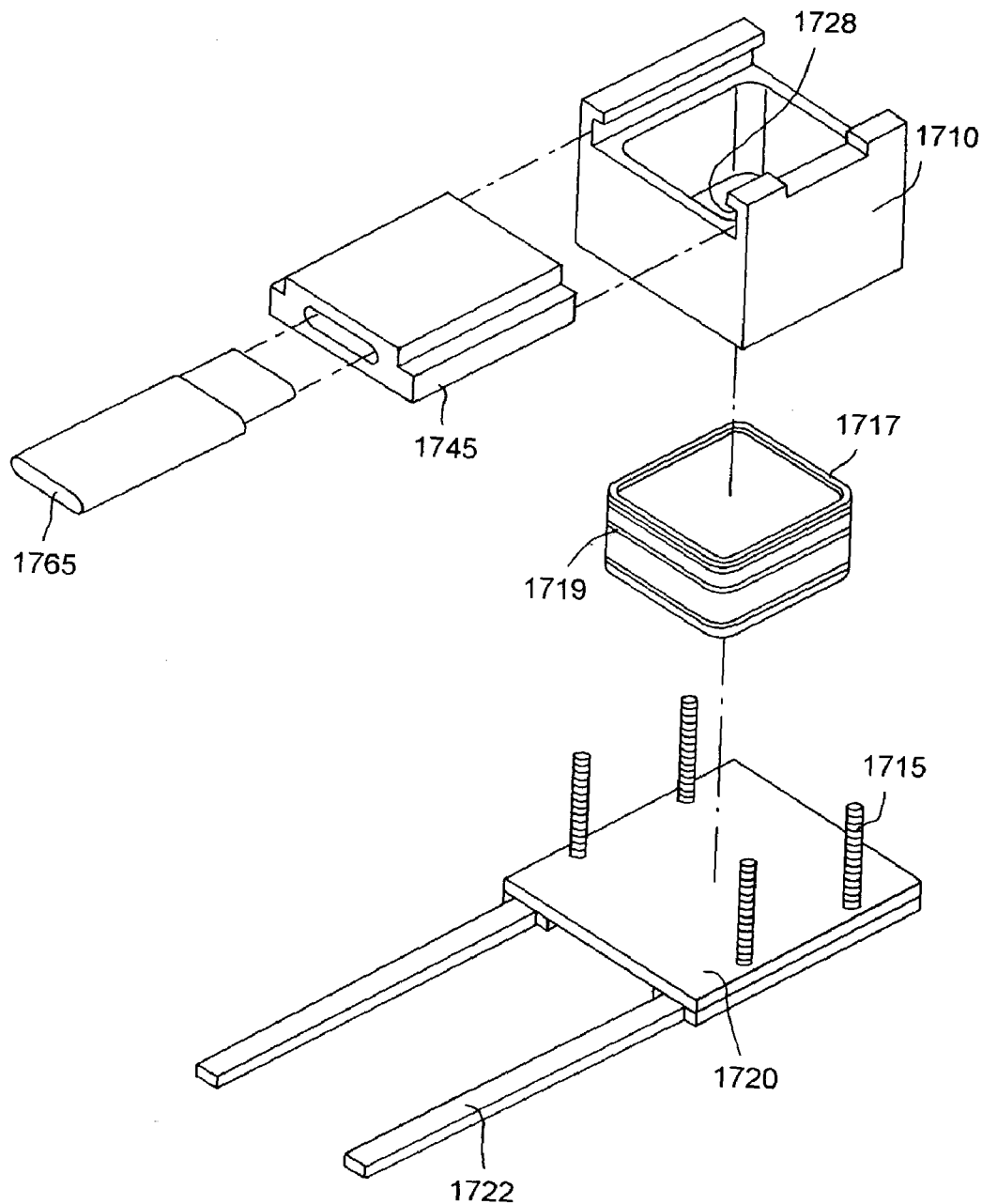
FIG. 19A is an exploded three-dimensional view of the resin reservoir of the resin dispensing module of FIG. 17A.
Figure 19B:
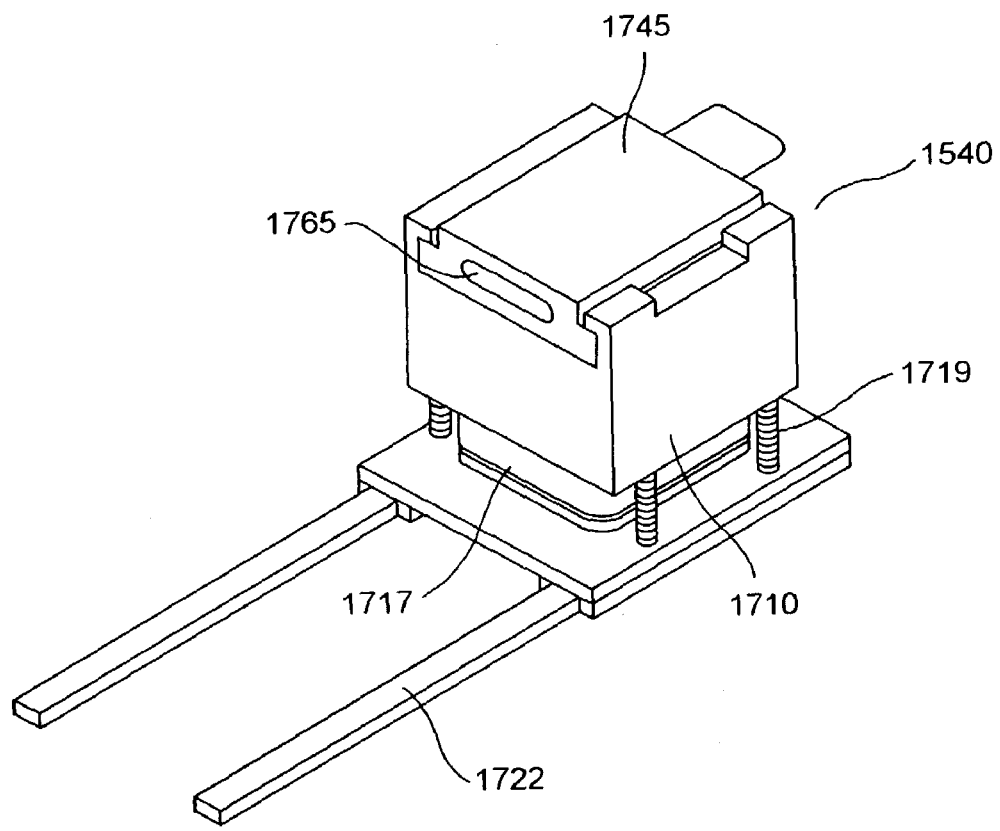
FIG. 19B is a perspective view of the resin reservoir assembly of the resin dispensing module of FIG. 17A.

Meanwhile, the resin reservoir 1540 can be pneumatically or hydraulically guided back to its point of origin, where it can slide underneath a compacting lid 1745, which engages the top of the reservoir 1540. A compactor can pneumatically or hydraulically press down against the lid 1745 to pack the resin so that a flat and uniform resin bed is achieved. In addition, a vibrator 1765 (as shown in FIG. 19B) can be used to vibrate the compacting lid 1745 to further pack the resin particles into a flat and uniform bed.

In the preferred embodiment, the number of hollow tubes in the array 1506 is equal to the number of wells in the MTP 1504. Thus, loading of all hollow tubes takes place simultaneously, and dispensing of all hollow tubes takes place simultaneously, and loading of all microtiter wells occurs simultaneously. The resin dispensing module of the present invention thereby assists in throughput increasing efforts.

The Resin Dispensing Assembly

FIG. 18A is a closer view of the resin dispensing assembly 1508. The resin dispensing assembly includes an array 1506 of hollow tubes 1802. The hollow tubes 1802 can be welded, integrally molded, or mechanically attached (such as by individually threading) to a rectangular array plate 1601, having a length L, a width W, and a depth D.

Figure 20A:
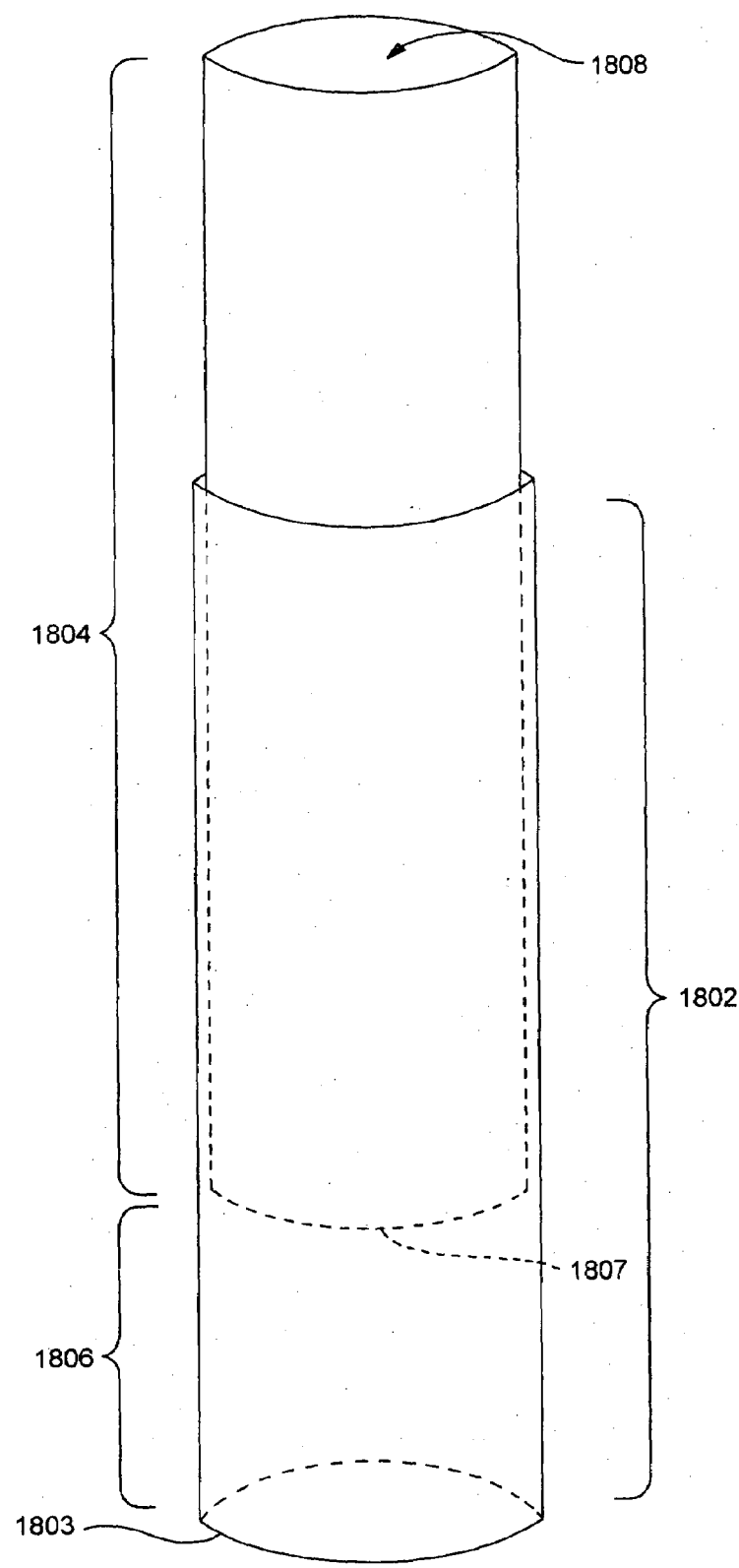
FIG. 20A is a schematic representation of the lower portion of one hollow tube in the 384-tube array illustrated in FIG. 17A, showing the tube plunger in its raised position.

In one embodiment the array plate 1601 is solid, and a number of holes are bored through it from its top surface 1611 to its bottom surface 1612. The number of holes is equal to the number of hollow tubes 1802 in the array 1506. The hollow tubes 1802 can be attached to the bottom surface 1612 of the array plate 1601 in any manner known to those in the art, such as welding or securing with an adhesive. The hollow tubes and the bored holes can all be aligned with one another and can have the same diameters, so that the inner walls of the bored holes line up exactly with the inner walls of the hollow tubes. For example, in an array with 384 hollow tubes 1802, this results in an array plate 1601 with 384 passages leading from 384 holes on its top surface through 384 hollow tubes 1802 and out the distal openings 1803 (as seen in FIG. 20A) of those 384 hollow tubes 1802.

In another embodiment, the array plate 1601 can have a number of bored holes leading from openings in the top surface 1611 of the plate to openings on the bottom surface 1612 of the plate. The number of bored holes can be equal to the number of hollow tubes 1802. The hollow tubes 1802 can be radially sized to fit coaxially within the bored holes, and the proximal ends thereof can be inserted through the openings on the bottom surface 1612 of the plate. The hollow tubes 1802 can then be forced through the bored holes until the proximal ends of the hollow tubes 1802 are flush with the top surface 1611 of the plate. The hollow tubes can be coaxially engaged with the bored holes through frictional engagement, by an adhesive, or by any other means known to those with skill in the art. In any case, the result is an array 1506 of hollow tubes 1802, the hollow tubes protruding form the bottom surface 1612 of an array plate 1601 having a corresponding array of bored holes.

The array plate 1601 is connected to an upper plate 1603 by two vertical support walls 1602. The array plate 1601 can be bolted or welded to the vertical support walls 1602, which can be bolted or welded to the upper plate 1603. Isolated from any vertical force exerted on either the upper 1603 or array plate 1601 and floating in between the two is a plunger plate 1605. The plunger plate 1605 can float on one or more springs placed in between the top surface 1611 of the array plate 1601 and the bottom surface 1614 of the plunger plate 1605. The device also has at least two stop posts 1610. The stop posts 1610 include flanged terminals 1616 that prevent the plunger plate 1605 from floating beyond a predetermined distance above the array plate 1601. The stop posts 1610 also align the plunger plate 1605 and array plate 1601. In addition, the stop posts 1610 can have springs (not shown) fitted coaxially around them in between the array plate 1601 and plunger plate 1605. These stop post springs can be used in lieu of or in addition to the springs discussed above.

Figure 18B:
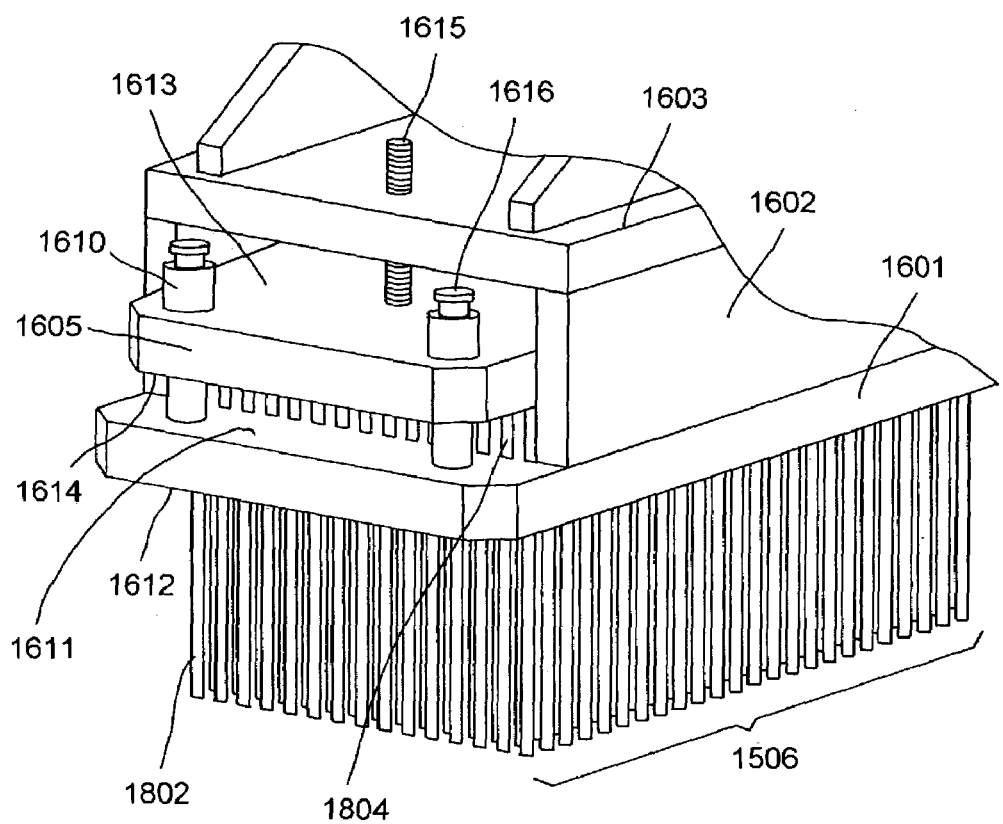
FIG. 18B is a side elevation view of the resin dispensing assembly depicted in FIG. 18A.

Protruding from the bottom surface of the plunger plate 1605 are a number of plungers 1804 (as shown in more detail in FIG. 18B). The number of plungers 1804 can be equal to the number of hollow tubes 1802 in the array 1506. The plungers 1804 are aligned with the holes on the top surface of the array plate 1601, and they are inserted into the hollow tubes 1802 through those holes. The plungers 1804 are at least as long as the hollow tubes 1802. The plungers 1804 are used to simultaneously push the resin out of each of the hollow tubes 1802.

The amount of resin that is collected by the hollow tubes depends on how much space there is between the bottom of the plungers 1807 and the bottom of the hollow tubes 1803

Figure 20B:
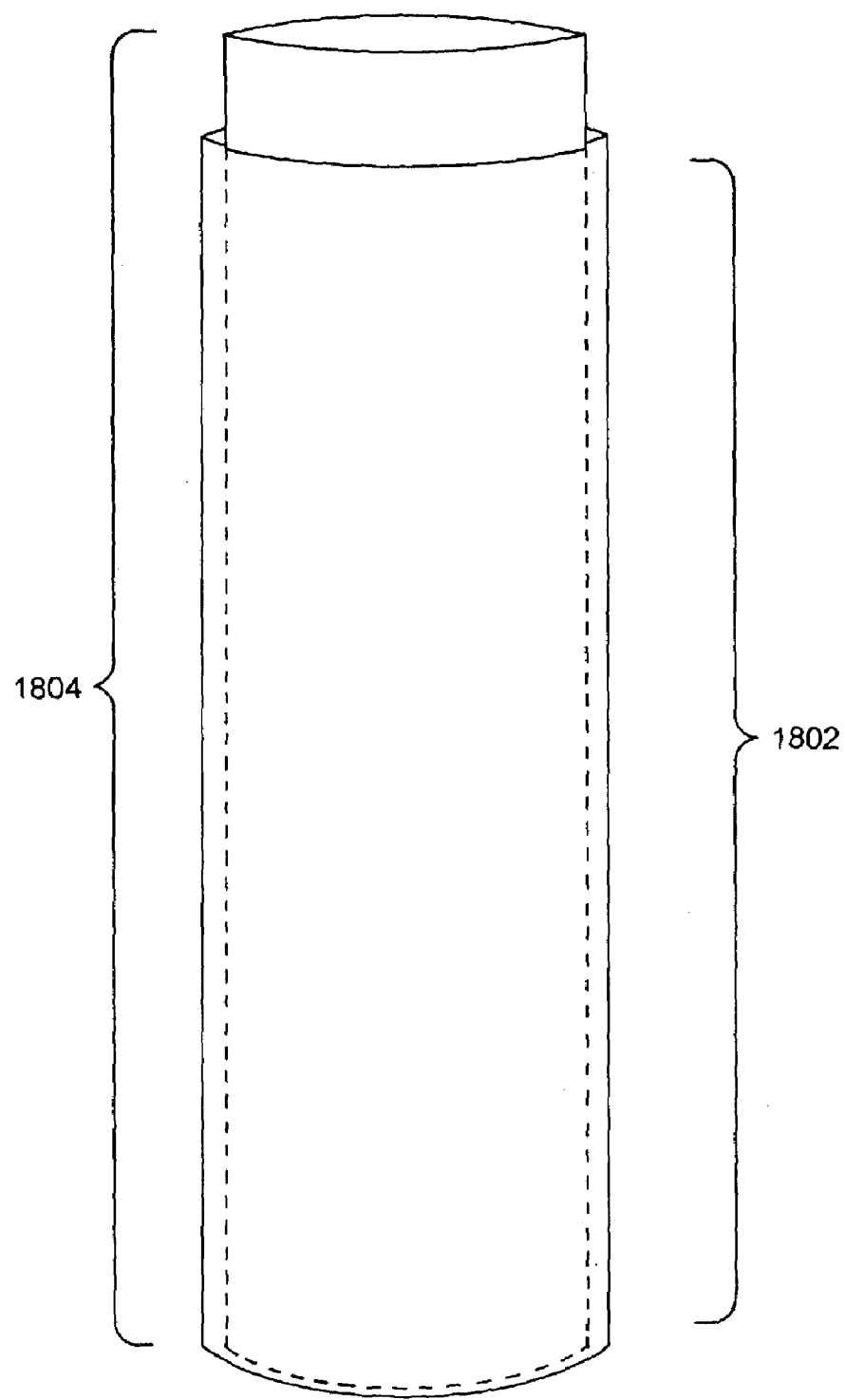
FIG. 20B, is a schematic representation of the FIG. 20A illustration, with the plunger in its lowest position.
Figure 20C:
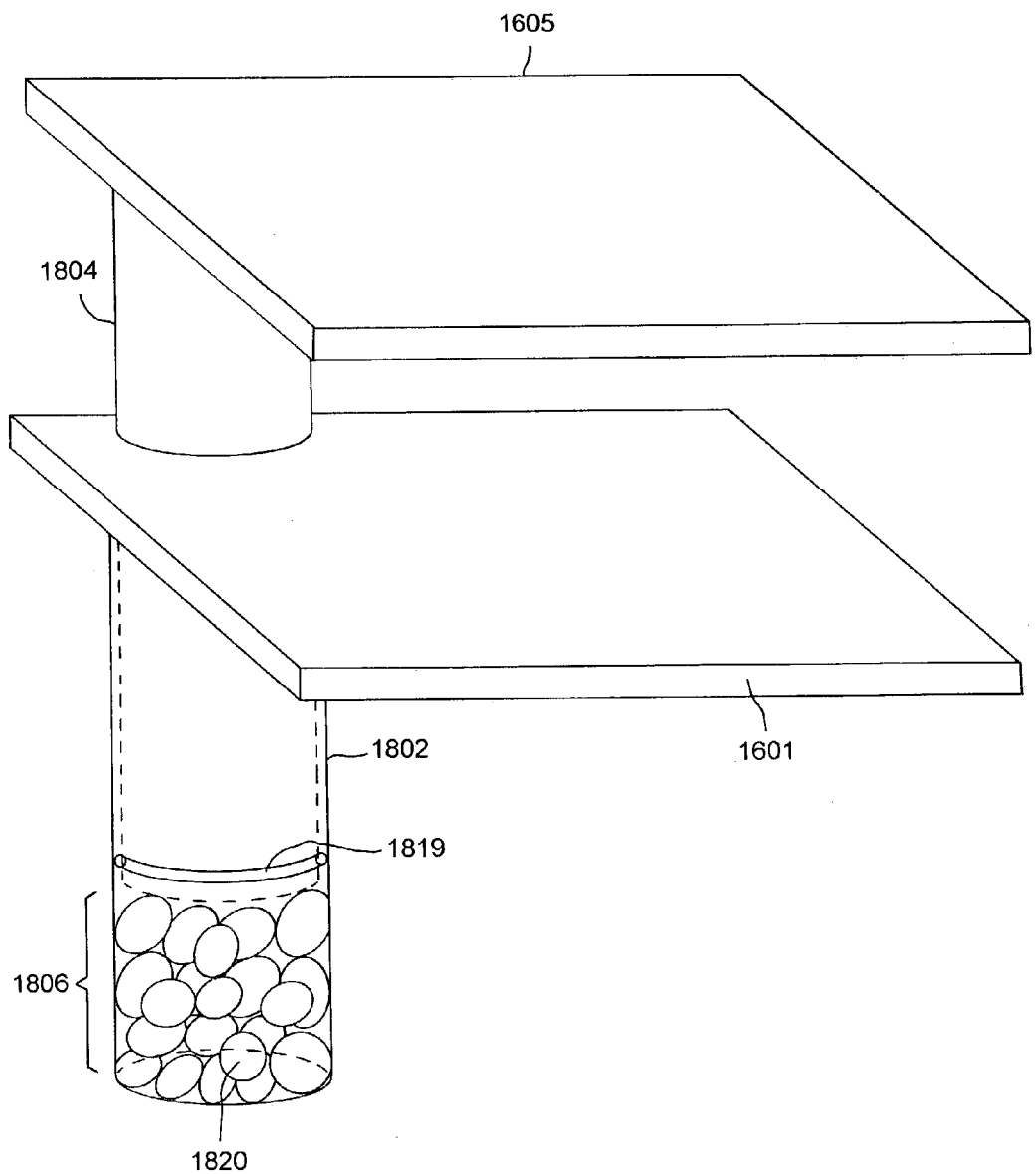
FIG. 20C shows the hollow tube of FIGS. 20A and 20B carrying particles of resin, and coupled to a flat ejection plate.

(as shown in more detail in FIGS. 20A and 20C). This space can be controlled by adjusting the vertical position of the plungers 1804 within the hollow tubes 1802. This adjustment is made using an adjustment screw 1615. The adjustment screw 1615 can be threaded through a threaded hole in the upper plate 1603 and extend out through a corresponding bottom hole. The end of the screw 1615 can be used as a stopper against the upward force of the plunger plate 1605 caused by the springs. The screw 1615 can be calibrated and demarcated so that the amount of resin desired for a particular assay can be adjusted quickly and easily using the screw.

The plungers 1804 can be forced down using a compressing assembly 1625, which can be placed on top of the upper plate 1603, and joined to the top of the plunger plate 1605 through the upper plate 1603. The compressing assembly 1625 can be pneumatic or hydraulic, and like all of the other pneumatic or hydraulic components of the system, can be computer controlled. The dispenser assembly 1508 thus allows for controlled delivery of resin or other chemical or biological reagents.

The Hollow Tubes

FIG. 20A is a schematic representation of the lower portion of one hollow tube 1802. A solid plunger 1804 moves up and down within the hollow tube 1802, and is shown in FIG. 20A in its most upward position. At this raised position, it should be apparent that the volume of resin particles that will be picked up in the tube is defined by the internal tube volume from the bottom 1807 of the plunger 1804 to the open end 1803 of the hollow tube 1802, represented by the portion designated by the brackets 1806. After the hollow tube array is lowered toward the MTP 1504 and is in position over the MTP wells, the plungers 1804 will be lowered, so they push out all the contents (resin particles) contained in the tube 1802, out and into a corresponding well of the MTP 1504. This is illustrated in FIG. 20B, which depicts the plunger 1804 pushed down to its farthest downward location. Alternatively, the hollow tube 1802 can be raised and moved upward in relation to the plunger 1804 rather than the plunger 1804 being lowered. In any case, the plunger 1804 pushes the resin particles 1820 out of the space 1806.

As noted above, the system 100 moves the plungers 1804 down all of the hollow tubes simultaneously. As explained, this may be implemented with a flat plunger plate 1605 connected to all of the plungers 1804, thereby exerting a force simultaneously on all the plungers 1804 and moving them in unison. Thus, as shown in FIGS. 18A, 18B, and 20C, the top surface 1808 of the plungers will preferably be connected to a solid plunger plate 1605.

The plungers 1804 can include one or more channels formed coaxially around the outer surface of their distal ends. For example, FIG. 20C shows a plunger 1804 with a channel formed coaxially on the outside surface at its distal end. An O-ring 1819 can be coaxially mounted into the channel. The O-ring 1819 seals the outer surface of the plunger 1804 against the inside surface of the hollow 1802. Alternatively, a bushing can be coaxially mounted over the plungers 1804, to seal the plungers 1804 against the inside surface of the hollow tubes 1802.

Although the hollow tube is discussed herein with respect to the objective of collecting, transporting, and dispensing resin particles, it should be understood that the device can be used to collect, transport, and dispense any solid material, such as any type of biological or chemical reagent.

The Particle Reservoir Assembly

Figure 17B:
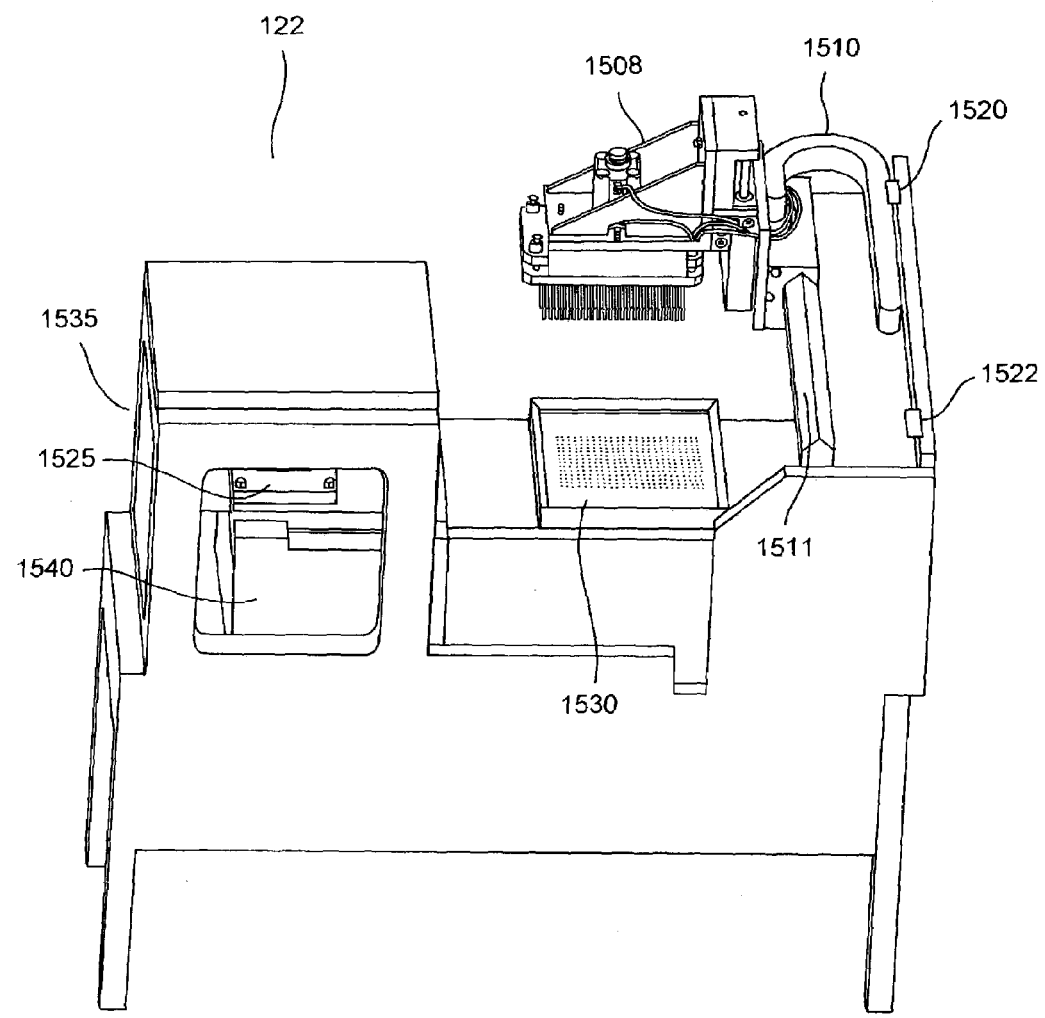
FIG. 17B is a perspective view of the resin dispensing module of FIG. 17A from a different angle.
Figure 17C:
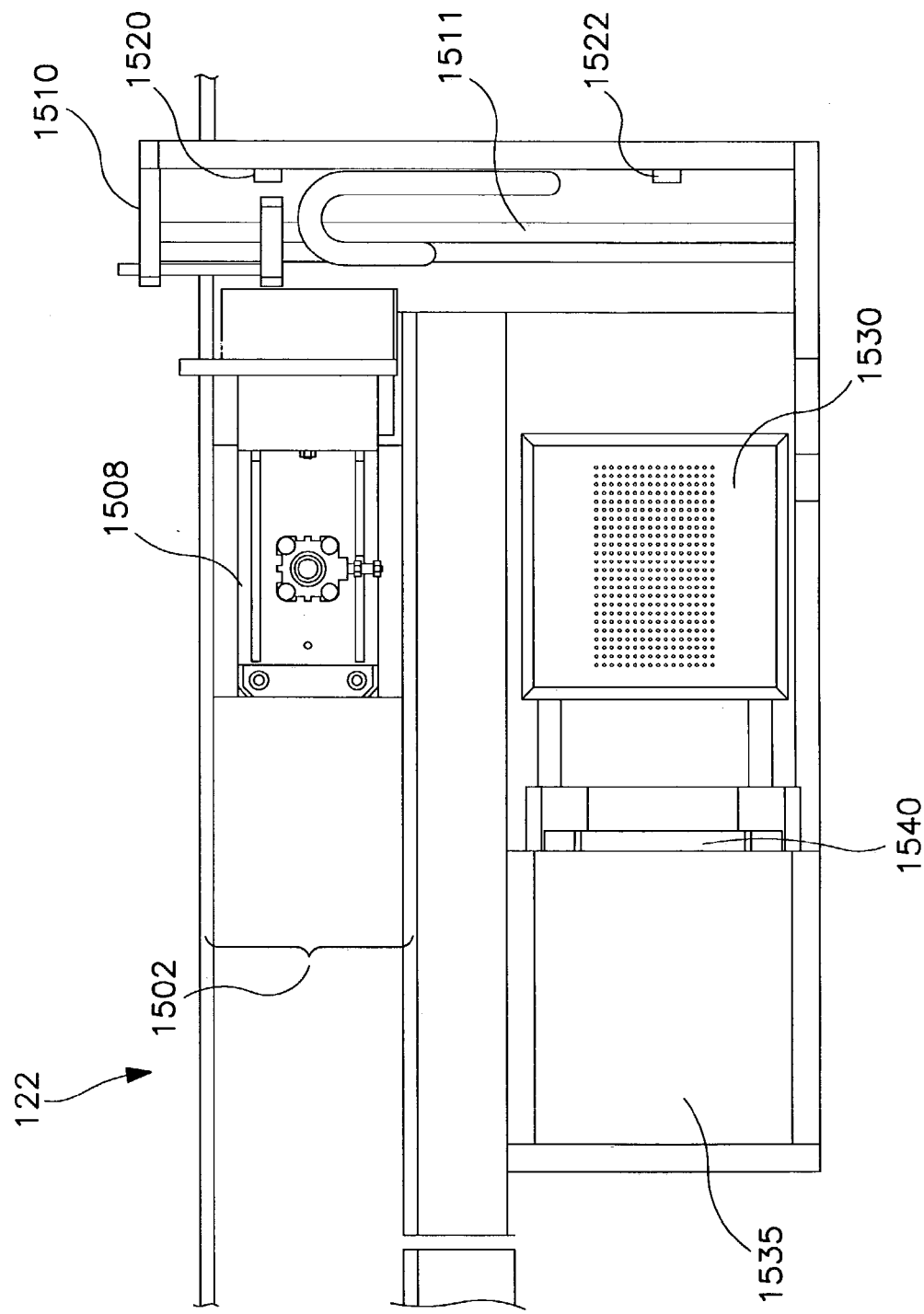
FIG. 17C is a top view of the resin dispensing module of FIG. 17A.
Figure 17D:
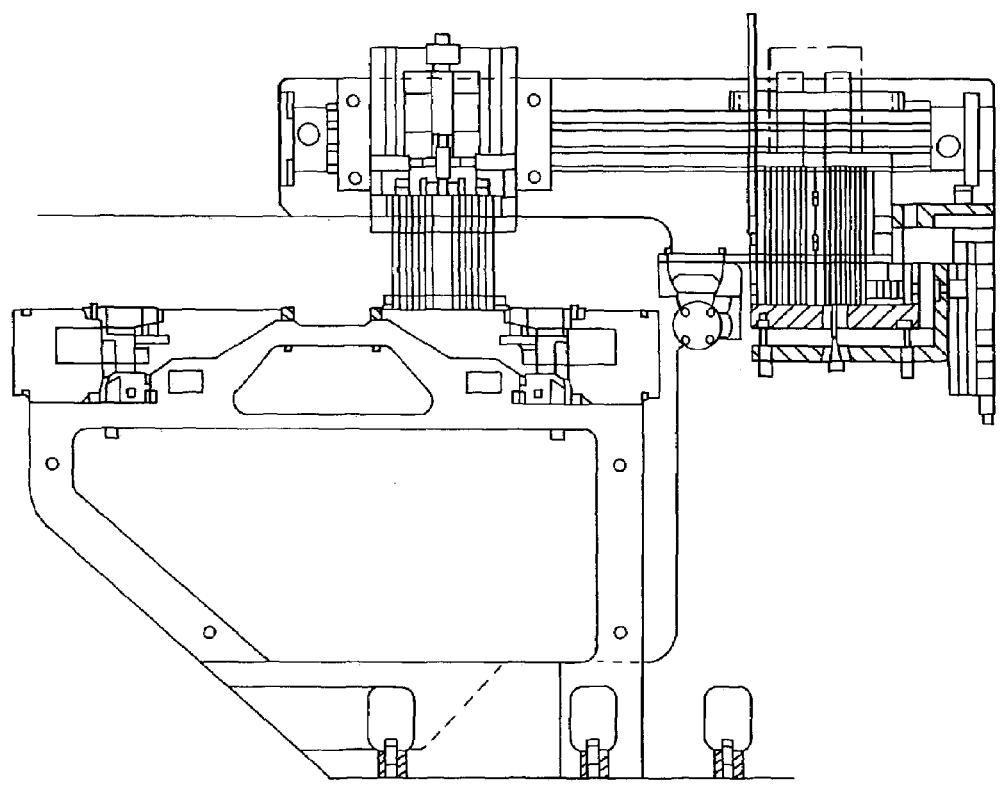
FIG. 17D is a view of the resin dispensing module from a different perspective from that of FIG. 17A.

FIGS. 17A, 17B, and 17C show that the resin dispensing module 122 also includes a resin reservoir assembly 1535, which includes a resin reservoir 1540 where resin, or some other biological or chemical reagent, can be stored for acquisition by the array 1506. FIGS. 17B and 19B show the resin reservoir 1540 in its resting state. As shown in more detail in FIG. 19A, the resin reservoir 1540 can include a foundation 1720 with a number of springs 1715 attached to it. The springs can surround a reservoir base 1717, which rests on top of the foundation 1720. The reservoir base 1717 can include one, two, three, or more O-rings 1719 placed in horizontal channels encircling the base. A reservoir collar 1710 is placed on top of the springs. The reservoir collar 1710 can be any shape, but it must coincide with the shape of the base 1717. If the base 1717 is cylindrical, then the collar 1710 must be shaped in the form of a hollow cylinder. If the base 1717 is rectangular (as shown), then the collar 1710 must have a rectangular opening sized to receive the base 1717. Lengthwise, the top of the collar includes grooves 1728 that are used to secure the compacting lid 1745 against the collar 1710.

The top of the compacting lid 1745 is flat and is connected to a compressor 1525, which can be pneumatically or hydraulically operated. The lid 1745 includes a hollowed out portion, and a vibrator plate 1765 is inserted into it. The rear end of the vibrator plate 1765 includes a stem that is connected to a pneumatic or hydraulic vibrator (not shown) for vibrating the plate. Alternatively, the vibrator plate 1765 can include internal vibrating components and an internal power source. Thus, when the vibrator plate 1765 vibrates, it causes the entire lid 1745 to vibrate. The underside of the compacting lid 1745 is concave and has a channel with an O-ring to seal the lid 1745 against the collar 1710. The underside surface may be coated with a stick-resistant material, such as "Teflon" or the like. Depending on the particle material, other treatments might be desirable for ensuring proper compacting and presenting a uniform surface to the tube array, including electrical charge or airflow.

The reservoir 1540 is formed when the base 1717 is inserted through the collar 1710, the base 1717 forming the bottom of the reservoir, while the collar 1710 forms the walls.

In operation, the foundation 1720, which can be mounted on tracks 1722, can slide underneath the skimming plate 1530. The skimming plate 1530 can be detached and moved out of the way so that the operator can load the reservoir 1540 with resin or some other biological or chemical reagent. Once the reservoir 1540 is loaded, the foundation 1720 can slide pneumatically or hydraulically back to its point of origin underneath the compacting lid 1745. It may be advantageous to compact the particles that are in the reservoir 1540. To accomplish that, the compressor 1525 pushes down on the lid 1745, which is forced onto the collar 1710 and pushes down on it. The collar 1710, which rests on springs 1715, is consequently forced downward over the base 1717 and toward the foundation 1720 until the underside of the lid 1745 comes into contact with the resin in the reservoir 1540. The amount of pressure required will depend on the composition of the resin particles, as will be known to those skilled in the art. Meanwhile, the vibrator plate 1765 causes the lid 1745 to vibrate. The vibration causes the compacting lid 1745 to further pack the resin particles into a flat and uniform bed. Alternatively, a pneumatic or hydraulic vibrator can be connected to the collar 1710, base 1717, or foundation 1720, and can shake or vibrate any of those structures.

Once compaction is complete, the compressor 1525 decompresses, causing a pause in the downward force. Without the extra downward force, the springs 1715 push the collar 1710 and lid 1745 back upward, and the resin in the reservoir 1540 is ready for a new cycle of resin dispensing.

In an alternative embodiment, the foundation 1720 may be pneumatically or hydraulically raised to force the resin against the lid 1745, rather than forcing the lid downward. In either case, the effect is to force the underside of the lid against the resin, thus compacting the resin.

The resin compacting protocol can be repeated several times until the resin is sufficiently compacted and ready for a cycle of dispensing. The compacting lid 1745 is useful because, as the hollow tubes 1802 are withdrawn from the reservoir 1540 in their loaded state, they may likely leave a corresponding array of voids in the particle bed of the reservoir 1540, corresponding to the volumes that were drawn out of the reservoir 1540 and pushed into the hollow tubes 1802. Therefore, the lid 1745 is used to rearrange the particles and provide a substantially uniform bed of resin particles. This ensures that a level surface will be presented to the tube array at the next loading cycle of the dispensing module.

Computer Control

The process line 100 illustrated in FIG. 1, whose operation has been described above in conjunction with the flow control, reconfiguration, alignment, and reformatting operations, preferably is controlled by the computer system illustrated in FIG. 1. That computer system includes a conventional programmable computer, and communicates with the devices of the various process line stations over a data network, to thereby control the operations that occur at each module and each station. An exemplary computer embodiment for performing these control functions is illustrated and described below.

Figure 21:
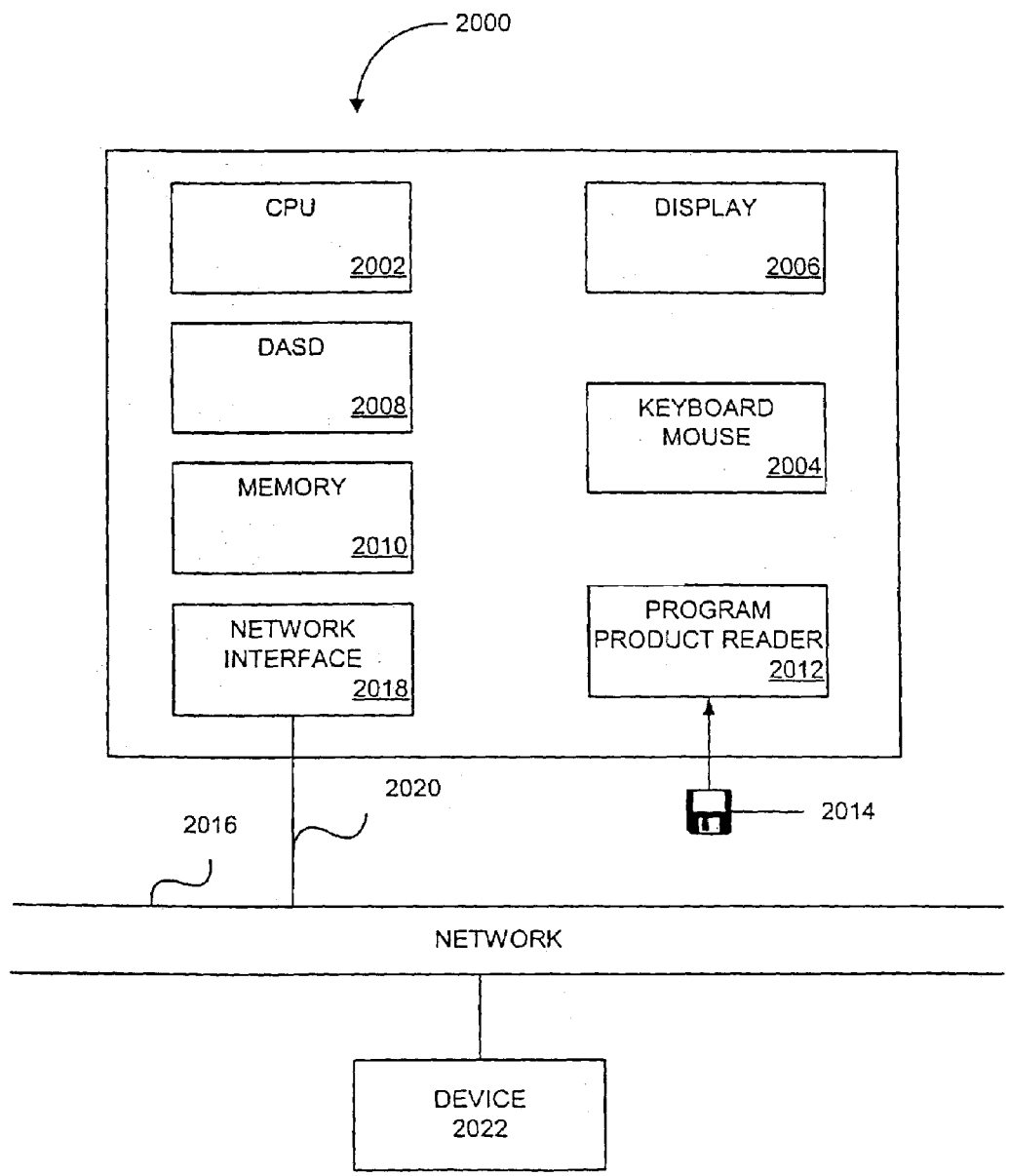
FIG. 21 is a representation of a computer such as can be used to perform the control tasks described herein.

FIG. 21 is a block diagram of a computer that may be used to implement the process line control described herein. It should be understood that the process line control functions described herein may be performed with a single computer, or may be used in conjunction with one or more computers that may communicate with each other over a network to share data. Those skilled in the art will appreciate that the various processes described above may be implemented with one or more computers, all of which may have a similar computer construction to that illustrated in FIG. 21, or may have alternative constructions consistent with the capabilities described herein.

FIG. 21 shows an exemplary computer 2000 such as might comprise one of the computers that implements the functions and actions described above. Each computer 2000 operates under control of a central processor unit (CPU) 2002, such as a "Pentium" class microprocessor and associated integrated circuit chips, available from Intel Corporation of Santa Clara, Calif., USA. A computer user can input commands and data from a keyboard and computer mouse 2004, and can view inputs and computer output at a display 2006. The display is typically a video monitor or flat panel display. The computer 2000 also includes a direct access storage device (DASD) 2008, such as a hard disk drive. The memory 2010 typically comprises volatile semiconductor random access memory (RAM). Each computer preferably includes a program product reader 2012 that accepts a program product storage device 2014, from which the program product reader can read data (and to which it can optionally write data). The program product reader can comprise, for example, a disk drive, and the program product storage device can comprise removable storage media such as a magnetic floppy disk, a CD-R disc, a CD-RW disc, or DVD disc.

The computer 2000 can communicate with other computers and with the devices of the process line over a computer network 2016 (such as a local area network, or the Internet or an intranet) through a network interface 2018 that enables communication over a connection 2020 between the network 2016 and the computer 2000. The network interface 2018 typically comprises, for example, a Network Interface Card (NIC) or a modem that permits communications over a variety of networks.

The CPU 2002 operates under control of programming steps that are temporarily stored in the memory 2010 of the computer 2000. When the programming steps are executed, the computer performs its functions. Thus, the programming steps implement the functionality of the process line control system described above. The programming steps can be received from the DASD 2008, through the program product storage device 2014, or through the network connection 2020. The program product storage drive 2012 can receive a program product 2014, read programming steps recorded thereon, and transfer the programming steps into the memory 2010 for execution by the CPU 2002. As noted above, the program product storage device can comprise any one of multiple removable media having recorded computer-readable instructions, including magnetic floppy disks and CD-ROM storage discs. Other suitable program product storage devices can include magnetic, tape and semiconductor memory chips. In this way, the processing steps necessary for operation in accordance with the invention can be embodied on a program product.

Alternatively, the program steps can be received into the operating memory 2010 over the network 2016. In the network method, the computer receives data including program steps into the memory 2010 through the network interface 2018 after network communication has been established over the network connection 2020 by well-known methods that will be understood by those skilled in the art without further explanation. The program steps are then executed by the CPU 2002 thereby comprising a computer process. If desired, updates to the computer software may be achieved in this manner. FIG. 21 shows a device 2022 connected to the network 2016 in a similar configuration as the computer 2000. It should be apparent that the device 2022 may comprise another computer and may also include one or more of the devices comprising the process line 100, as described above.

Thermal Cycling

As noted above, some systems make use of thermal cycling operations to subject the materials to temperature regimens. The automated process line illustrated in FIG. 1, constructed in accordance with one embodiment of the present invention, introduces fluids of different temperatures to a configuration of multiple flow pathways formed by flow cell assemblies on which microtiter plates (MTPs) are mounted and fixed by upper heated lids. Fluids of different temperatures are supplied from fluid reservoirs to the underside of the microtiter plate. Valves switch fluid from a selected reservoir to a manifold that distributes the fluid stream to the individual flow cells. The unselected reservoirs remain in continuous circulation by bypassing the manifold to maintain the system at a fixed bath temperature.

In accordance with the invention, an insert is integrated into each flow cell assembly, such that the insert supports the wells of the MTP from beneath and contains flow directing guide elements that promote a uniform fluid pressure over the whole length of the MTP perpendicular to the direction of flow. This ensures a uniform flow over the wells of the MTP. The insert provides faster temperature change of the well contents and provides a more uniform distribution of temperature through all the wells of the plate and within each of the wells. The flow directing guide elements, and selection of an appropriate flow rate provide a uniform temperature distribution across the active flow cell area. Upon completion of the thermal cycling process, the MTPs are dried and brought to ambient temperature by introducing compressed gas.

Figure 22:
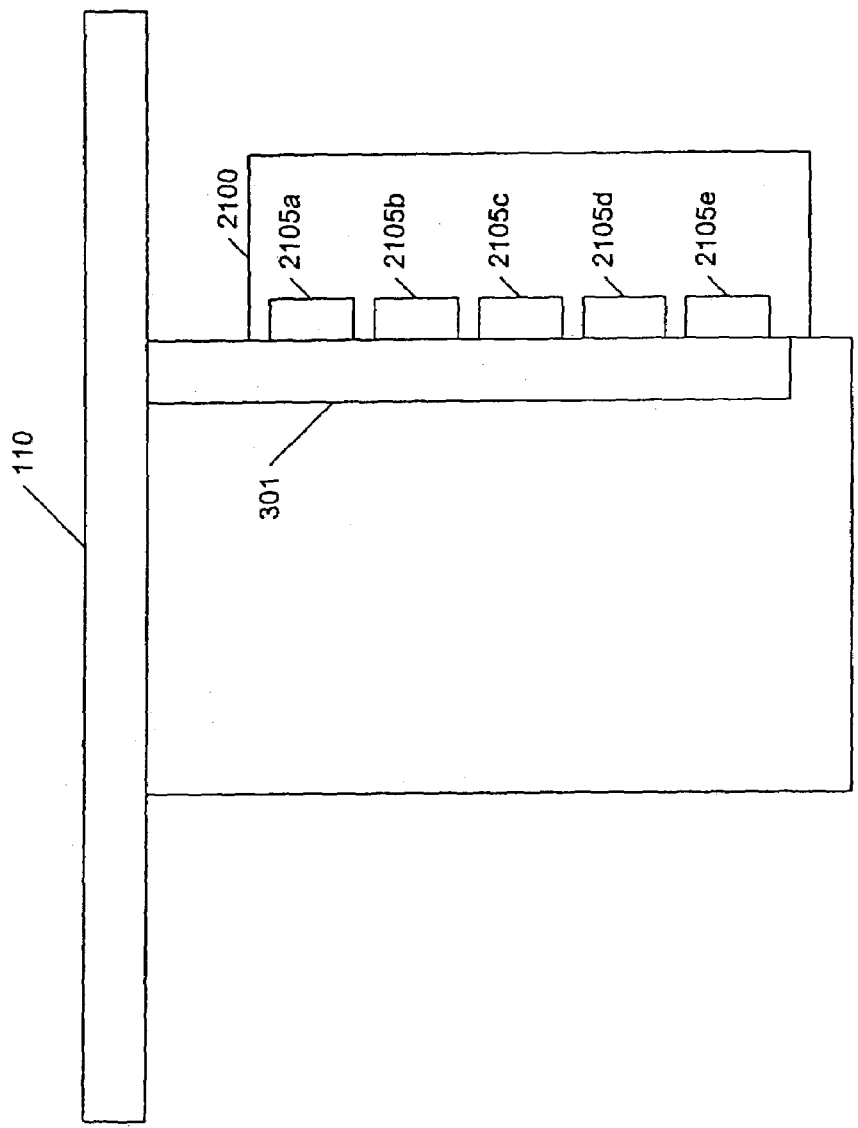
FIG. 22 shows a schematic, top view diagram of a process line thermal cycling module where thermal cycling of one or more microtiter plates can be performed.
Figure 23:
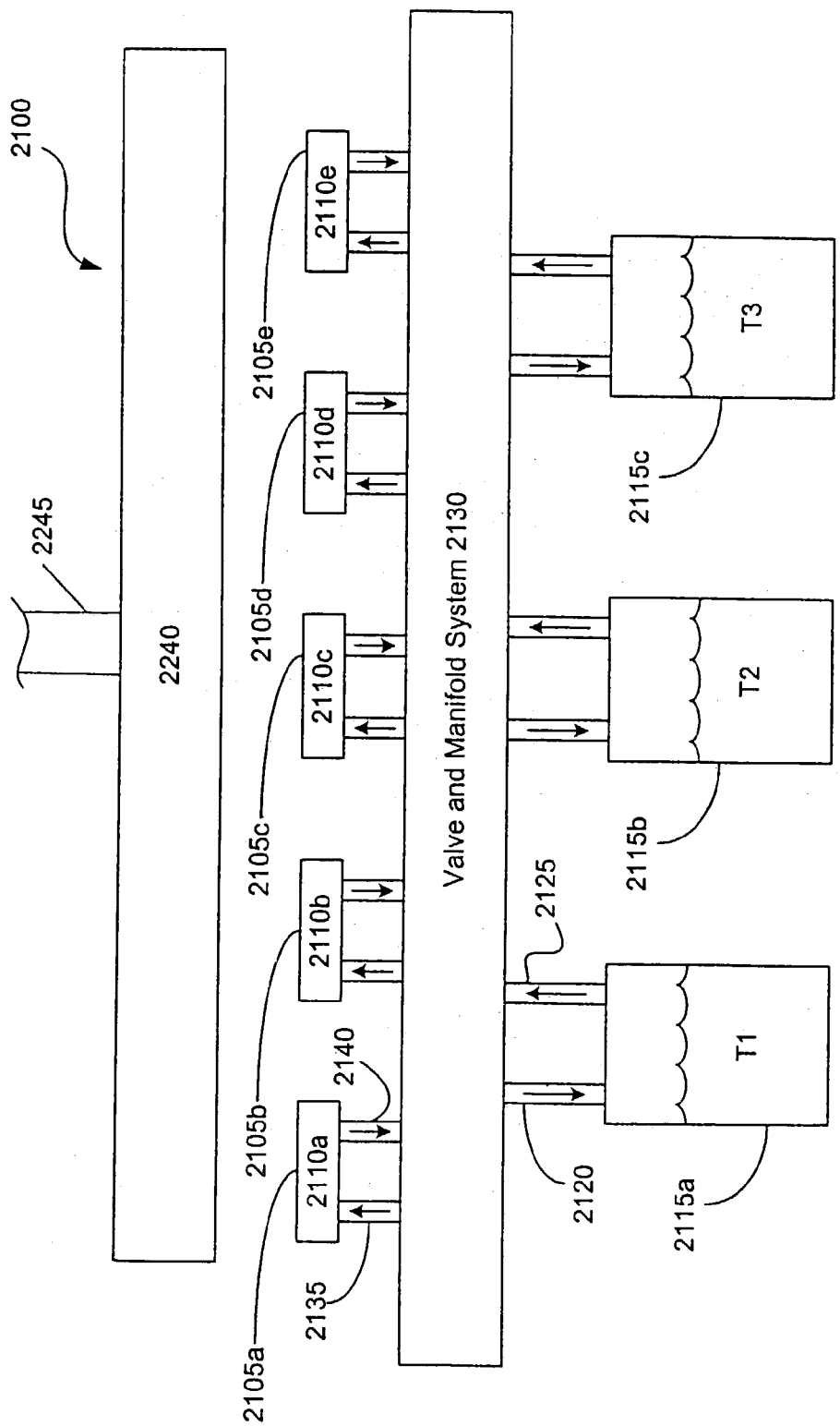
FIG. 23 is a schematic side view of a thermal cycling system of the thermal cycling module, showing various components of the thermal cycling system.

FIG. 22 shows a schematic, top view diagram of the process line module 114, where thermal cycling of one or more MTPs can be performed. The module 114 includes a workstation comprised of a thermal cycling system 2100 that includes one or more thermal cycling stations 2105, including stations 2105a, 2105b, 2105c, 2105d, 2105e. Throughout this description various items are referred to generally and collectively using a reference numeral, and sometimes referred to individually using a reference numeral followed by a letter suffix. It should be appreciated that items that are referred to using a common reference numeral are identical in structure unless otherwise noted. FIG. 23 shows five thermal cycling stations 2105, although it should be appreciated that the thermal cycling system 2100 can include any number of stations.

As shown in FIG. 22, the thermal cycling system 2100 is located adjacent the module conveyor line 301 of the module 114. An MTP can be transported by the module conveyor line 301 to each of the thermal cycling stations 2105 for loading onto the thermal cycling stations. Each thermal cycling station 2105 is configured to receive a single MTP, such as via a conveyor belt that transfers an MTP from the module process line 301 to each station 2105.

FIG. 23 is a schematic side view of the thermal cycling system 2100, showing various components of the thermal cycling system 2100. Each station 2105 is configured to hold a microtiter plate assembly 2110, which includes a microtiter plate that has been loaded onto the station 2105 and various other components that are used to thermally cycle the microtiter plate, as described more fully below. The thermal cycling system 2100 further includes one or more fluid reservoirs 2115 that each contain a fluid that can be distributed to the microtiter plate assemblies 2110. In this regard, each reservoir includes an inlet pipe 2120 through which fluid can flow into the respective reservoir 2115, and an outlet pipe 2125 through which fluid can flow out of the respective reservoir 2115. The inlet pipe 2120 and outlet pipe 2125 of each reservoir 2115 connects to a manifold and valve system 2130 that permits an operator to selectively flow fluids from any of the reservoirs 2115 to any of the microtiter plate assemblies 2110. Each of the stations 2105 includes a corresponding inlet pipe 2135 through which fluid from the manifold and valve system 2130 can be flowed into a microtiter plate assembly 2110, as well as an outlet pipe 2140 through which fluid can be flowed out of a microtiter plate assembly 2110 to the manifold and valve system 2130.

Each of the reservoirs 2115 is temperature controlled in a well-known manner so that the fluid in each reservoir can be maintained at a predetermined temperature. In FIG. 23, the reservoir 2115a is at a temperature T1, the reservoir 2115b is at a temperature T2, and the reservoir 2115c is at a temperature T3. It should be appreciated that the thermal cycler system can include more or less reservoirs than what is shown in FIG. 23.

As shown in FIG. 23, a temperature controlled plate 2240 is located above the microtiter plate assemblies 2110. The plate 2240 can be moved upward and downward relative to the microtiter plate assemblies 2110, such as by a pneumatic lift 2245 that is attached to the plate 2240. The plate 2240 can move downward toward the assemblies 2110 so that the plate contacts the assemblies 2110 and transfers heat to the assemblies 2110. In this manner, the assemblies 2110 can be heated to a desired temperature.

Figure 24:
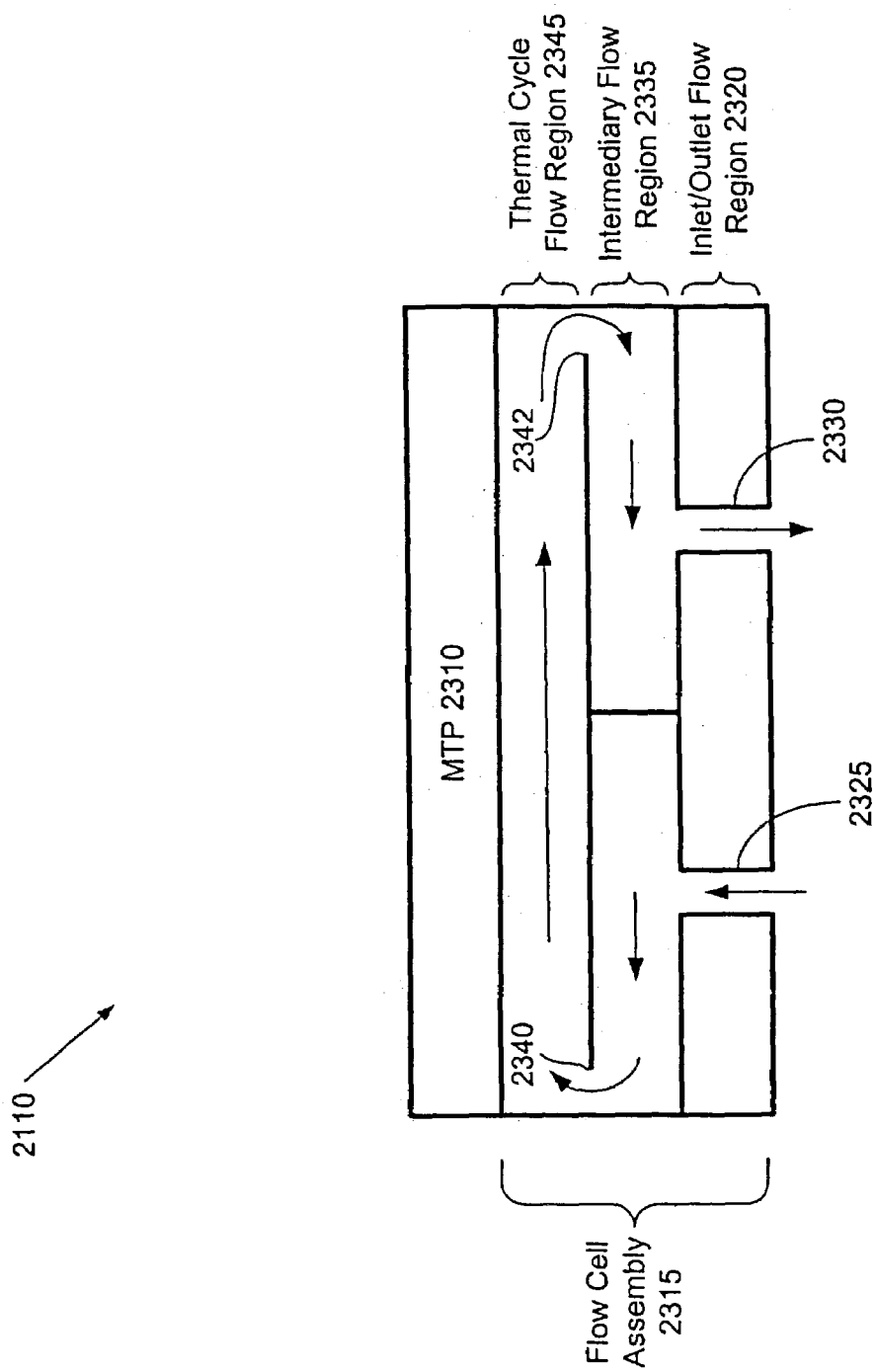
FIG. 24 is a schematic side view of a microtiter plate assembly, showing a fluid flow path through which fluid can flow through the microtiter plate assembly during thermal cycling.

FIG. 24 is a schematic side view of the microtiter plate assembly 2110, which shows the flow path through which fluid can flow through the microtiter plate assembly 2110 during thermal cycling. FIG. 24 omits structural details of the microtiter plate assembly 2110, which structural details are shown and described in other figures below. The microtiter plate assembly 2110 includes a microtiter plate 2310 that is removably positioned atop a flow cell assembly 2315. The flow cell assembly 2315 guides fluid through a flow path so that the fluid contacts at least a portion of the microtiter plate 2310, such as a bottom surface of the microtiter plate 2310. As described in detail below, the fluid is guided in such a manner that it flows evenly across each of the wells of the microtiter plate 2310. FIG. 24 shows the general direction of the flow path using a collection of arrows.

The flow cell assembly 2315 includes three fluid flow regions that collectively guide fluid through the flow path. The fluid flow regions include an inlet/outlet flow region 2320, an intermediary flow region, 2335, and a thermal cycling flow region 2345. The inlet/outlet flow region 2320 is the portion of the flow cell assembly 2315 through which fluid flows into the flow cell assembly 2315 from a respective inlet pipe 2135 (shown in FIG. 23) and through which fluid flows out of the flow cell assembly 2315 through a respective outlet pipe 2140 (shown in FIG. 23). The inlet/outlet flow region 2320 includes an inlet conduit 2325 through which fluid flows into the flow cell assembly 2315, as well as an outlet conduit 2330 through which fluid flows out of the flow cell assembly 2315. In an exemplary configuration, the inlet conduit 2325 guides the fluid so that it flows in a substantially upward direction into the flow cell assembly 2315 from the inlet pipe 2125 (shown in FIG. 23), and the outlet conduit 2330 guides the fluid in a substantially downward direction out of the flow cell assembly 2315 into the outlet pipe 2120 (shown in FIG. 23).

The flow cell assembly 2315 further includes the intermediary flow region 2335 in which (1) fluid is guided from the inlet/outlet flow region 2320 to an inlet opening 2340 that leads to the thermal cycle flow region 2345; and (2) fluid is guided from an outlet opening 2342 (that leads from the thermal cycle flow region 2345) to the inlet conduit 2325 of the inlet/outlet flow region 2320. As described in more detail below, the intermediary flow region 2335 includes one or more flow guide members, such as baffles, that guide fluid through the intermediary flow region 2335 in a predetermined manner toward a desired target location. In one embodiment, the fluid in the intermediary flow region 2335 flows in a sideways, or horizontal, direction as it travels from the inlet conduit 2325 to the inlet opening 2340 and from the outlet opening 2342 to the outlet conduit 2325.

As shown in FIG. 24, the flow cell assembly 2315 further includes the thermal cycling flow region 2345, in which fluid flows in contact with the microtiter plate 2310 to absorb heat from the microtiter plate 2310. The thermal cycling region 2345 includes flow guides that form flow channels through which fluid flows in a predetermined flow pattern underneath rows of wells of the microtiter plate, as described in more detail below. The fluid enters the thermal cycling region 2345 from the intermediary flow region 2335 through the inlet opening 2340 and exits the thermal cycling region 2345 to the intermediary flow region 2335 through the outlet opening 2342.

Figure 25:
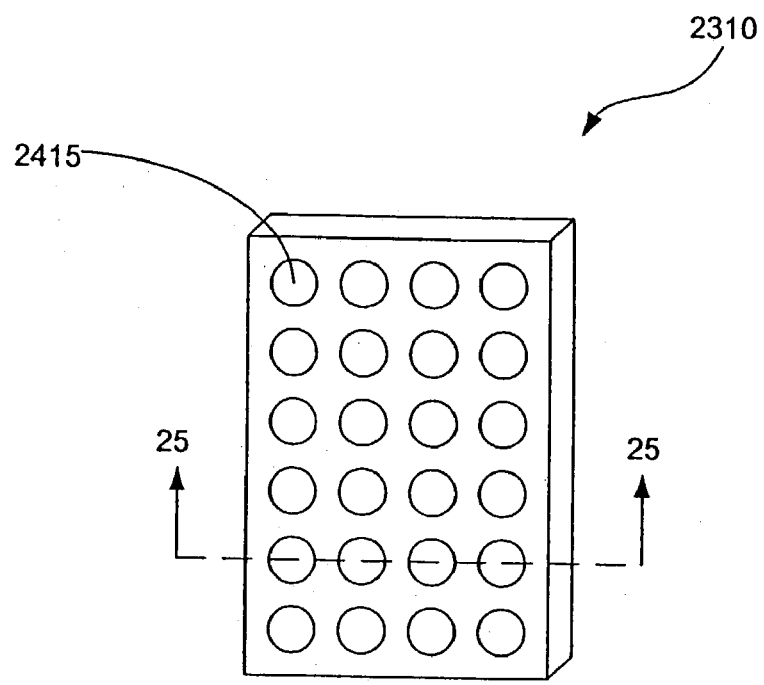
FIG. 25 shows a perspective view of an exemplary microtiter plate.

FIG. 25 shows an exemplary microtiter plate 2310, which includes one or more wells 2415. For clarity of illustration, only one of the wells 2415 is labeled with a reference number. The wells 2415 can be arranged in a series of rows and columns to form an array of wells 2415. Those skilled in the art will appreciate that the microtiter plate 2310 can have any number of wells that are arranged in any number of rows and columns. For example, some microtiter plates, such as the microtiter plate 2310 of FIG. 25, have twenty-four wells arranged in a six row by four column array, and other microtiter plates have ninety-six wells arranged in a twelve row by eight column array. Another conventional type of microtiter plate includes three hundred eighty-four wells arranged in a 16×24 array. The wells can be arranged in any variety of row and column configurations.

Figure 26:
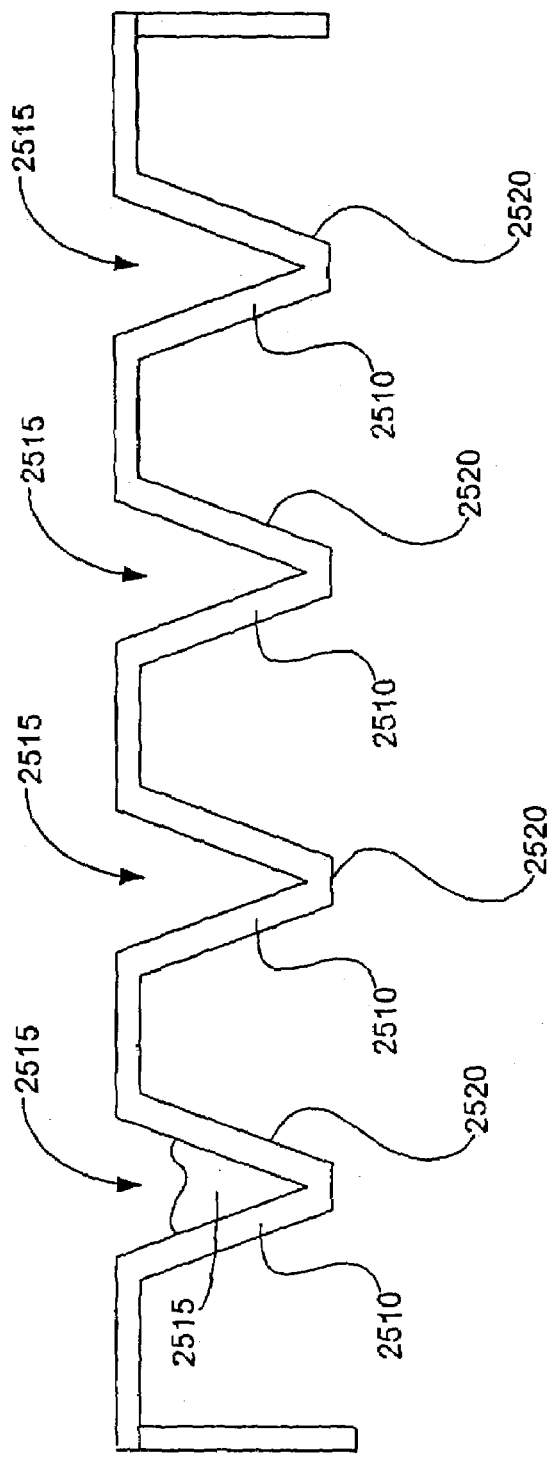
FIG. 26 shows a cross-sectional view of the microtiter plate of FIG. 25 along the line 25—25 of FIG. 25.

FIG. 26 shows a cross-sectional view of the microtiter plate 2310 along the line 25—25 of FIG. 25. The line 25—25 cuts through a row of the wells 2415. The wells 2415 are formed by downwardly-extending thin walls 2510 that define the shape of the upwardly-open wells 2415. FIG. 26 shows the wells 2415 having a triangular cross-sectional shape, although the wells 2415 may have other cross-sectional shapes. As is known to those skilled in the art, a material, such as, for example, a cocktail 2515 of various biological materials, can be disposed in any of the wells 2415 for thermal cycling. The thin walls 2510 of the wells 2415 have an outer surface 2520 that contacts fluid as fluid flows through the thermal cycle flow region 2345 of the flow cell assembly 2315 when the microtiter plate 2310 is disposed on the flow cell assembly 2315.

Figure 32:
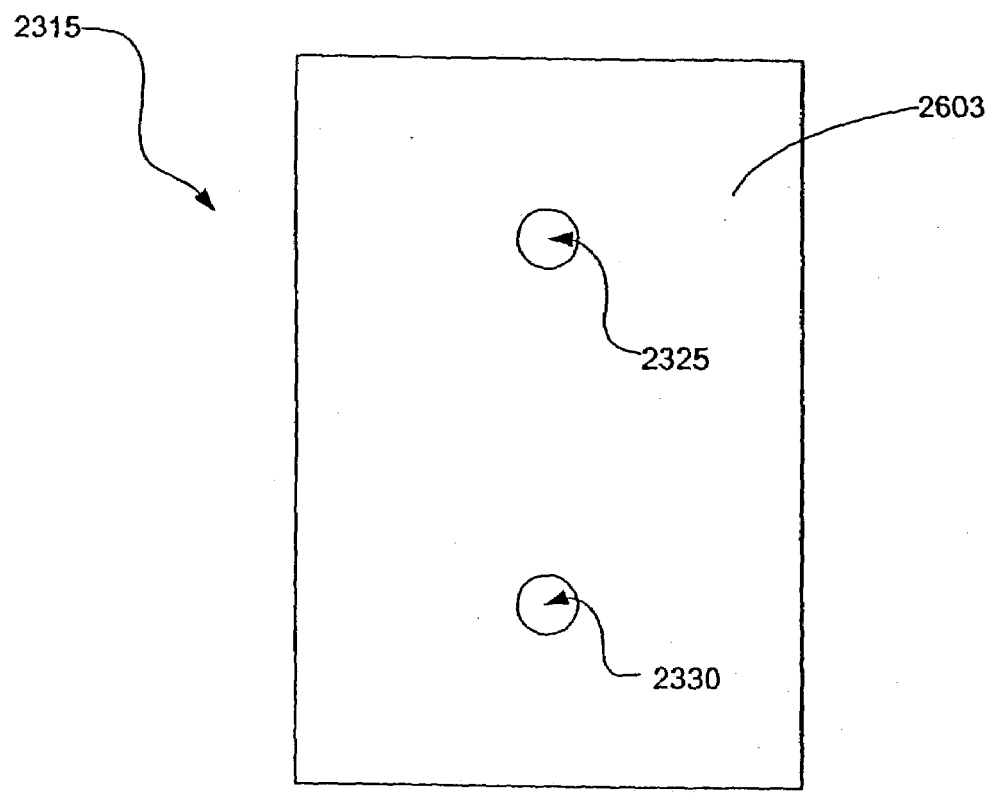
FIG. 32 is a bottom view of the flow cell assembly.

FIG. 27 shows a perspective view of an exploded flow cell assembly 2315, which includes an outer frame 2602 and an insert plate 2620. The frame 2602 has an outer wall 2610 and a bottom wall 2603 that define an interior cavity 2604 that is sized to receive the insert plate 2620. The insert plate 2620 includes a series of guide walls 2625 extend upwardly from an upper surface of the insert plate 2620. A plurality of guide baffles 2606 extend downwardly from the insert plate 2620. The inlet conduit 2325 and outlet conduit 2330 are formed by holes that are located in the bottom wall 2603 to provide a fluid entryway and exit way for the flow cell assembly, as described further below. The bottom view of FIG. 32 shows the inlet and outlet conduit 2325, 2330.

Figure 28:
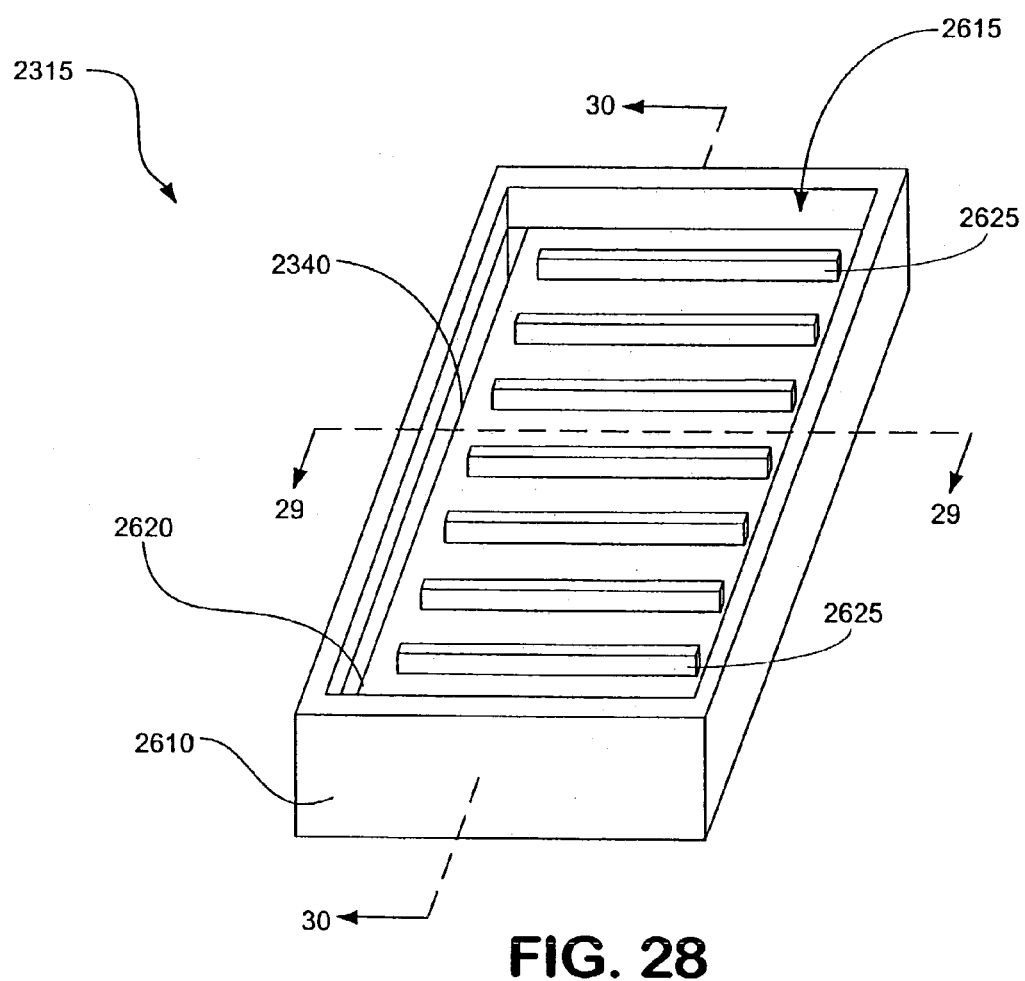
FIG. 28 shows a perspective view of the assembled flow cell assembly.
Figure 29:
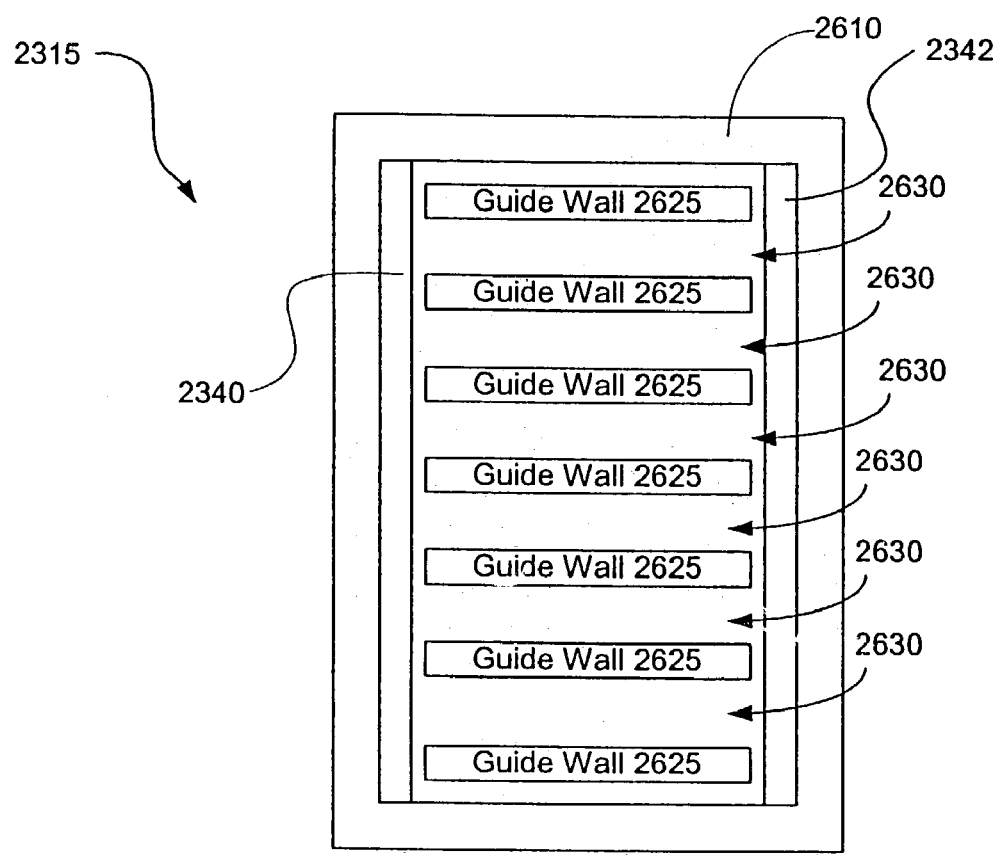
FIG. 29 shows a top view of the assembled flow cell assembly.

The flow cell assembly 2315 is assembled by inserting the insert plate 2620 into the cavity 2604 of the frame 2602. FIG. 28 shows a perspective view of the assembled flow cell assembly 2315 and FIG. 29 shows a top view of the assembled flow cell assembly 2315. As shown in FIGS. 28 and 29, the insert plate 2620 fits into the cavity 2604 to form an upper cavity 2615 that is sized to receive at least a portion of the microtiter plate 2310 therein. The upper cavity 2615 defines the thermal cycle flow region 2345 (shown in FIG. 24) of the flow cell assembly 2315. In the illustrated embodiment, the width of the insert plate 2620 is slightly smaller than the width of the cavity 2604, so that a pair of elongate openings are formed on either side of the insert plate 2620, one opening to form the inlet opening 2340 and the other opening to form the outlet opening 2342. As shown in the top view of FIG. 29 and cross-sectional view of FIG. 30, the inlet opening 2340 is disposed along a first side edge of the insert plate 2620. The corresponding outlet opening 2342 is disposed along a second side edge of the insert plate 2620 opposite the location of the inlet opening 2340.

Figure 30:
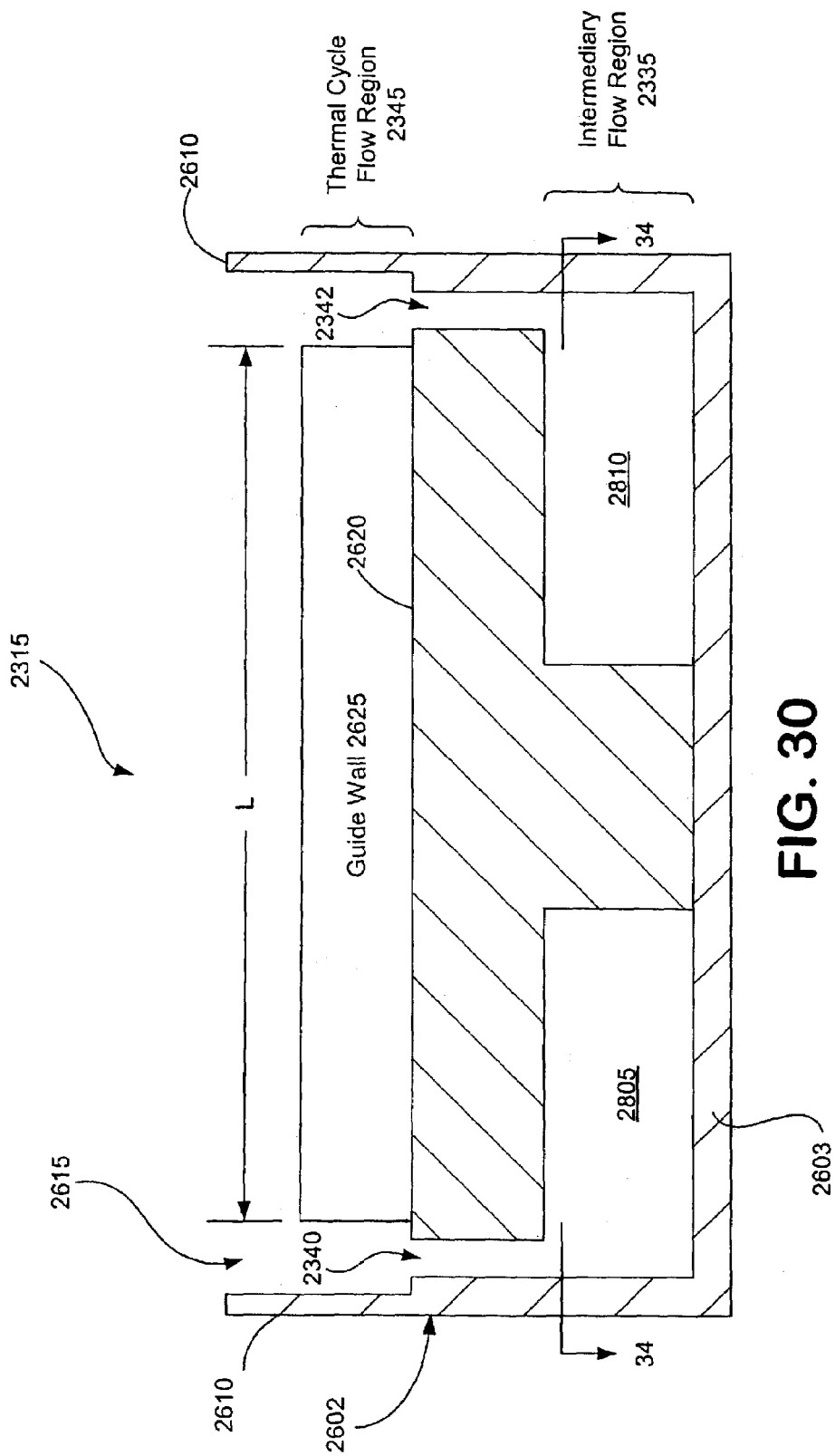
FIG. 30 shows a cross-sectional view of the flow cell assembly along line 29—29 of FIG. 28.

As shown in the cross-sectional view (along line 29—29 of FIG. 28) of the flow cell assembly 2315 in FIG. 30, the insert plate 2620 forms a boundary between the thermal cycle flow region 2345 and the intermediary flow region 2335. The intermediary flow region 2335 includes an inlet cavity 2805 and an outlet cavity 2810 through which fluid can flow into and out of the flow cell assembly. The cavities 2805, 2810 are peripherally surrounded by the exterior wall 2610 of the frame 2602 and enclosed on the bottom by the bottom wall 2603 of the frame 2602. As described below, fluid can flow from the inlet cavity 2805 to the upper cavity 2615 of the thermal cycle flow region 2345 through the inlet opening 2340, which extends through the insert plate 2620. Likewise, fluid can flow into the outlet cavity 2810 from the upper cavity 2615 through the outlet passage 2342, which also extends through the plate insert 2620.

Figure 31:
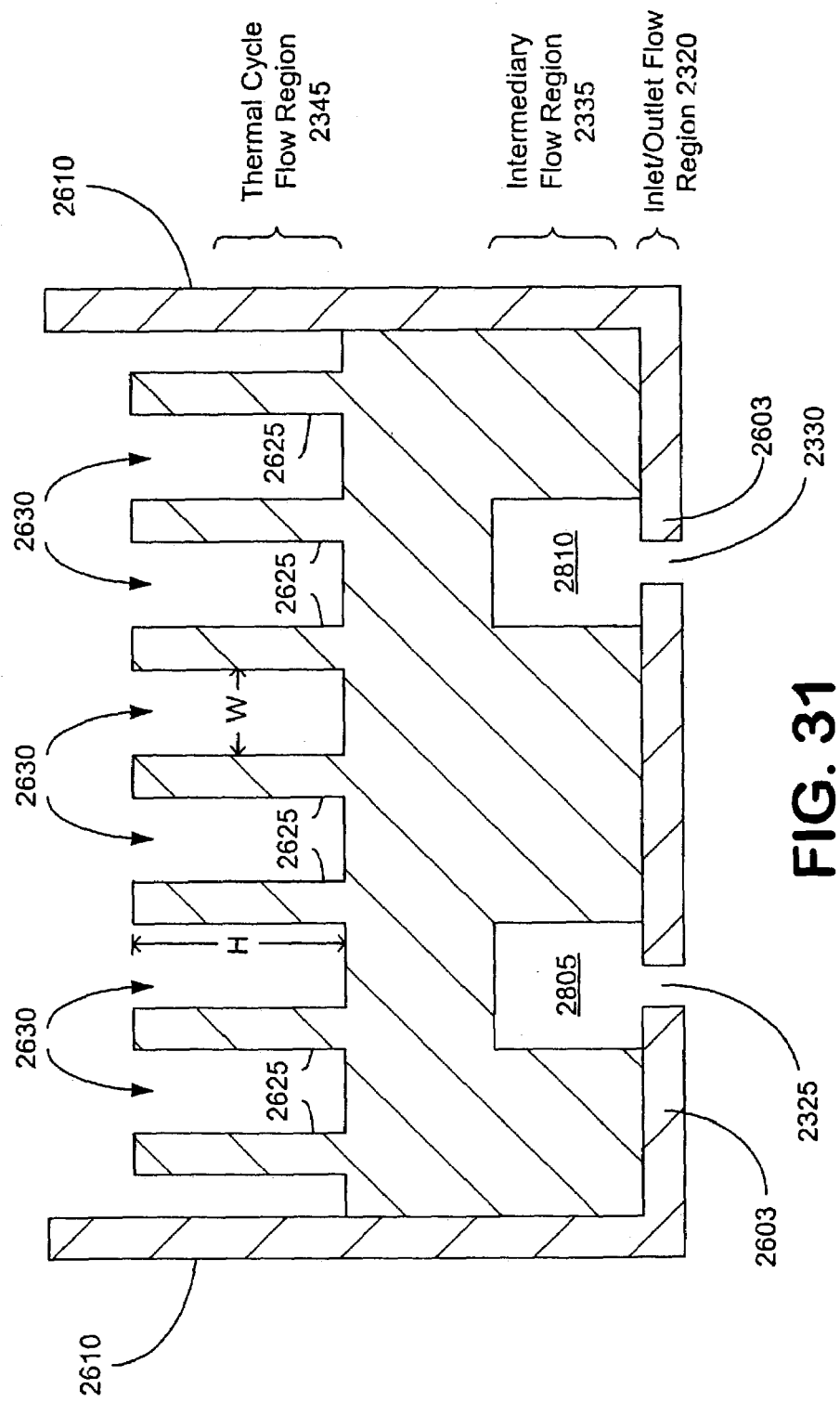
FIG. 31 is a cross-sectional view of the flow cell assembly along the line 30—30 of FIG. 28.

FIG. 31 is a cross-sectional view of the flow cell assembly 2315 along the line 30—30 of FIG. 28. As shown in FIG. 31, the inlet conduit 2325 is formed by a hole in the bottom wall 2603 of the frame 2602. The inlet conduit 2325 leads into the inlet cavity 2805 of the intermediary flow region 2335. The outlet conduit 2330 is also formed by a hole in the bottom wall 2603 of the frame 2602. The outlet conduit 2330 leads into the outlet cavity 2810.

With reference to FIGS. 28–31, the guide walls 2625 extend upwardly from the insert plate 2620 of the upper cavity 2615. The guide walls 2625 are situated so as to form an elongate flow channel 2630 between each adjacent pair of guide walls 2625. As best shown in the top view of FIG. 29 and the cross-sectional view of FIG. 30, each guide wall 2625 (and corresponding flow channel 2630) is elongated and has a length L that extends substantially from the inlet opening 2340 to the outlet opening 2342. As shown in FIG. 31, each flow channel has a height H and a width W. The height H, width W, and length L of the flow channel 2630 can vary based on the microtiter plate that is used with the flow cell assembly. That is, the flow channel preferably has a width and height such that the wells of the microtiter plate can fit within the flow channel. The length L is preferably sufficiently large such that a row of wells of the microtiter plate can be inserted into the flow channel.

Figure 33:
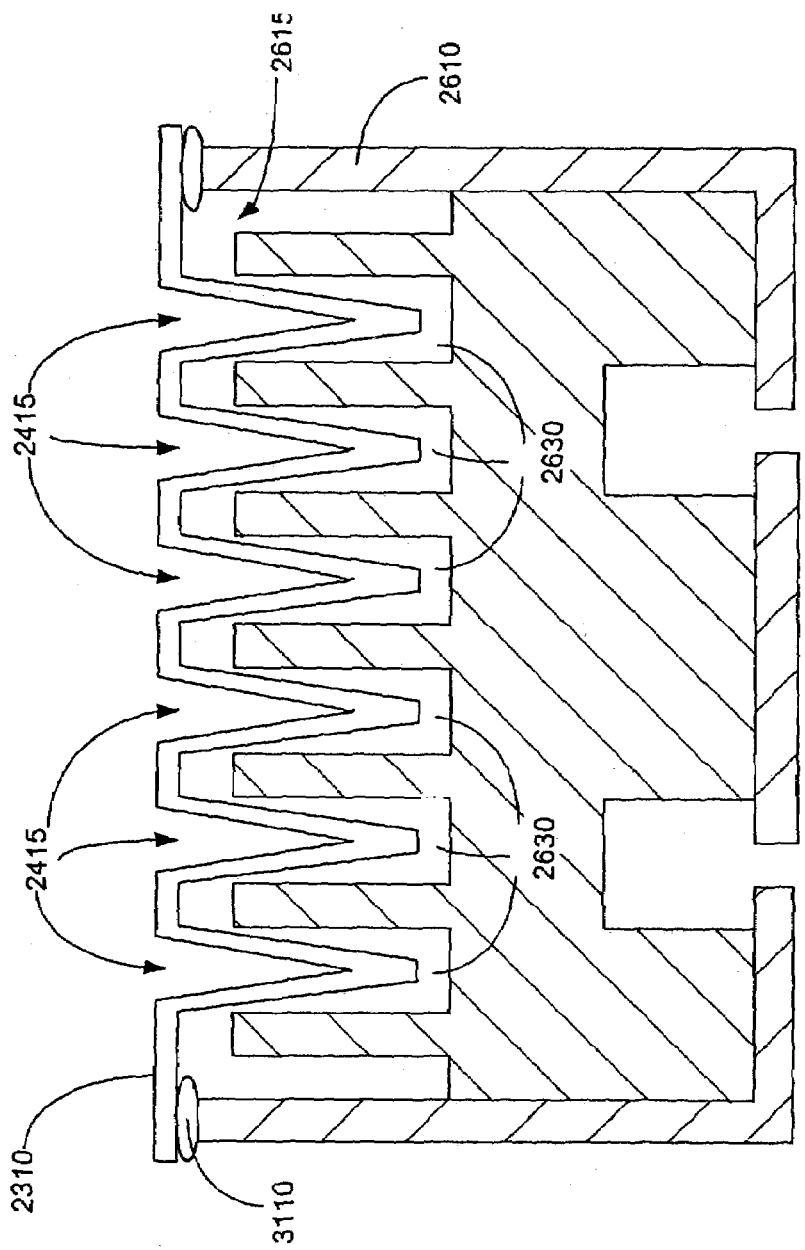
FIG. 33, shows a cross-sectional view of the microtiter plate assembly, showing the microtiter plate positioned in the upper cavity of the flow cell assembly.

As mentioned, the upper cavity 2615 is sized to receive the microtiter plate 2310. When the microtiter plate 2310 is positioned within the upper cavity 2615 of the flow cell assembly, each of the wells 2415 of the microtiter plate 2310 extends downwardly into a corresponding flow channel 2630. In one embodiment, the quantity and spacing of the flow channels 2630 is substantially equal to the quantity and spacing of the rows of wells 2415 on a corresponding microtiter plate 2310. Thus, each row of wells 2415 can be inserted into a corresponding flow channel 2630 when the microtiter plate 2310 is placed within the upper cavity 2615 of the flow cell assembly 2315. An example of this is shown in FIG. 33, which shows the microtiter plate 2310 positioned in the upper cavity 2615 of the flow cell assembly 2315. When positioned as such, each of the six rows of wells 2415 extends downwardly into a corresponding flow channel 2630 of the flow cell assembly 2315. In this regard, the width W of each flow channel 2630 is preferably large enough to accommodate insertion of a row of microtiter plate well 2315 into the flow channel 2630.

Figure 34:
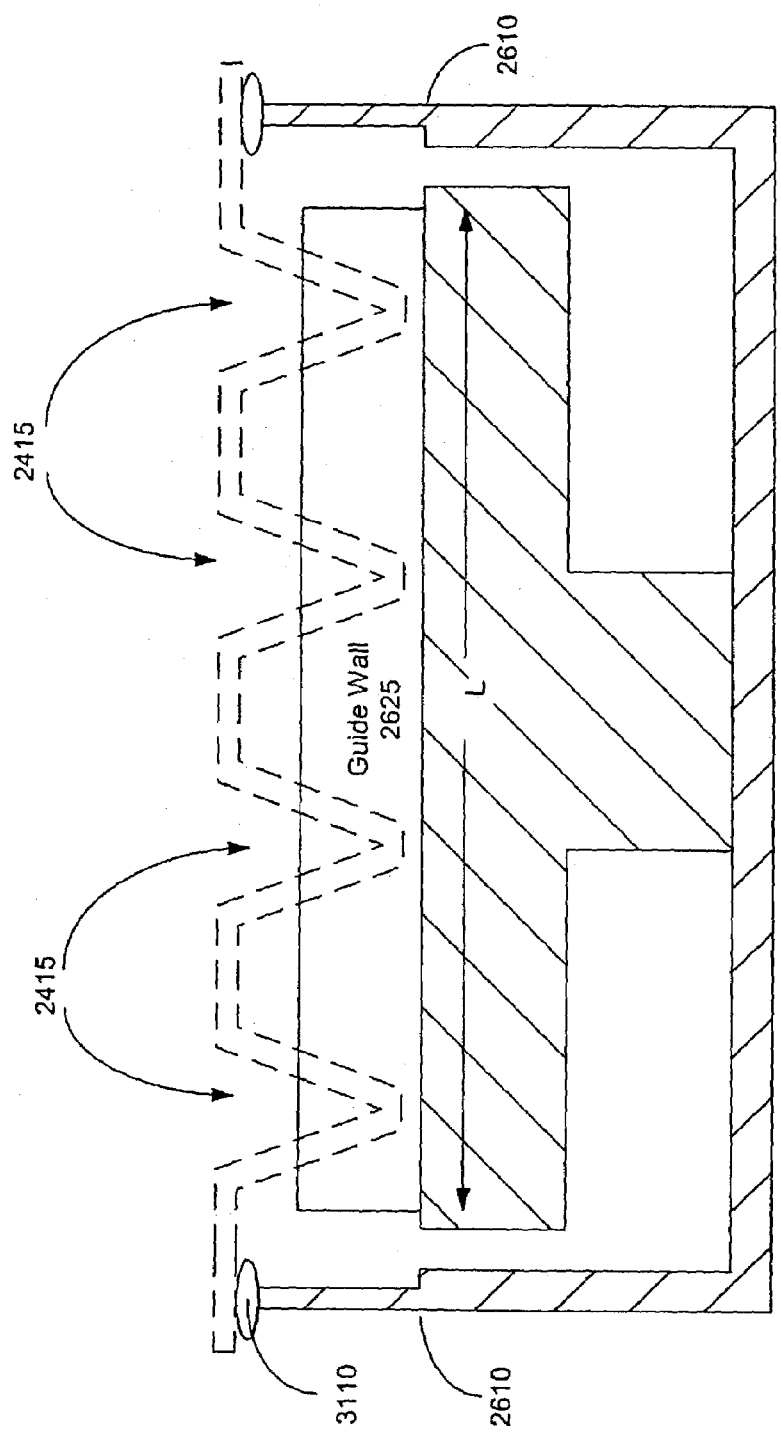
FIG. 34 shows a cross-sectional view of the microtiter plate assembly, showing the microtiter plate positioned in the upper cavity of the flow cell assembly, the view being along the length of one of the flow channels.

FIG. 34 shows another view of the microtiter plate 2310 positioned in the upper cavity 2615 of the flow cell assembly 2315, the view being along the length of one of the flow channels 2630. The microtiter plate 2310 is shown in phantom lines in FIG. 34 for clarity of illustration. The length L of the guide wall 2625 that forms the flow channel 2630 is preferably larger than the length of the corresponding row of wells 2415 so that the flow channel 2630 can accommodate the entire row of wells 2415.

With reference still to FIGS. 33 and 34, an upper end of the exterior frame wall 2610 can support a portion of the microtiter plate 2310. A sealing ring 3110 can be positioned over the upper end of the exterior wall 2610 so that the sealing ring 3110 is interposed between the upper end of the exterior wall 2610 and the microtiter plate 2310. The sealing ring 3110 can extend around the entire upper edge of the exterior wall 2610 (which surrounds the upper cavity 2615) to thereby seal the upper cavity 2615 shut when the microtiter plate 2310 is positioned atop the side wall 2610. The sealing ring 3110 can be made of a deformable material that conforms to shape of the upper end of the exterior wall 2610 to provide a reliable seal.

Figure 35:
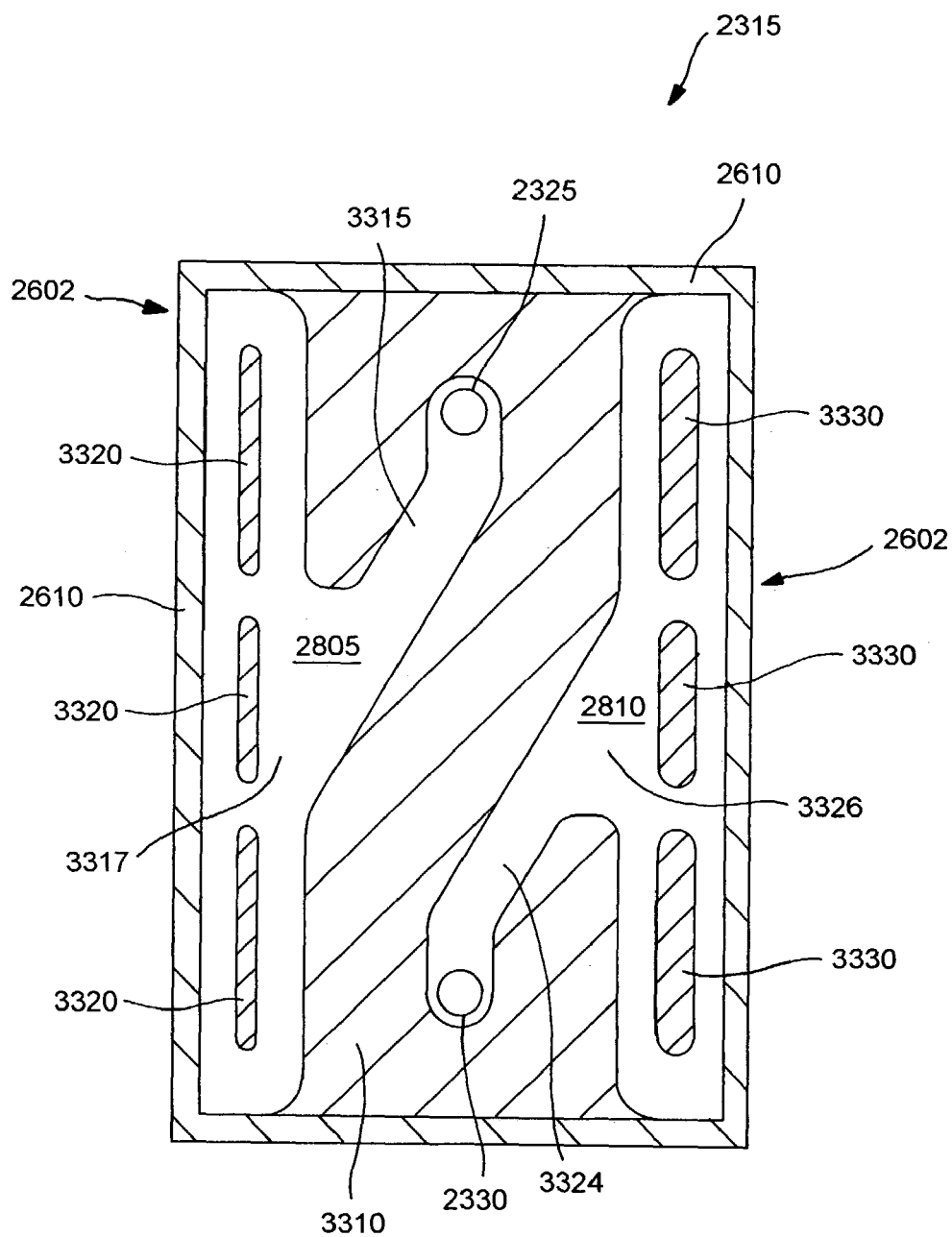
FIG. 35 is a cross-sectional view of the microtiter plate assembly, looking downward along the line 34—34 of FIG. 30 and showing an inlet cavity and an outlet cavity.

FIG. 35 is a cross-sectional view of the flow cell assembly 2315, looking downward along the line 34—34 of FIG. 30 and showing a top view of the inlet cavity 2805 and outlet cavity 2810. A main baffle 3310 forms an inlet passage 3315 of the inlet cavity 2805. The inlet passage 3315 communicates with the inlet conduit 2325. As described below, a fluid can flow into the inlet passage 3315 through the inlet conduit 2325. The inlet passage 3315 originates at the inlet conduit 2325 (which is located substantially in an interior of the frame 2602) and moves toward one side of the frame 2602. The inlet passage 3315 has a narrow shape and extends from the inlet conduit 2325 to a diffusion region 3317 that substantially widens in size with respect to the inlet passage 3315. A plurality of diffuser baffles 3320 are located in the diffusion region 3317. The diffuser baffles 3320 are elongate and narrow in shape and are oriented substantially parallel to the side wall 2610 of the frame 2602 so that the diffuser baffles are located at the inlet openings to the upper cavity.

With reference to FIG. 35, the main baffle 3310 also forms an outlet passage 3324 of the outlet cavity 2810. The outlet passage 3324 mirrors the shape of the inlet passage 3315. The outlet passage 3324 communicates with the outlet conduit 2330 in the frame 2602. The outlet passage 3324 widens in size to form a diffusion region 3326 that contains a plurality of diffuser baffles 3330.

The operation of the microtiter plate assembly 2110 is now described. As discussed above, the microtiter plate assembly 2110 comprises a microtiter plate 2310 that has been removably positioned atop a flow cell assembly 2315. FIG. 23 shows a plurality of microtiter plate assemblies 2110 that are positioned at thermal cycling stations 2105. The operation of the microtiter plate assemblies 2110 is described with reference to a single microtiter plate assembly 2110, shown in FIG. 36, which includes a single microtiter plate 2310 removably positioned atop the flow cell assembly 2315. The microtiter plate assembly 2110 is coupled to an inlet pipe 2135 and an outlet pipe 2140. The inlet pipe 2135 is inserted into the inlet conduit 2325 so that the inlet pipe 2135 fluidly communicates with the inlet cavity 2805. The outlet pipe 2140 is inserted into the outlet conduit 2330 so that the outlet pipe 2140 fluidly communicates with the outlet cavity 2810. A temperature controlled fluid flows into the inlet cavity 2805 via the inlet pipe 2135, as represented by the arrow 3510. The fluid originates from one of the reservoirs 2115 and flows to the inlet pipe 2135 via the valve and manifold system 2130, as described above with reference to FIG. 23.

Figure 37:
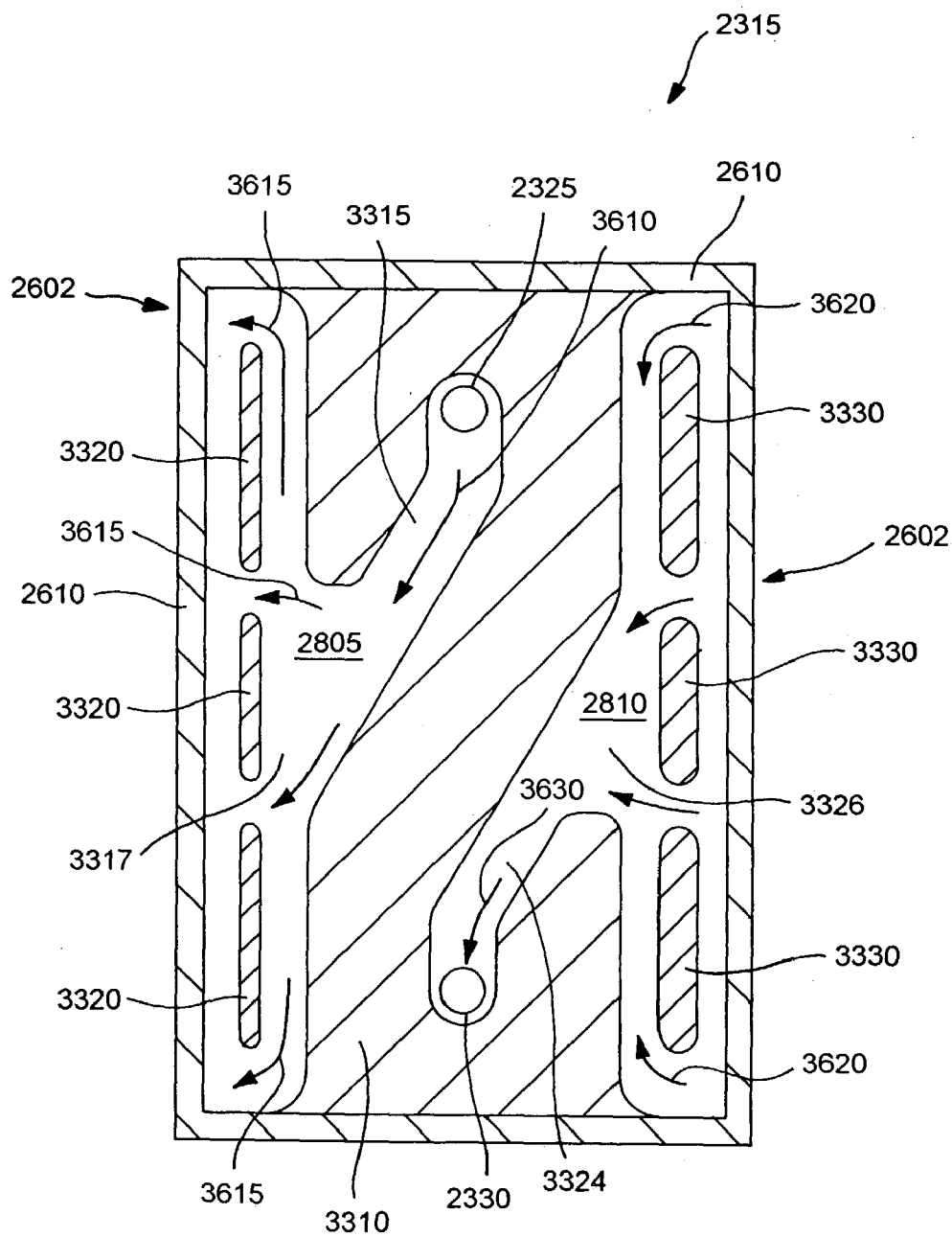
FIG. 37 which shows a downward-looking view of the inlet cavity and the outlet cavity of the microtiter plate assembly, and shows the fluid flow path through the cavities.

The operation of the microtiter plate assembly 2110 is now further described with reference to FIG. 37, which shows a downward-looking view of the inlet cavity 2805 and the outlet cavity 2810. The temperature-controlled fluid flows into the inlet cavity 2805 via the inlet conduit 2325. The fluid then flows through the inlet passage 3315 in a direction represented by the arrow 3610. The inlet passage 3315 guides the fluid toward the diffusion region 3317 of the inlet cavity 2805. The diffusion region 3317 widens in size and contains the diffuser baffles 3320. As fluid flows through the diffusion region 3317, the diffuser baffles 3320 diffuse the fluid by causing the fluid to flow through spaces between each of the diffuser baffles 3320, as represented by the arrows 3615. The diffuser baffles 3320 break up the flow of fluid flow and cause the fluid to evenly distribute as it flows toward a side edge of the inlet passage 2805.

Figure 38:
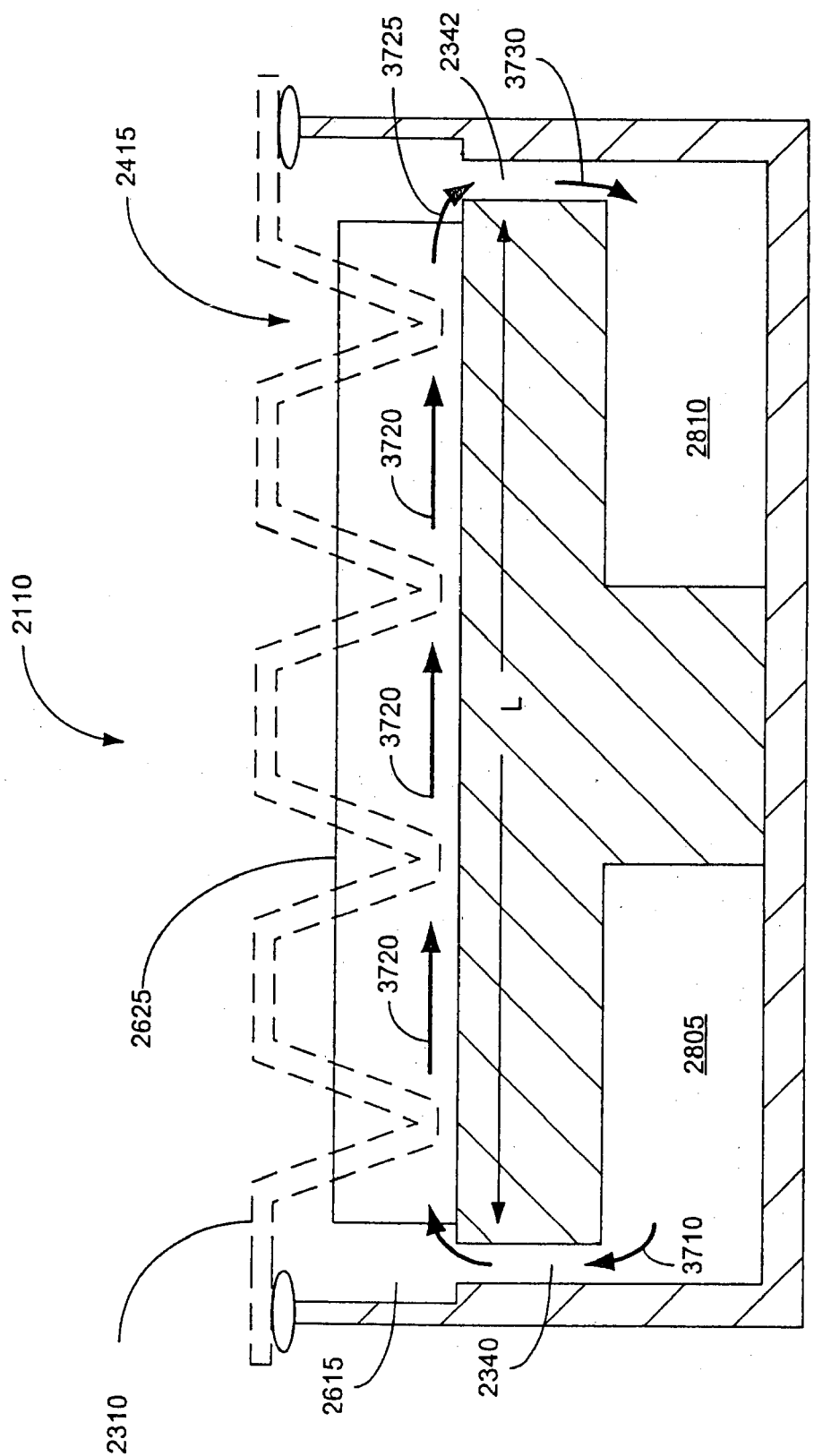
FIG. 38 shows a cross-sectional view of the microtiter plate assembly and shows a fluid flow path.

With reference now to FIG. 38, the fluid flows upwardly into the inlet opening 2340 from the inlet passage 2805, as represented by the arrow 3710. The fluid flows upwardly through the inlet opening 2340 and into the upper cavity 2615, where the wells of the microtiter plate 2310 are located. The fluid then flows through the flow channels 2630 (shown in FIG. 29) that are formed in between the guide walls 2625, as represented by the arrows 3720 of FIG. 38.

Figure 39:
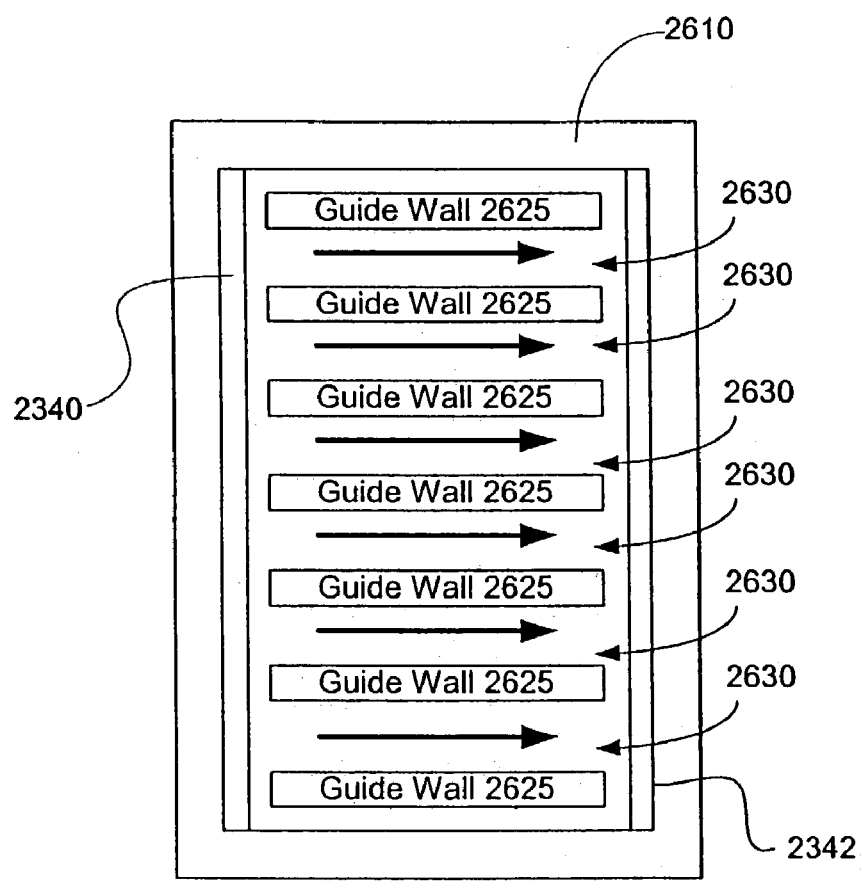
FIG. 39 shows a top view of the microtiter plate assembly and shows a fluid flow path.

The fluid flow through the flow channels of the guide walls 2625 is described in more detail with reference to FIG. 39, which shows a top view of the microtiter plate assembly 2110 (the microtiter plate 2310 is omitted from FIG. 39 for clarity of illustration). The guide walls 2625 further diffuse the fluid flow into the separate flow channels 2630 that are situated between each of the guide walls 2625. As represented by the bolded arrows in FIG. 39, the fluid flows in a straight line between each of the guide walls 2625. Thus, the guide walls 2625 guide the fluid from the inlet opening 2340 toward the outlet opening 2342.

In addition to guiding the fluid from the inlet opening 2340 toward the outlet opening 2342, the guide walls 2625 also guide the fluid so that it contacts the bottom surface of the wells 2415 of the microtiter plate 2320, as shown in FIG. 38. As discussed above, the fluid is set to a predetermined temperature. The fluid can be used to cool the wells 2415 or to transfer heat to the wells 2415, depending on the temperature differential between the fluid and the wells 2415. In this manner, the wells can be thermally cycled. Advantageously, the guide walls 2625 guide the fluid in such a manner that the fluid flows in a straight line over the wells 2415, thereby eliminating uneven or turbulent fluid flow over the wells of the microtiter plate. This provides for a more even heat transfer between the fluid and the microtiter plate. The guide walls 2625 also ensure that fluid contacts all of the wells of the microtiter plate.

With reference still to FIG. 38, the fluid next flows downwardly into the outlet opening 2342 from the upper cavity 2615, as represented by the arrow labeled 3725. The fluid flows downwardly through the outlet opening 2342 into the outlet cavity 2810, as represented by the arrow labeled 3720. The fluid flow through the outlet cavity 2810 is now described with reference to FIG. 37. Once the fluid enters the outlet cavity 2810, the fluid flows around the diffuser baffles 3330 toward the outlet passage 3324, as represented by the arrows labeled 3620. The fluid enters the outlet passage 3324 and flows into the outlet conduit 2330, as represented by the arrow labeled 3630.

Figure 36:
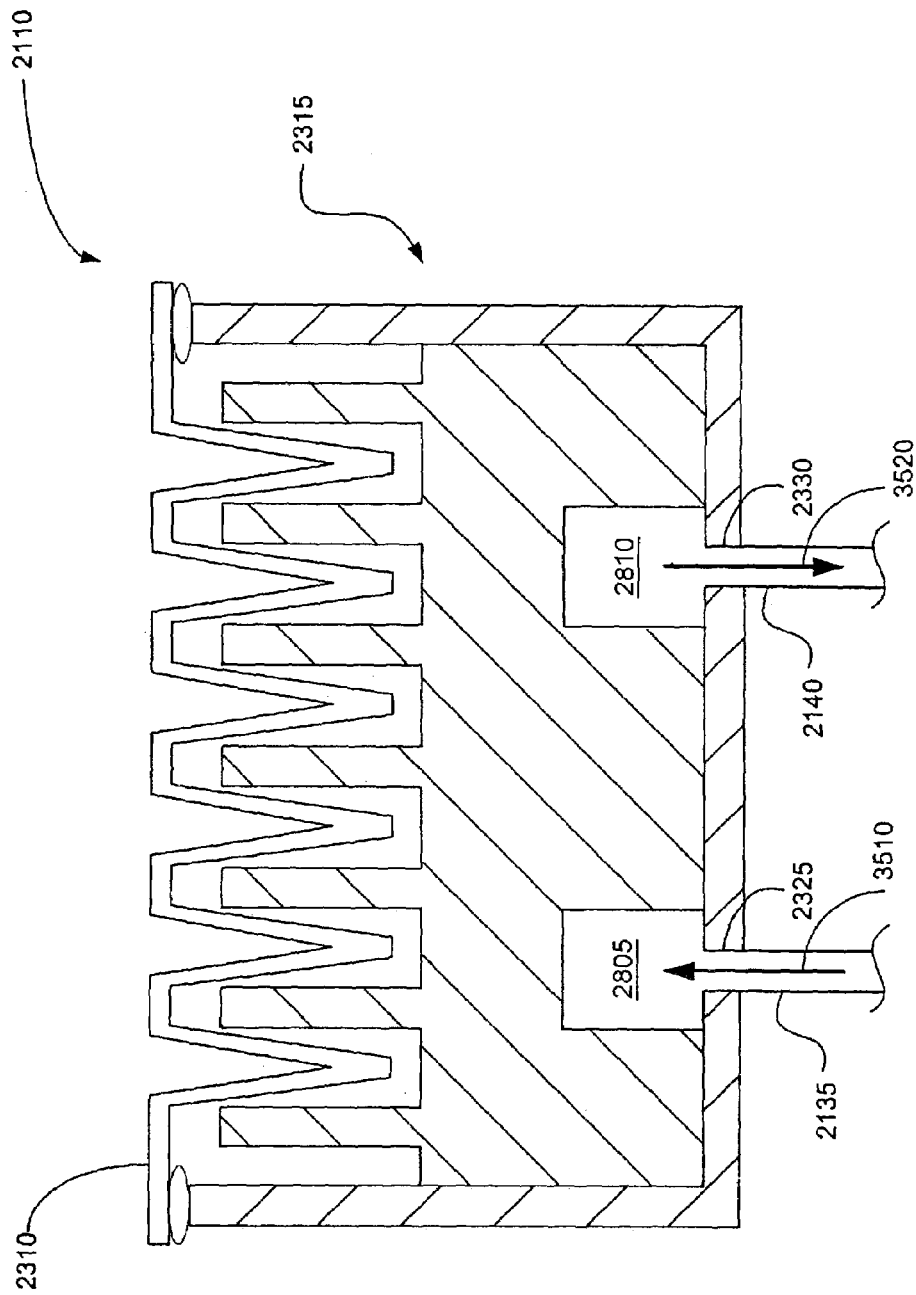
FIG. 36 shows a cross-sectional view of the microtiter plate assembly coupled to an inlet pipe and an outlet pipe and shows the flow of fluid into the microtiter plate assembly.

With reference now to FIG. 36, the fluid exits the outlet cavity through the outlet conduit 2140, as represented by the arrow labeled 3520. As discussed above, the outlet conduit 2330 fluidly communicates with the outlet pipe 2140 (shown in FIGS. 23 and 36). The fluid flows into the outlet pipe

2140, which guides the fluid back into the appropriate reservoir 2115 via the valve and manifold system 2130, shown in FIG. 23.

Plate Sealing

The microtiter plates used with the automated process line 100 are typically sealed with an aluminum or polypropylene adhesive film. This prevents evaporation during thermal reactions. But it is possible to get some condensation of solution on the inside of the seal. Therefore, the plates are subjected to a centrifuge so that the solution collects at the bottom of the microtiter plate wells, although there is still a very small chance of some sample collecting on the inside of the seal. When the seal is removed, it is important that there be no cross contamination of samples. To avoid this, the system 100 uses a "peeler" comprising a robotic arm. The seal for the microtiter plates is designed to be bigger than the plate, and a portion of the sealing film extends out from the plate on the short axis (or it may be on the long axis if a different movement of the robotic arm is configured). The microtiter plate, while moving down the conveyor, is stopped at a defined position and there the plate is the gripped and held steady.

A robotic arm with a different gripper that has fingers which can touch each other then maneuvers, such that the gripper fingers locate the film and tighten, and so grip the film. The robotic arm then raises slightly and then moves along the length of the microtiter plate. As it moves it pulls the sealing film with sufficient force so as to break the adhesive pull that the film has for the microtiter plate. The gripper moves at such a height as to ensure that the originally inward side of the seal is now pointing upward away from the remainder of the sealed microtiter plate. The angle of the removing seal is such that should any droplets of solution or sample be on the inside of the seal that it does not move down the surface of the film and therefore possibly back into a different open well of the microtiter plate. The nature of the film surface is chosen to have sufficient surface tension for the solution or sample being used to ensure minimal or ideally no movement of a droplet on the film except at an extreme angle or force not typically encountered.

The present invention has been described above in terms of a presently preferred embodiment so that an understanding of the present invention can be conveyed. There are, however, many configurations for sample handling systems not specifically described herein but with which the present invention is applicable. The present invention should therefore not be seen as limited to the particular embodiments described herein, but rather, it should be understood that the present invention has wide applicability with respect to sample handling generally. All modifications, variations, or equivalent arrangements and implementations that are within the scope of the attached claims should therefore be considered within the scope of the invention.

What is claimed is:

1. A method of operating a computer-controlled process line that dispenses particle material into locations of a solid support having multiple locations, the method comprising: positioning an array of hollow tubes above a reservoir containing a bed of particle material; engaging the tube array with the reservoir such that the lower ends of the tubes are pressed into the particle bed and a volume of particle material is forced into the tubes; disengaging the tube array from the reservoir such that the volume of particle material is retained within each of the tubes, wherein the retained volume is defined by the tube from the lower end of each tube to a plunger within each tube; positioning the array above the solid support such that the lower ends of the tubes are located above corresponding locations of the solid support; using the plungers to push the particle material retained within each tube out into the corresponding locations of the solid support; and packing the solid material within the reservoir by engaging the bed of particle material with a compacting cover.

2. A method as defined in claim 1, wherein the number of hollow tubes in the array is equal to the number of locations in the solid support.

3. A method as defined in claim 1, wherein the array of hollow tubes comprises 96 hollow tubes.

4. A method as defined in claim 3, wherein the hollow tubes in the array of hollow tubes are arranged in a grid of eight by twelve.

5. A method as defined in claim 1, wherein the array of hollow tubes comprises 384 hollow tubes.

6. A method as defined in claim 5, wherein the hollow tubes in the array of hollow tubes are arranged in a grid of sixteen by twenty-four.

7. A method as defined in claim 1, wherein the array of hollow tubes comprises 1536 hollow tubes.

8. A method as defined in claim 7, wherein the hollow tubes in the array of hollow tubes are arranged in grid of thirty-two by forty-eight.

9. A method as defined in claim 1, further comprising shaking the reservoir to flatten the bed of particle material.

10. A method as defined in claim 1, wherein the solid material comprises resin.

11. A method as defined in claim 1, wherein the step of packing the solid reagent comprises lifting the reservoir into the compacting cover until the bed of particle material is squeezed against an inside surface of the cover.

12. A method as defined in claim 1, wherein the plungers are connected to a plunger plate, and wherein the plungers are moved downward simultaneously using the plunger plate.

13. A method as defined in claim 1, wherein each of the hollow tubes in the array of hollow tubes is simultaneously cleaned by a skimming plate positioned between the array of hollow tubes and the reservoir, said skimming plate comprising a number of holes, each of said holes sized to slideably insert the hollow tubes therethrough.

14. A method as defined in claim 1, wherein the solid support comprises a microtiter plate and the locations comprise wells within said microtiter plate.

15. A method as defined in claim 1, wherein engaging the tube with the reservoir is performed by lowering the tube array until the lower ends of the tubes are pressed into the particle bed.

16. A method as defined in claim 1, wherein disengaging the tube array from the reservoir is performed by raising the tube array out of the reservoir.

17. A solid reagent dispensing station for filling locations of one or more solid supports with particles of solid reagent, said dispensing station comprising:
a dispenser assembly comprising: a first plate; a second plate; an array of hollow tubes coupled to the first plate; and an array of plungers coupled to the second plate, each of said plungers slideably inserted into the hollow tubes, wherein the second plate is configured to slide the plungers simultaneously up and down within the hollow tubes;
a reservoir configured to contain a bed of solid reagent particles, said reservoir sized to receive the array of hollow tubes, said reservoir including a collar with an open proximal end, an open distal end, and an inner surface; a base comprising an outer surface, said base shaped to sealably slide through the distal end of the collar, its outer surface in contact with the inner surface of the collar; and a compacting lid removably engaged to the collar;

a conveyor for transporting said one or more solid supports through the dispensing station; and a transport mechanism connected to the dispenser assembly, the transport mechanism configured to transport the dispenser assembly between the reservoir and the one or more solid supports.

18. The solid reagent dispensing station of claim 17, wherein the number of hollow tubes in the array of hollow tubes equals the number of locations in one of the said one or more solid supports.

19. The solid reagent dispensing station of claim 17, wherein the array of hollow tubes comprises 96 hollow tubes.

20. The solid reagent dispensing station of claim 19, wherein the hollow tubes in the array of hollow tubes are arranged in a grid of eight by twelve.

21. The solid reagent dispensing station of claim 17, wherein the array of hollow tubes comprises 384 hollow tubes.

22. The solid reagent dispensing station of claim 21, wherein the hollow tubes in the array of hollow tubes are arranged in a grid of sixteen by twenty-four.

23. The solid reagent dispensing station of claim 17, wherein the array of hollow tubes comprises 1536 hollow tubes.

24. The solid reagent dispensing station of claim 23, wherein the hollow tubes in the array of hollow tubes are arranged in a grid of thirty-two by forty-eight.

25. The solid reagent dispensing station of claim 17, wherein the solid reagent comprises resin.

26. The solid reagent dispensing station of claim 17, wherein the station is an automated station controlled by a computer.

27. The solid reagent dispensing station of claim 17, wherein each of said hollow tubes has a proximal end with an opening, a distal end with an opening, and an inside surface, wherein each of said plungers comprises a proximal end and a distal end, and wherein a space is formed between the distal end of each of the plungers and the distal end of each of the hollow tubes, said space defining a predetermined volume sufficient for containing a predetermined amount of solid reagent.

28. The solid reagent dispensing station of claim 17 wherein the compacting lid has a stick-resistant lower surface.

29. A solid reagent dispensing station for filling locations of one or more solid supports with particles of solid reagent, said dispensing station comprising:

a dispenser assembly comprising: a first plate; a second plate, an array of hollow tubes coupled to the first plate; and an array of plungers coupled to the second plate, each of said plungers slideably inserted into the hollow tubes, wherein the second plate is configured to slide the plungers simultaneously up and down within the hollow tubes;

a reservoir configured to contain a bed of solid reagent particles, said reservoir sized to receive the array of hollow tubes;

a conveyor for transporting said one or more solid supports through the dispensing station;

a transport mechanism connected to the dispenser assembly, the transport mechanism configured to transport the dispenser assembly between the reservoir and the one or more solid supports; and a compacting lid having a flat lower surface, said compacting lid configured for lowering onto the reservoir and exerting pressure on the particles of reagent.

30. The solid reagent dispensing station of claim 29, wherein the lower surface of the compacting lid comprises a stick-resistant material.

31. The solid reagent dispensing station of claim 17, wherein the hollow tubes are cylindrical.

32. The solid reagent dispensing station of claim 17, further comprising a skimming plate suspended over the reservoir.

33. The solid reagent dispensing station of claim 32, wherein the skimming plate has a number of holes equal to the number of hollow tubes in the array, each of said holes sized to slideably insert the hollow tubes therethrough.

34. The solid reagent dispensing station of claim 17, wherein the solid support comprises a microtiter plate and the locations comprise wells within said microtiter plate.

35. An apparatus for dispensing particle material into locations of a solid support having multiple locations, the apparatus comprising: a first plate having a top surface and a bottom surface, said top surface having an array of holes leading into a corresponding array of hollow chambers; an array of hollow tubes attached to the bottom surface of said first plate, said array of hollow tubes aligned with the holes and the hollow chambers; a second plate having a top surface and a bottom surface; an array of plungers attached to the bottom surface of said second plate, wherein the array of plungers and array of holes is aligned and the plungers of the array are inserted into the holes and extend into the hollow tubes; one or more springs mounted in between the top surface of the first plate and the bottom surface of the second plate, forcing the two plates apart; and one or more stop posts connecting the first plate to the second plate; and a computer controlled pneumatic pump in communication with the top surface of the second plate, said pump configured to apply a downward force on the second plate.

36. The apparatus of claim 35, wherein the number of hollow tubes is equal to the number of plungers.

37. The apparatus of claim 35, wherein the first and second plates are substantially flat.

38. The apparatus of claim 35, further comprising: a third plate; two lateral walls connecting the first flat plate to the third flat plate; and an adjustment screw threaded through a hole in the third plate, said screw protruding through the bottom of the third plate and resting against the top of the second plate, said adjustment screw setting the second plate a predetermined maximum distance from the first plate.

39. The apparatus of claim 38, wherein the adjustment screw comprises markings representative of a volume of space within the hollow tubes.

40. The apparatus of claim 35, wherein the solid support comprises a microtiter plate and the locations comprise wells within said microtiter plate.

41. A solid reagent dispensing station for filling locations of one or more solid supports with particles of solid reagent, said dispensing station comprising:

a reservoir configured to contain a bed of solid reagent particles, the reservoir including a collar with an open proximal end, an open distal end, and an inner surface; a base comprising an outer surface, said base shaped to sealably slide through the distal end of the collar, its outer surface in contact with the inner surface of the collar; and a compacting lid removably engaged to the collar;

a skimming plate having an array of holes, said skimming plate positioned above the reservoir; and dispenser means for withdrawing a plurality of predetermined volumes of the solid reagent particles through the holes of the skimming plate and dispensing them in the locations of the one or more solid supports.

42. The solid reagent dispensing station of claim 41 further comprising a transport mechanism, wherein said transport mechanism comprises: at least one position sensor for detecting the position of the dispenser means; and a guide rail that is coupled to the dispenser means.

43. The solid reagent dispensing station of claim 41, wherein the reservoir comprises a hollow compacting lid and a vibrator plate inside the hollow compacting lid.

44. The solid reagent dispensing station of claim 42, wherein the reservoir slideably rests on one or more tracks which are substantially perpendicular to the guide rail.

45. The solid reagent dispensing station of claim 41, wherein the solid support comprises a microtiter plate.

46. The solid reagent dispensing station of claim 41, wherein the dispenser means comprises an array of hollow tubes, each of which receives a plunger slideably inserted therein.

47. The solid reagent dispensing station of claim 46, wherein the number of holes in the array of holes is equal to the number of hollow tubes in the array of hollow tubes, and wherein the hollow tubes in the array of hollow tubes are arranged for complementary fit with the holes in the array of holes.

* * * * *